(12) United States Patent
Terbrueggen et al.

(10) Patent No.: US 10,463,347 B2
(45) Date of Patent: *Nov. 5, 2019

(54) DEVICES AND METHODS FOR COLLECTING AND STABILIZING BIOLOGICAL SAMPLES

(71) Applicant: DXTERITY DIAGNOSTICS INCORPORATED, Rancho Dominguez, CA (US)

(72) Inventors: Robert Terbrueggen, Manhattan Beach, CA (US); Scott Gordon Beach, Carlsbad, CA (US)

(73) Assignee: DXTERITY DIAGNOSTICS INCORPORATED, Rancho Dominguez, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/699,980

(22) Filed: Sep. 8, 2017

(65) Prior Publication Data

US 2018/0153522 A1   Jun. 7, 2018

Related U.S. Application Data

(63) Continuation of application No. 14/736,220, filed on Jun. 10, 2015, now Pat. No. 9,757,095.

(60) Provisional application No. 62/010,314, filed on Jun. 10, 2014.

(51) Int. Cl.
*A61B 10/00* (2006.01)
*B01L 3/00* (2006.01)

(52) U.S. Cl.
CPC ........ *A61B 10/0045* (2013.01); *B01L 3/5023* (2013.01); *B01L 3/5029* (2013.01); *A61B 2560/0406* (2013.01); *B01L 2200/025* (2013.01); *B01L 2200/0689* (2013.01); *B01L 2200/16* (2013.01); *B01L 2300/021* (2013.01); *B01L 2300/022* (2013.01); *B01L 2300/044* (2013.01); *B01L 2300/047* (2013.01); *B01L 2300/0609* (2013.01); *B01L 2300/069* (2013.01); *B01L 2300/0672* (2013.01); *B01L 2300/087* (2013.01); *B01L 2300/0832* (2013.01); *B01L 2300/0867* (2013.01); *B01L 2300/123* (2013.01); *B01L 2400/0683* (2013.01)

(58) Field of Classification Search
CPC .......................... A61B 10/0045; B01L 3/5029
See application file for complete search history.

(56) References Cited

U.S. PATENT DOCUMENTS

| 4,469,863 A | 9/1984 | Ts'o et al. |
|---|---|---|
| 5,034,506 A | 7/1991 | Summerton et al. |
| 5,185,243 A | 2/1993 | Ullman et al. |
| 5,216,141 A | 6/1993 | Benner |
| 5,235,033 A | 8/1993 | Summerton et al. |
| 5,346,994 A | 9/1994 | Chomczynski |
| 5,386,023 A | 1/1995 | Sanghvi et al. |
| 5,476,930 A | 12/1995 | Letsinger et al. |
| 5,514,546 A | 5/1996 | Kool |
| 5,602,240 A | 2/1997 | De Mesmaeker |
| 5,637,684 A | 6/1997 | Cook et al. |
| 5,644,048 A | 7/1997 | Yau |
| 5,674,683 A | 10/1997 | Kool |
| 5,681,943 A | 10/1997 | Letsinger et al. |
| 5,683,874 A | 11/1997 | Kool |
| 5,714,320 A | 2/1998 | Kool |
| 5,780,613 A | 7/1998 | Letsinger et al. |
| 5,808,036 A | 9/1998 | Kool |
| 6,077,668 A | 6/2000 | Kool |
| 6,140,480 A | 10/2000 | Kool |
| 6,218,108 B1 | 4/2001 | Kool |
| 6,264,619 B1 | 7/2001 | Ferguson |
| 6,265,166 B1 | 7/2001 | Frank-Kamenetskii et al. |
| 6,479,650 B1 | 11/2002 | Kool |
| 6,511,810 B2 | 1/2003 | Bi et al. |
| 6,670,193 B2 | 12/2003 | Kool |
| 6,942,771 B1 | 9/2005 | Kayyem |
| 6,955,901 B2 | 10/2005 | Schouten |
| 7,033,753 B1 | 4/2006 | Kool |
| 7,153,658 B2 | 12/2006 | Anderson et al. |
| 7,198,900 B2 | 4/2007 | Woudenberg et al. |

(Continued)

FOREIGN PATENT DOCUMENTS

| EP | 320308 | 6/1989 |
|---|---|---|
| EP | 439182 | 7/1991 |

(Continued)

OTHER PUBLICATIONS

Abe et al., "Destabilizing Universal Linkers for Signal Amplification in Self-Lighting Probes for RNA" *J. Am. Chem. Soc.* (2004) 126:13980:13986.

(Continued)

*Primary Examiner* — Narayan K Bhat

(74) *Attorney, Agent, or Firm* — Morgan, Lewis & Bockius LLP; Robin M. Silva

(57) ABSTRACT

The present invention generally relates to devices and methods for collecting and stabilizing biological samples, and more particularly, for collecting and stabilizing blood or other bodily fluids from a user's fingertip, earlobe, heel or other locations. The present invention also relates to sample collection devices that simplify the process for mixing the biological samples with an additive or additives, provide for efficient storage and safe transport of the samples, and provide for easy access to the samples for subsequent processing.

30 Claims, 29 Drawing Sheets

Specification includes a Sequence Listing.

(56) References Cited

U.S. PATENT DOCUMENTS

| | | | |
|---|---|---|---|
| 2004/0110134 | A1 | 6/2004 | Wenz et al. |
| 2004/0214196 | A1 | 10/2004 | Aydin |
| 2004/0235005 | A1 | 11/2004 | Friedlander et al. |
| 2004/0235154 | A1 | 11/2004 | Oh et al. |
| 2004/0259102 | A1 | 12/2004 | Kool |
| 2004/0259105 | A1 | 12/2004 | Fan et al. |
| 2005/0142545 | A1 | 6/2005 | Conn et al. |
| 2005/0208503 | A1 | 9/2005 | Yowanto et al. |
| 2005/0208543 | A1 | 9/2005 | Vann et al. |
| 2005/0272071 | A1 | 12/2005 | Lao et al. |
| 2006/0003351 | A1 | 1/2006 | Karger et al. |
| 2006/0063163 | A1 | 3/2006 | Chen et al. |
| 2006/0068378 | A1 | 3/2006 | Mirkin et al. |
| 2006/0199192 | A1 | 9/2006 | Kool et al. |
| 2008/0124810 | A1 | 5/2008 | Terbrueggen |
| 2008/0196517 | A1* | 8/2008 | Harvey ............... B01L 3/5023 73/864.91 |
| 2010/0267585 | A1 | 10/2010 | Terbrueggen |
| 2010/0285572 | A1 | 11/2010 | Salter et al. |
| 2011/0306512 | A1 | 12/2011 | Bankaitis-Davis et al. |
| 2013/0005594 | A1 | 1/2013 | Terbrueggen et al. |
| 2013/0337439 | A1 | 12/2013 | Goncalves Pereira Nobre et al. |
| 2015/0056716 | A1* | 2/2015 | Oyler ............... A61B 10/0051 436/176 |

FOREIGN PATENT DOCUMENTS

| | | | |
|---|---|---|---|
| EP | | 1024354 A1 | 8/2000 |
| EP | | 1130113 A1 | 9/2001 |
| EP | | 1167968 | 1/2002 |
| EP | | 1475152 A1 | 11/2004 |
| JP | | 2000-74906 | 3/2000 |
| JP | | 2010-525330 | 7/2010 |
| WO | WO 1989/012696 | | 12/1989 |
| WO | WO 1990/001069 | | 2/1990 |
| WO | WO 1992/003576 | | 3/1992 |
| WO | WO 1992/020702 | | 11/1992 |
| WO | WO 1994/024143 | | 10/1994 |
| WO | WO 1994/029485 | | 12/1994 |
| WO | WO 1995/015971 | | 6/1995 |
| WO | WO 1995/025948 | | 9/1995 |
| WO | WO 1996/015271 | | 5/1996 |
| WO | WO 1996/035699 | | 11/1996 |
| WO | WO 1996/040712 | | 12/1996 |
| WO | WO 1997/031256 | | 8/1997 |
| WO | WO 1997/046568 | | 12/1997 |
| WO | WO 1998/020162 | | 5/1998 |
| WO | WO 1999/037819 | | 7/1999 |
| WO | WO 2000/060348 | | 10/2000 |
| WO | WO 2001/027326 | | 4/2001 |
| WO | WO 2001/092579 | | 12/2001 |
| WO | WO 2001/094638 | | 12/2001 |
| WO | WO 2002/002823 | | 1/2002 |
| WO | WO 2004/005545 | | 1/2004 |
| WO | WO 2004/076692 | | 9/2004 |
| WO | WO 2005/124347 | | 12/2005 |
| WO | WO 2007/133703 | | 11/2007 |
| WO | WO 2008/131033 | | 10/2008 |
| WO | WO 2010/114599 | | 10/2010 |
| WO | WO 2015/191777 | | 12/2015 |

OTHER PUBLICATIONS

Abe et al., "Flow cytometric detection of specific RNAS in native human cells with quenched autoligating FRET probes" *Proc. Natl. Acad. Sci. USA* (2006) 103(2):263-8.
Abramson et al., "Nucleic acid amplification technologies" *Current Opinion in Biotechnology* (1993) 4:41-47.
Arar et al., "Synthesis and Antiviral Activity of Peptide-Oligonucleotide Conjugates Prepared by Using $N_\alpha$ (Bromoacetyl) peptides" *BioConj. Chem.* (1995) 6:573.
Bachmann et al., "Improvement of PCR amplified DNA sequencing with the aid of detergents" *Nucleic Acid Res.* (1990) 18:1309.
Backes et al., "An Alkanesulfonamide 'Safety-Catch' Linker for Solid-Phase Synthesis" *J. Org. Chem.* (1999) 64:2322-2330.
Baselt, D.R. et al., "A Biosensor Based on Magnetoresistance Technology", *Biosensors & Bioelectronics*, (1998) 13:731-739.
Beaucage et al., "The Functionalization of Oligonucleotides Via Phosphoramidite Derivatives" *Tetrahedron* (1993) 49(10):1925.
Bibikova, M. et al., "Quantitative Gene Expression Profiling in Formalin-Fixed, Paraffin-Embedded Tissues Using Universal Bead Arrays", *American Journal of Pathology*, (2004) 165:5 1799-1807.
Botti et al., "Chemical Synthesis of Proteins and Circular Peptides Using $N^\alpha$-1(1-Phenyl-2-Mercaptoethyl) Auxiliaries" *Protein Pept. Lett.* (2005) 12(8):729-35.
Brill et al., "Synthesis of Oligodeoxynucleoside Phosphorodithioates via Thioamidites" *J. Am. Chem. Soc.* (1989) 111:2321.
Carlsson et al., "Screening for genetic mutations" *Nature* (1996) 380:207.
Castiglioni et al., "Development of a Universal Microarray Based on the Ligation Detection Reaction and 16S rRNA Gene Polymorphism to Target Diversity of Cyanobacteria", Applied and Environmental Microbiology, vol. 70, No. 12, pp. 7161-7172 (2004).
Chan et al., "Construction and Characterization of a Heterodimeric Iron Protein: Defining Roles for Adenosine Triphosphate in Nitrogenase Catalysis" *Biochemistry* (2000) 39(24):7221-8.
Cuppoletti et al., "Oligomeric Fluorescent Labels for DNA" *Bioconjug. Chem.* (2005) 16(3):528-34.
Dempcy et al., "Synthesis of a thymidyl pentamer of deoxyribonucleic guanidine and binding studies with DNA homopolynucleotides" *Proc. Natl. Acad. Sci. USA* (1995) 92:6097.
Dill, K. et al., "Immunoassays and Sequence-Specific DNA Detection on a Microchip Using Enzyme Amplified Electrochemical Detection", *J. Biochem. Biophys. Methods*, (2004) 59:181-187.
Dogan et al., "5'-Tethered Stilbene Derivatives as Fidelity-and Affinity-Enhancing Modulators of DNA Duplex Stability" *J. Am. Chem. Soc.* (2004) 126:4762-4763.
Dose et al., "Convergent Synthesis of Peptide Nucleic Acids by Native Chemical Ligation", *Org. Letters* (2005) 7:20 4365-4368.
Dose et al., "Reducing Product Inhibition in DNA-Template-Controlled Ligation Reactions", *Agnew. Chem. Int. Ed.* (2006) 45:5369-5373.
Egholm, M. et al., "Peptide Nucleic Acids (PNA). Oligonucleotide Analogues with an Achiral Peptide Backbone" *J. Am. Chem. Soc.* (1992) 114:1895.
Egholm, M. et al. "PNA Hybridizes to Complementary Oligonucleotides Obeying the Watson-Crick Hydrogen-Bonding Rules", *Nature*, (1993) 365:566-568.
Fan, JB et al., "A Versatile Assay for High-Throughput Gene Expression Profiling on Universal Array Matrices", *Genome Research*, (2004) 14, 878-885.
Ficht et al., "Single-Nucleotide-Specific PNA-Peptide Ligation on Synthetic and PCR DNA Templates", *J. Am. Chem. Soc.* (2004) 126:9970-9981.
Ficht et al. "As Fast and Selective as Enzymatic Ligations: Unpaired Nucleobases Increase the Selectivity of DNA-Controlled Native Chemical PNA Ligation" *ChemBioChem* (2005) 6:2098-2103.
Foss, R.D. et al., "Effects of Fixative and Fixation Time on the Extraction and Polymerase Chain Reaction Amplification of RNA from Paraffin-Embedded Tissue. Comparison of Two Housekeeping Gene mRNA Controls", *Diagn. Mol. Pathol.*, 3(3):148-155 (1994).
Gottesfeld, J.M. et al., "Sequence-specific Recognition of DNA in the Nucleosome by Pyrrole-Imidazole Polyamides" *J. Mol. Biol.* (2001) 309:615-629.
Grossman et al., "High-Density Multiplex Detection of Nucleic Acid Sequences: Oligonucleotide Ligation Assay and Sequence-Coded Separation", *Nucleic Acids Research*, Oxford University Press, Surrey, Great Britain, vol. 22, No. 21, pp. 4527-4534 (1994).
Grossmann et al., "DNA-Catalyzed Transfer of a Reporter Group" *J. Am. Chem. Soc.* (2006) 128:15596-15597.
Gryaznov, S.M. and Letsinger, R.L., "Template controlled coupling and recombination of oligonucleotide blocks containing thiophosphoryl groups" *Nucleic Acids Research* (1993) 21:1403.
Gryaznov et al., "Chemical Ligation of Oligonucleotides in the Presence and Absence of Template", *J. Am. Chem. Soc.*, (1993) 115(9):3808-3809.

(56) References Cited

OTHER PUBLICATIONS

Gryaznov et al., "Enhancement of Selectivity in Recognition of Nucleic Acids via Chemical Autoligation", *Nucleic Acids Res.*, (1994) 22:2366-2369.

Herrlein and Letsinger, "A Covalent Lock for Self-Assembled Oligonucleotide Conjugates", *J. Am. Chem. Soc.*, (1995) 117:10151-10152.

Horn et al., "Oligonucleotides with Alternating Anionic and Cationic Phosphoramidate Linkages: Synthesis and Hybridization of Sterio-uniform Isomers", *Tetrahedron Letters* (1996) 37:743.

Jeffs et al., "Unusual conformation of a 3'-thioformacetal linkage in a DNA duplex" *J. Biomolecular NMR* (1994) 34:17.

Jenkins et al., "The Biosynthesis of Carbocyclic Nucleosides" *Chem. Soc. Rev.* (1995) pp. 169-176.

Karim et al., "Convenient genotyping of six myostatin mutation causeing double-muscling in cattle using a multiplex oligonucleotide ligation assay", *Animal Genetics*, vol. 31, No. 6, pp. 396-399 (2000).

Kenner, G.W., "The Safety Catch Principle in Solid Phase Peptide Synthesis", *J. Chem. Soc.* (1971) pp. 636-637.

Kiedrowski et al., "Parabolic Growth of a Self-Replicating Hexadeoxynucleotide Bearing a 3'5'-Phosphoamidate Linkage" *Agnew. Chem. Intl. Ed.* English (1991) 30:423.

Kool, E.T. et al., "Convergent DNA synthesis: a non-enzymatic dimerization approach to circular oligodeoxynucleotides" *Nucleic Acid Res.* (1995) 23 (17):3547.

Koshkin et al., "LNA (Locked Nucleic Acid): An RNA Mimic Forming Exceeingly Stable LNA:LNA Duplexes" *J. Am. Chem. Soc.* (1998) 120:13252-3.

Koshkin et al., "LNA (Locked Nucleic Acids): Synthesis of the Adenine, Cytosine, Guanine, 5-Methylcytosine, Thymine and Uracil Bicyclonucleoside Monomers, Oligomerisation, and Unprecedented Nucleic Acid Recognition" *Tetrahedron* (1998) 54:3607-3630.

Kutyavin et al., "Oligonucleotides with conjugated dihydropyrroloindole tripeptides: base composition and backbone effects on hybridization" *Nucleic Acids Research* (1997) vol. 25, No. 18: 3718-3723.

Kutyavin et al., "3'-Minor groove binder-DNA probes increase sequence specificity at PCR extension temperatures" *Nucleic Acids Research* (2000) vol. 28, No. 2:655-661.

Landegren, U. "Ligation-based DNA Diagnostics" *Bioessays* (1993) 15(11):761-5.

Landegren, U. et al., "A Ligase-Mediated Gene Detection Technique", *Science*, (1988) 241(4689):1077-1080.

Letsinger et al., "Phosphoramidate Analogs of Oligonucleotides" *J. Org. Chem.* (1970) 35:3800.

Letsinger et al., *Nucl. Acids Res.* (1986) 14:3487.

Letsinger et al., "Cationic Oligonucleotides" *J. Am. Chem. Soc.* (1988) 110:4470.

Letsinger et al., "Hybridization of Alternating Cationic/Anionic Oligonucleotides to RNA Segments", *Nucleotide and Nucleoside* (1994) 13:1597.

Liu, R. et al., "Fully Integrated Miniature Device for Automated Gene Expression DNA Microarray Processing", *Anal. Chem.*, (2006) 78(6):1980-1986.

Luebke and Dervan, "Nonenzymatic Sequence-Specific Ligation of Double-Helical DNA", *J. Am. Chem. Soc.*, (1991) 113:7447-7448.

Luebke, K.J. and Dervan, P.B., "Nonenzymatic Ligation of Oligodeoxyribonucleotides no a Duplex DNA Template by Triple-Helix Formation", *J. Am. Chem. Soc.* (1989) 111:8733.

Mag et al., "Synthesis and selective cleavage of an oligodeoxynucleotide containing a bridged internucleotide 5'-phosphorothioate linkage", *Nucleic Acids Res.* (1991) 19:1437-1441.

Marshall et al., "DNA Chips: An Array of Possibilities", *Nat Biotechnol.* (1998) 16(1):27-31.

Martel et al., (High Throughput Genomics) "Multiplex Screening Assay for mRNA Combining Nuclease Protection with Luminescent Array Detection," *Assay and Drug Development Technologies* 1:61-71 (2002).

Meier et al., "Peptide Nucleic Acids (PNAs)—Unusual Properties of Nonionic Oligonucleotide Analogues" *Chem. Int. Ed. Engl.* (1992) 31:1008.

Mesmaeker et al., "Comparison of Rigid and Flexible Backbones in Antisense Oligonucleotides", *Bioorganic & Medicinal Chem. Lett.* (1994) 4:395.

Metelev, V.G. et al., "Oligodeoxyribonucleotides With Internucleotidic or Terminal Phosphorothioate Groups: Different Pathways in the Reaction with Water-Soluble Carbodimide", *Nucleosides & Nucleotides* (1999) 18:2711.

Miller, G.P. et al., "New, stronger nucleophiles for nucleic acid-templated chemistry: Synthesis and application in fluorescence detection of cellular RNA", *Bioorganic and Medicinal Chemistry* (2008) 16:56-64.

Moran et al., "A thymidine triphospate shape analog lacking Watson-Crick pairing ability is replicated with high sequence selectivity", *Proc. Natl. Acad. Sci. USA* (1997) 94(20):10506-11.

Narayanan et al., "Clamping down on weak terminal base pairs: oligonucleotides with molecular caps as fidelity-enhancing elements at the 5'- and 3'-terminal residues", *Nucleic Acids Research* (2004) 32:2901-2911.

Nickerson, "Gene probe assays and their detection", *Current Opinion in Biotechnology* (1993) 4:48-51.

Nilsson, M. et al., "RNA-Templated DNA Litigation for Transcript Analysis", *Nucleic Acids Research*, 29:2 578-581 (2001).

Offer et al., "Extending Synthetic Access to Proteins with a Removable Acyl Transfer Auxiliary", *J. Am. Chem. Soc.* (2002) 124(17):4642-6.

Ollivier et al., "Fmoc Solid-Phase Synthesis of Peptide Thioesters Using an Intramolecular N,S-Acyl Shift" *Organic Letters* (2005) vol. 7, No. 13, pp. 2647-2650.

Pauwels et al., "Biological Activity of New 2-5A Analogues", *Chemica Scripta* (1986) 26:141.

Pooga, M. et al., "PNA oligomers as tools for specific modulation of gene expression", *Biomolecular Engineering* (2001) 17:183-192.

Pritchard et al., "Effects of Base Mismatches on Joining of Short Oligonucleotides by DNA Ligases", *Nucleic Acids Res.* (1997) 25(17):3403-7.

Rawls, R., "Optimistic About Antisense" *C & E News* (Jun. 2, 1997), p. 35-39.

Sando et al., "Nonenzymatic DNA ligation in *Escherichia coli* cells", *Nucleic Acids Res. Suppl.* (2002) 2:121-2.

Sando et al., "Quencher as Leaving Group: Efficient Detection of DNA-Joining Reactions", *J. Am. Chem. Soc.* (2002) 124(10)2096-7.

Sando et al., "Imaging of RNA in Bacteria with Self-Ligating Quenched Probes", *Journal Am. Chem.* (2002) 124(33):9686-7.

Sando et al., "Quenched Auto-Ligating DNAs: Multicolor Identification of Nucleic Acids at Single Nucleotide Resolution", *J. Am. Chem. Soc.* (2004) 126(4):1081-7.

Sawai et al., "Synthesis and Properties of Oligoadenylic Acids Contaiing 2'-5' Phosphoramide Linkage", *Chem. Lett.* (1984) 805.

Schafer et al., "DNA variation and the future of human genetics", *Nature Biotechnology* (1993) 16:33-39.

Schouten et al., "Relative quantification of 40 nucleic acid sequences by multiplex ligation-dependent probe amplification", *Nucleic Acid Research*, Oxford University Press, Great Britain, vol. 30, No. 12 (2002).

Shabarova, Z.A., et al., "Chemical ligation of DNA: the first non-enzymatic assembly of a biologically active gene", *Nucleic Acids Research* (1991) 19:4247.

Shanghvi, Y.S. and Cook, Dan (Ed.) "ASC Symposium Series 580", Chapters 2, 3, 6, and 7 (1994).

Silverman et al., "Quenched autoligation probes allow discrimination of live bacterial species by single nucleotide differences in rRNA", *Nucleic Acids Res.* (2005) 33(15):4978-86.

Silverman et al., "Detecting RNA and DNA with Templated Chemical Reactions", *Chem. Rev.*, (2006) 106:3775-3789.

Sprinzl et al., "Enzymatic Incorporation of ATP and CTP Analogues into the 3' End of Trna", *Eur. J. Biochem.* (1977) 81:579.

Steemers, F.J. et al., "Screening Unlabeled DNA Targets with Randomly Ordered Fiber-Optic Gene Arrays", *Nat Biotechnol.* (2000) 18(1):91-4.

(56) References Cited

OTHER PUBLICATIONS

Stern et al., "Multiplex ligation-dependent probe amplification using a completely synthetic probe set", *Biotechniques*, vol. 37, No. 3, pp. 399-405 (2004).

Stetsenko and Gait, "Efficient Conjugation of Peptides to Oligonucleotides by 'Native Ligation'", *J. Org. Chem.* (2000) 65(16):4900-8.

Ueno, Y. et al., "Nucleosides and Nucleotides. 165. Chemical Ligation of Oligodeoxynuclotides Having a Mercapto Group at the 5-Position of 2'-Deoxyuridine Via a Disulfide Bond" Nucleosides and Nucleotides, Marcel Dekker Inc., vol. 17, No. 1-3 (1998) pp. 283-289.

Umek, R.M. et al., "Electronic Detection of Nucleic Acids—A Versatile Platform for Molecular Diagnostics", *J. Molecular Diagnostics*, (2001) 3:74-84.

Van Eijk, M.J.T., "SNPWaveTM: a flexible multiplexed SNP genotyping technology", *Nucleic Acids Research*, vol. 32, No. 4 (2004).

Van't Veer, L.J., et al., "Gene Expression Profiling Predicts Clinical Outcome of Breast Cancer", *Nature*, (2002) 415(6871):530-536 (2002).

Wahlestedt C. et al., "Potent and nontoxic antisense oligonucleotides containing locked nucleic acids", *PNAS* (2000) 97:5633-5638.

Wang et al., "Large-Scale Identification, Mapping, and Genotyping of Single-Nucleotide Polymorphisms in the Human Genome", *Science* (1998) 280:1077.

Warren et al., "Toward Fully Synthetic Glycoproteins by Ultimately Convergent Routs: A Solution to a Long-Standing Problem", *J. Am. Chem. Soc.* (2004) 126(21):6576-82.

Weizmann, Y. et al., "Magneto-Mechanical Detection of Nucleic Acids and Telomerase Activity in Cancer Cells", *J. Am. Chem. Soc.*, (2004) 126:1073-1080.

Wengel, J. et al., "LNA (Locked Nucleic Acid)", *Nucleosides & Nucleotides*, (1999) 18:1365-1370.

Wu, D.Y. et al., "The Ligation Amplification Reaction (LAR)-Amplification of Specific DNA Sequences Using Sequential Rounds of Template-Dependent Ligation", *Genomics* (1989) 4(4):560-9.

Xu et al., "Chemical and enzymatic properties of bridging 5'-S-phosphorothioester linkages in DNA", *Nucleic Acid Res.* (1998) 26(13):3159-64.

Xu et al., "Nonenzymatic Autoligation in Direct Three-Color Detection of RNA and DNA Point Mutations" *Nature Biotechnology* (2001) 19(2):148-52.

Xu and Kool, E.T., "A Novel 5'-Iodonucleoside Allows Efficient Nonenzymatic Ligation of Single-stranded and Duplex DNAs", *Tetrahedron Letters* (1997) 38:5595.

Xu and Kool, E.T., "High sequence fidelity in a non-enzymatic DNA autoligation reacation", *Nucleic Acid Research* (1999) 27:875.

Yang et al., "Badge, Beads Array for the Detection of Gene Expression, a High Throughput Diagnostic Bioassay", *Genome Research* (2001) 11(11):1888-98.

Yeakley, JM et al., "Profiling Alternative Splicing on Fiber-Optic Arrays", *Nature Biotechnology*, (2002) 20:353-358.

\* cited by examiner

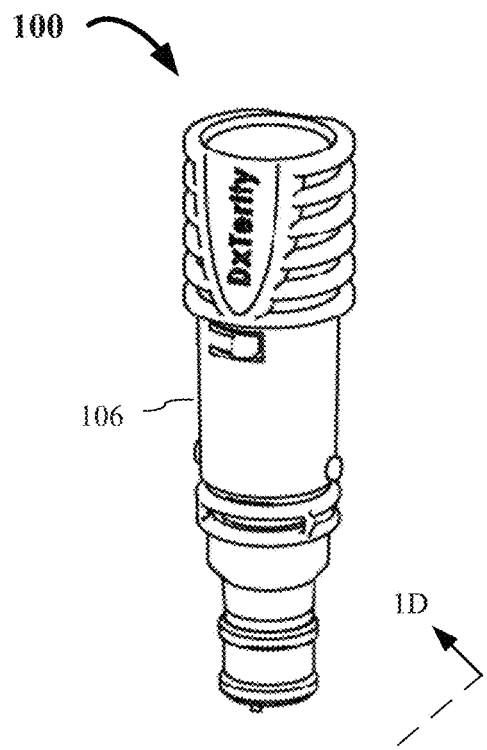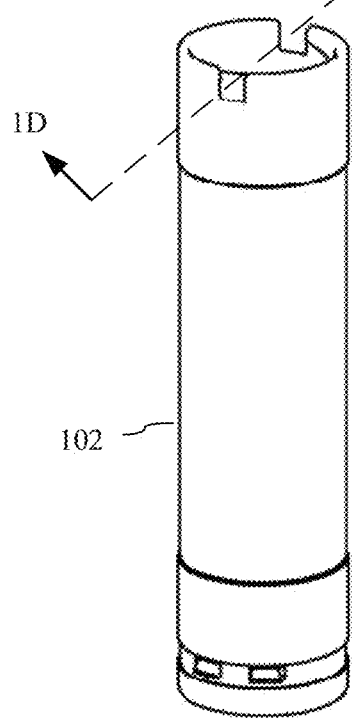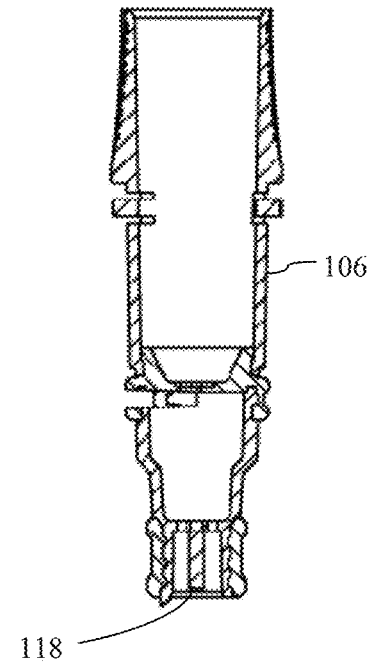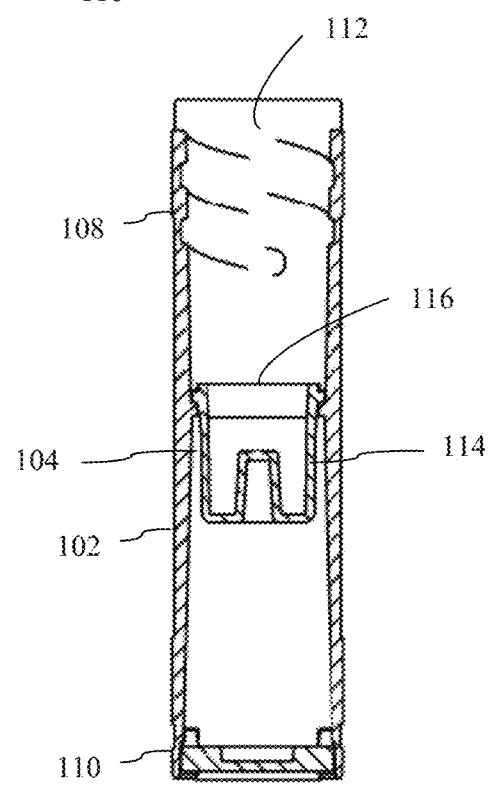
FIG. 1C
FIG. 1D

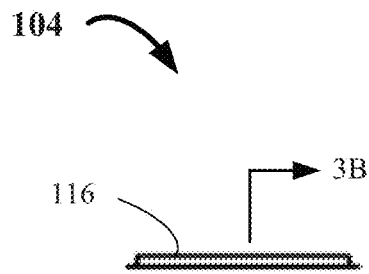
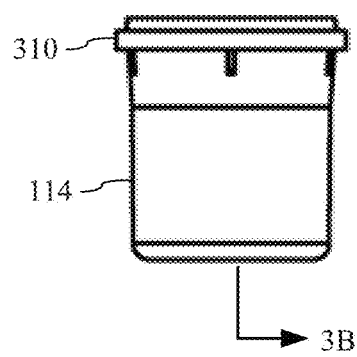
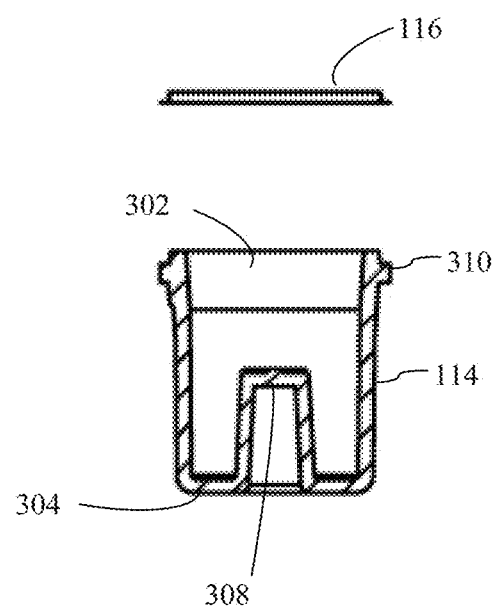
FIG. 3A
FIG. 3B
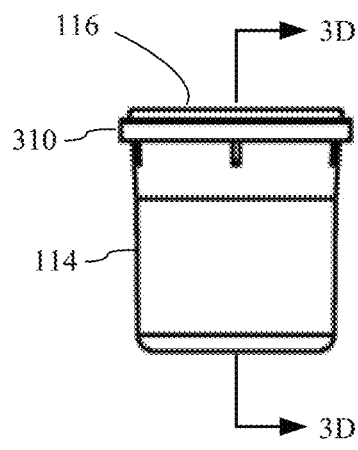
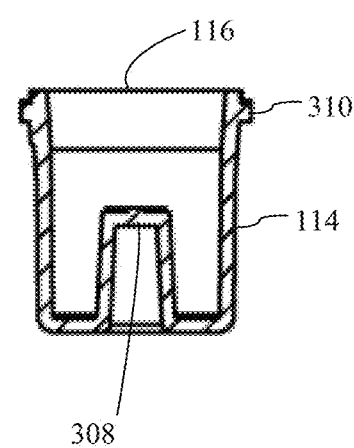
FIG. 3C
FIG. 3D

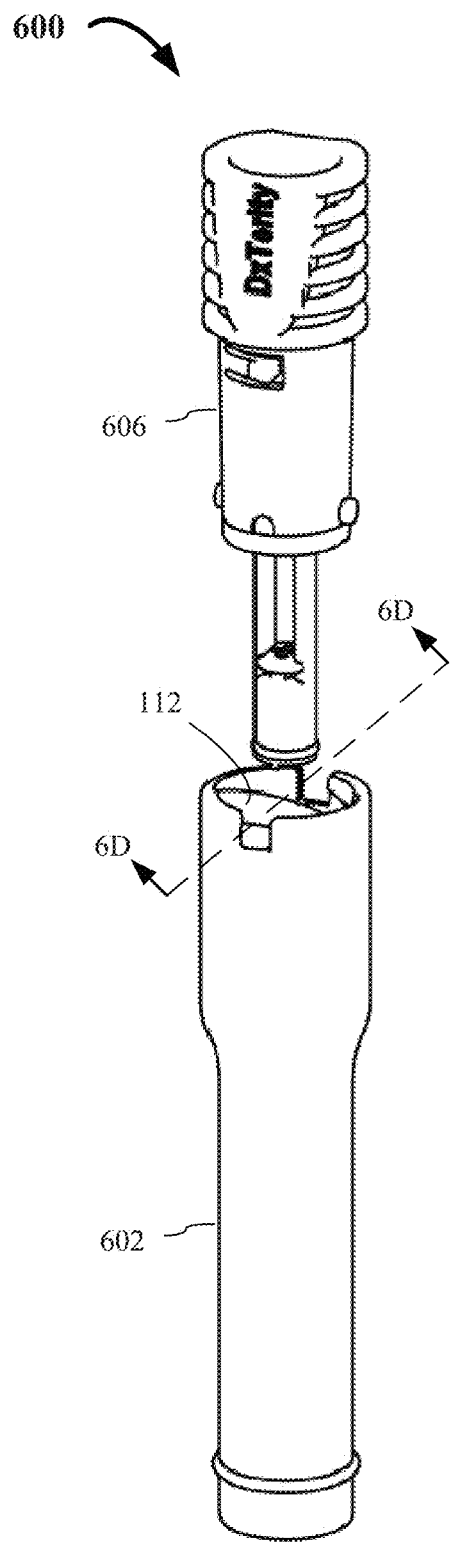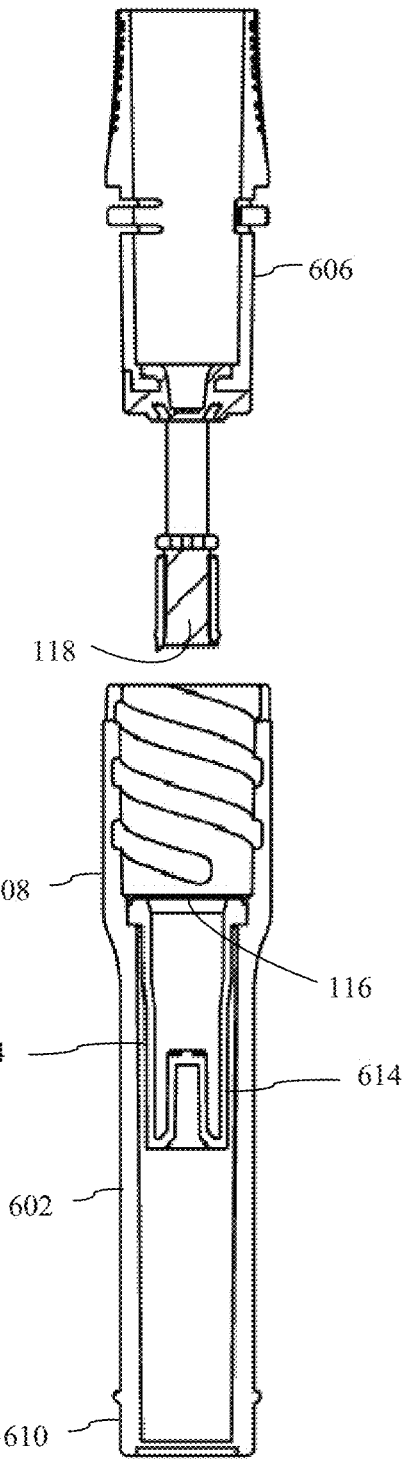
FIG. 6C                  FIG. 6D

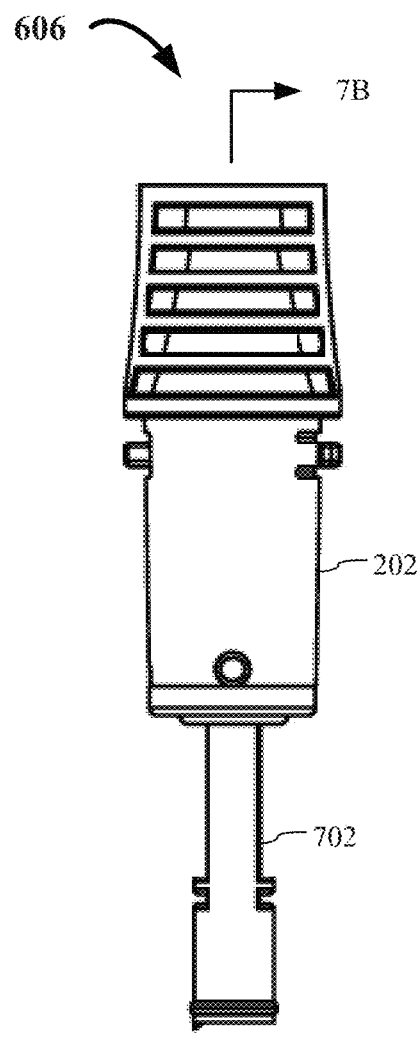
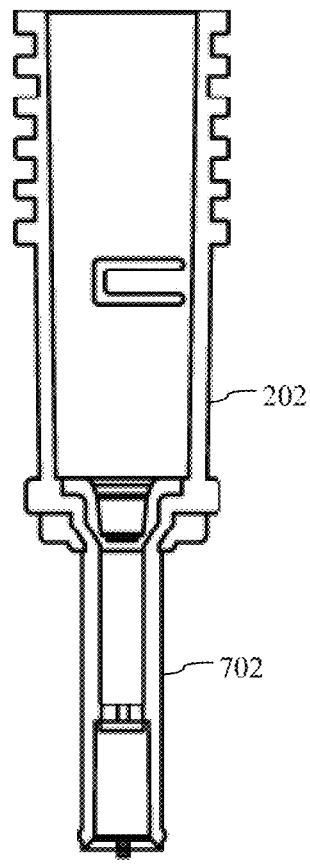
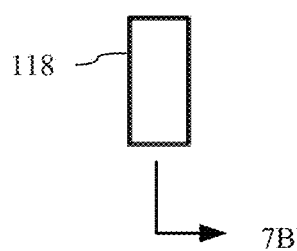
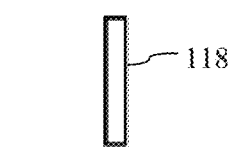
FIG. 7A                    FIG. 7B

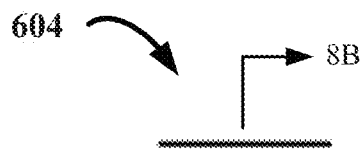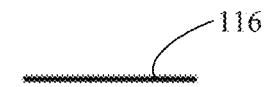
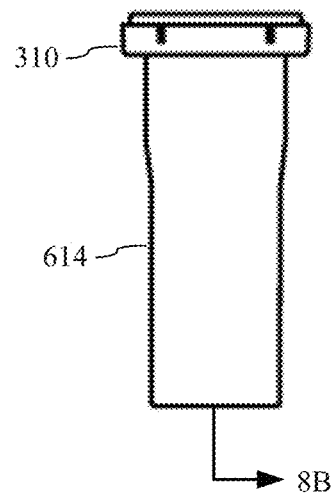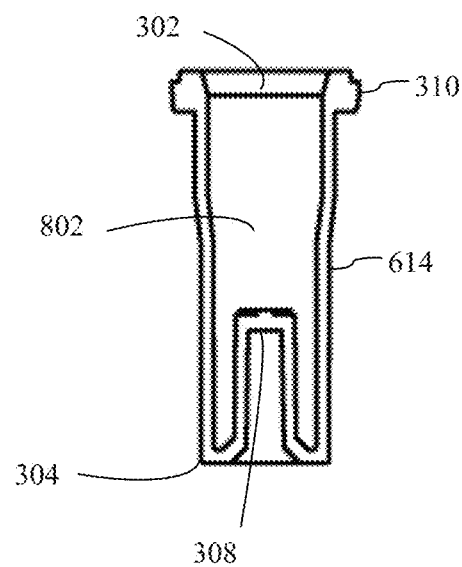
FIG. 8A    FIG. 8B
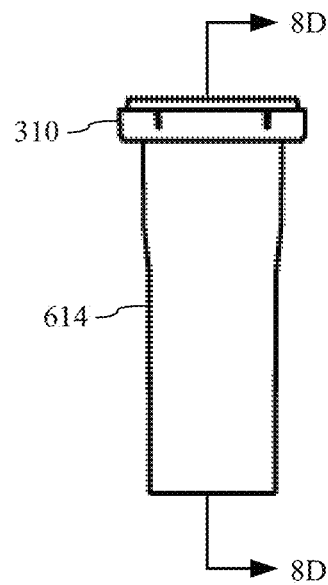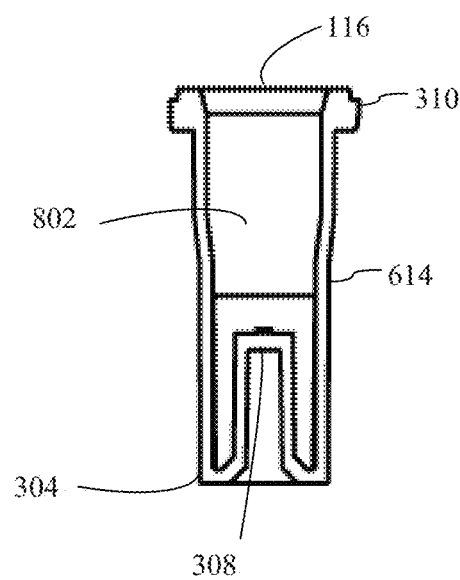
FIG. 8C    FIG. 8D

DEVICES AND METHODS FOR COLLECTING AND STABILIZING BIOLOGICAL SAMPLES

CROSS-REFERENCE TO RELATED APPLICATIONS

This application is a Continuation of U.S. patent application Ser. No. 14/736,220 filed Jun. 10, 2015, now U.S. Pat. No. 9,757,095, which claims priority of U.S. Provisional Patent Application No. 62/010,314 filed Jun. 10, 2014; all are incorporated by reference in their entireties for all purposes.

REFERENCE TO A "SEQUENCE LISTING," A TABLE, OR A COMPUTER PROGRAM LISTING APPENDIX SUBMITTED ON A COMPACT DISK

The sequence listing contained in the file named "068433-5004-US01_SEQ_CRF", created on Sep. 7, 2017 and having a size of 9.96 kilobytes, has been submitted electronically herewith via EFS-Web, and the contents of the txt file are hereby incorporated by reference in their entirety.

FIELD OF THE INVENTION

The present invention generally relates to devices and methods for collecting and stabilizing biological samples, and more particularly, for collecting and stabilizing blood or other bodily fluids from a user's fingertip, earlobe, heel or other locations. The present invention also relates to sample collection devices that simplify the process for mixing the biological samples with an additive or additives, provide for efficient storage and safe transport of the samples, and provide for easy access to the samples for subsequent processing.

BACKGROUND

The collection of a biological fluid sample (blood, saliva, urine, etc) from a patient is the first step in many diagnostic procedures. Pre-evacuated collection tubes designed for venous collection of blood samples are commonly used devices, and several companies sell a broad portfolio of blood collection tubes pre-filled with additives like Heparin, EDTA, and nucleic acid stabilization agents to facilitate downstream testing processes. Problems associated with venous collection products are the requirement for trained individuals to assist the patient in the collection of the sample, risks associated with puncturing a vein with a needle, and the collection of substantially more patient sample than is needed to perform a diagnostic test.

Capillary tube based collection devices are used to collect a small volume of blood from a patient's fingertip or heel. These devices usually function by holding the tip of an open end capillary tube against the drop of fluid and the fluid is then drawn into the tube using capillary forces. Alternative collection methods include dripping of a patient's sample onto a piece of paper or into a collection container. Microneedle based evacuated devices are also in development. Similar to evacuated tubes, these devices are often coated with additives to facilitate future diagnostic testing or improved sample handling. In some instances, the biological fluid is dispensed into a secondary container when it can be mixed with additive and/or stored until later use.

Furthermore, there is a growing demand for blood samples for molecular diagnostic tests that require immediate stabilization of the genomic material at the time of collection. Proper stabilization usually requires immediate mixing of the blood with a stabilization buffer within a defined ratio of blood to buffer. Current devices are not designed for this application.

Given the above background, there is a need in the art for collection devices and methods that enable simplified collection of biological samples and facility the mixing of the biological samples with additives that aid in the stabilization and future processing of the samples.

The information disclosed in this Background section is only for enhancement of understanding of the general background of the invention and should not be taken as an acknowledgement or any form of suggestion that this information forms the prior art already known to a person skilled in the art.

SUMMARY

Various aspects of the present invention provide novel devices and kits that enable simplified collection of a biological sample and facilitate the mixing of the biological sample with a solution or additives that aid in the stabilization and future processing of the biological sample. In some embodiments, the devices of the present invention are designed for easy handling by the end user (e.g., a patient) or medical personnel, and for integration with standard automation and testing systems that are employed in subsequent processing (e.g., diagnostic testing laboratories).

In one aspect, the present invention provides a collection and stabilization device with a collector for collecting a biological sample. In a preferred embodiment, the collector includes an absorbent member for collecting the biological sample. In another preferred embodiment, the collector is configured to function as a handle for easy gripping of the collector while taking the biological sample. In still another preferred embodiment, the collector is configured to serve as a cap that sealingly engages with a housing, facilitating safe transportation of the sample. In some embodiments, the collector is configured to be interlocked with the housing once it is fully engaged with the housing, prohibiting unintentional removal of the collector from the housing. In some embodiment, the collector is provided with a penetrable or pierceable septum that seals the biological sample in the collector. The penetrable or pierceable septum allows the access to the biological sample for subsequent processing without removing the collector from the housing.

In another aspect, the present invention provides a collection and stabilization device with a retainer for storing a solution, additives, reagents or the like that aid in the stabilization and future processing of the biological sample. In a preferred embodiment, the retainer is manufactured separately and pre-assembled with the housing prior to the use of the device. The collector, retainer and housing are configured such that when the collector is engaging or engaged with the housing, the collector propels the solution (or additives, reagents, etc.) stored in the retainer to flow through the absorbent member, releasing the biological sample and mixing with the biological sample.

Various other aspects of the present invention provide methods to use the novel devices and kits to collect and stabilize biological samples. In some embodiments, a method of the present invention includes (i) collecting a biological sample using the collector and (ii) inserting the collector into the housing. In some embodiments, the method further includes (iii) transporting or shipping the collector along with the housing to a receiver such as a testing lab for subsequent processing.

The methods and apparatuses of the present invention have other features and advantages which will be apparent from or are set forth in more detail in the accompanying drawings, which are incorporated herein, and the following Detailed Description, which together serve to explain certain principles of the present invention.

Accordingly, the present invention provides devices for collecting and stabilizing a biological sample, the device comprising:
 (a) a housing comprising an open end portion, an closed end portion, and an interior space;
 (b) a retainer insertable into the interior space of the housing, the retainer comprising a vessel for receiving a solution and a penetrable seal for enclosing the solution within the vessel;
 (c) a collector removably engagable with the open end portion of the housing and capable of sealingly closing the open end portion of the housing, the collector comprising an absorbent member for collecting the biological sample,
 wherein, when the collector is engaged with the open end portion of the housing, the absorbent member is received in the housing and the collector breaks the penetrable seal of the retainer that has been inserted into the interior space of the housing and propels the solution to flow through the absorbent member, thereby releasing the biological sample from the absorbent member and facilitating mixing of the biological sample with the solution.

In an additional aspect, the collector comprises:
 (a) a body portion serving as a handle when taking the biological sample and as a seal when engaging or engaged with the open end portion of the housing; and
 (b) a stem portion fixedly coupled with the body portion or monolithically formed with the body portion, wherein,
  (i) the stem portion comprises a first segment proximal to the body portion and a second segment distal to the body portion;
  (ii) the absorbent member is attached to the second segment of the stem portion; and
  (iii) when the collector is engaged with the open end portion of the housing, the absorbent member and at least a portion of the second segment are received in the retainer.

In a further aspect, the collector further comprises a plasma membrane for generating plasma from the biological sample, wherein the plasma membrane is disposed within the second segment of the stem portion.

In an additional aspect, the body portion and the stem portion are made of a plastic, a thermoplastic, or a metal. In a further aspect, the body portion and the stem portion are made of an inert thermoplastic, such as a material comprising polycarbonate, polyethylene terephthalate, polyurethane, or medical grade polypropylene.

In a further aspect, the body portion and the stem portion are substantially cylindrical;
 the body portion has a length between 2 cm and 8 cm, and an average nominal diameter between 1 cm and 3 cm; and
 the stem portion has a length between 1 cm and 5 cm, and an average nominal diameter between 0.5 cm and 2.5 cm.

In an additional aspect the first segment is formed with one or more open slots to allow the released biological sample and the propelled solution flow through; and
 the second segment distal to the body portion is formed with a cavity for accommodating the absorbent member.

In an additional aspect, the collector further comprises a plasma membrane for generating plasma from the biological sample, wherein the plasma membrane is disposed within the cavity.

In a further aspect, the stem portion further comprises:
 (c) a partition disposed between the first segment and the second segment for preventing the absorbent member from being pushed into the second segment when the collector is engaging or engaged with the open end portion of the housing, wherein the partition is formed with at least one hole or slot through which the first segment is in fluidic communication with the second segment.

In a further aspect, the first segment proximal to the body portion is formed with a reservoir for facilitating mixing of the biological sample with the solution and accommodating the mixture of the biological sample and the solution; and
 the second segment distal to the body portion is formed with a cavity for accommodating the absorbent member.

In a further aspect, the collector further comprises a plasma membrane for generating plasma from the biological sample, wherein the plasma membrane is disposed within the cavity.

In a further aspect, the reservoir formed in the first segment has a volume that is between 1 µL and 5000 µL, between 20 µL, and 2000 µL, or between 40 µL and 500 µL.

In a further aspect, the stem portion further comprises:
 (c) a partition disposed between the first segment and the second segment for preventing the absorbent member from being pushed into the second segment when the collector is engaging or engaged with the open end portion of the housing, wherein the partition is formed with at least one hole or slot through which the first segment is in fluidic communication with the second segment.

In a further aspect, the collector further comprises:
 (c) a penetrable septum for preventing the mixture of the biological sample and the solution from flowing out through the body portion.

In a further aspect, the penetrable septum is disposed within the body portion and adjacent to the stem portion.

In a further aspect, the penetrable septum is made of a material comprising vulcanized rubber, interwoven fabric, or a thermoplastic elastomer.

In a further aspect, the collector further comprises:
 a first elastomeric seal disposed on an exterior surface of the second segment of the stem portion, wherein the first elastomeric seal provides sealing between the exterior surface of the second segment of the stem portion and an interior surface of the retainer when the collector is engaging or engaged with the open end portion of the housing.

In a further aspect, the collector further comprises:
 a second elastomeric seal disposed on an exterior surface of the first segment of the stem portion or on an exterior surface of the body portion adjacent to the stem portion, wherein when the collector is engaging or engaged with the open end portion of the housing, the second elastomeric seal provides sealing between the exterior surface of the first segment of the stem portion and the interior surface of the housing, or provides sealing between the exterior surface of the body portion and the interior surface of the housing.

In a further aspect, the second elastomeric seal couples the body portion with the stem portion.

In a further aspect, the first elastomeric seal is made of a material comprising vulcanized rubber, interwoven fabric, or a thermoplastic elastomer.

In a further aspect, the second elastomeric seal is made of a material comprising vulcanized rubber, interwoven fabric, or a thermoplastic elastomer.

In a further aspect, the second segment of the stem portion includes a tooth protruded from an edge of the second segment of the stem portion to facilitate breaking the penetrable seal of the retainer when the collector is engaging or engaged with the open end portion of the housing.

In a further aspect, the second segment of the stem portion includes a rib formed circumferentially on an exterior surface of the second segment of the stem portion, the rib performing one or more of the following: (i) acting as a plunger to assist propelling the solution to flow through the absorbent member when the collector is engaging or engaged with the open end portion of the housing, and (ii) assisting in sealing between the second segment of the stem portion and the retainer.

In a further aspect, the body portion comprises one or more pins formed on a side wall of the body portion and proximal to the stem portion for screwing the collector to the housing.

In a further aspect, the body portion comprises two pins formed on a side wall of the body portion and proximal to the stem portion for screwing the collector to the housing, wherein the two pins are opposite to each other.

In a further aspect, the body portion comprises at least one detention on a side wall of the body portion; and the housing comprises at least one slot formed at the open end portion, wherein the at least one detention is received by the at least one slot when the collector is engaged with the housing, thereby preventing unintentional removal of the collector from the housing after the collector is engaged with the housing.

In a further aspect, the at least one detention comprises two clips formed on the side wall of the body portion and opposite to each other; and the at least one slot comprises two slot corresponding to the two clips.

In a further aspect, the body portion comprises an external grip formed on a side wall of the body portion and distal to the stem portion, thereby facilitating easy gripping of the collector when taking the biological sample and when engaging the collector with the housing.

In a further aspect, the external grip includes recesses, grooves, ribs, pins, protrusions, or combination thereof, formed on the side wall of the body portion.

In a further aspect, the body portion comprises a substantially flat or curvy surface formed on a side wall of the body portion for engraving, printing or molding a brand name on the flat surface. The device of claim 1, wherein the vessel has an open top and a closed bottom, and a central portion of the closed bottom is recessed inwardly toward the open top such that the central portion of the closed bottom compresses the absorbent member when the collector is engaging or engaged with the open end portion of the housing, thereby squeezing the biological sample out of the absorbent member.

In a further aspect, the vessel has an open top, a closed bottom, and a column protruded from a central portion of the closed bottom toward the open top such that the column of the closed bottom compresses the absorbent member when the collector is engaging or engaged with the open end portion of the housing, thereby squeezing the biological sample out of the absorbent member.

In a further aspect, the retainer further comprises a solution retention disposed between the solution received in the vessel and the penetrable seal.

In a further aspect, the vessel of the retainer is tapered with an open top wider than a closed bottom.

In a further aspect, the vessel of the retainer comprises a reservoir adjacent to the open top for facilitating mixing of the biological sample with the solution and accommodating the mixture of the biological sample and the solution.

In a further aspect, the housing comprises a first seat formed on an interior surface of the housing for supporting the retainer once the retainer is inserted into the interior space of the housing, and the vessel comprises a first flange formed on an exterior surface of the vessel of the retainer to abut the first shoulder.

In a further aspect, the first seat comprises a shoulder or a flange extruded radially inwardly from the interior surface of the housing;

the first flange extends radially outwardly from the exterior surface of the vessel of the retainer.

In a further aspect, the first seat comprises a plurality of ribs spaced apart circumferentially along the interior surface of the housing.

In a further aspect, the vessel comprises a second seat formed on an interior surface of the vessel for supporting the solution retention, and the solution retention comprises a second flange formed on an exterior surface of the solution retention to abut the second shoulder.

In a further aspect, the vessel of the retainer is made of a plastic, a thermoplastic, or a metal.

In a further aspect, the vessel of the retainer is made of a medical grade polypropylene.

In a further aspect, the vessel of the retainer has a volume that is between 20 µL and 2000 µL, between 50 µL and 1000 µL, or between 100 µL and 500 µL.

In a further aspect, the penetrable seal is made of a thermoplastic material, a foil coated thermoplastic material, a heat sealable material, or a material coated with a pressure sensitive adhesive.

In a further aspect, the penetrable seal is applied onto the vessel by heat

In a further aspect, the vessel of the retainer has a general cylindrical shape.

In a further aspect, the vessel of the retainer has a cross section that is substantially circular or polygonal.

In a further aspect, the open end portion of the housing are threaded with internal threads to facilitate engagement with the collector and/or insertion of the retainer.

In a further aspect, the closed end portion of the housing is formed with (i) a groove extended radially inwardly from an exterior surface of the closed end portion of the housing, (ii) a shoulder or flange extended radially outwardly from the exterior surface of the closed end portion of the housing, (iii) a recess at a bottom of the closed end portion of the housing, or (iv) combination thereof for retaining the housing in a rack when processed using a liquid handling robot.

In a further aspect, the opening end portion of the housing is formed with a locking means for interlocking with the collector.

In a further aspect, the locking means includes one or more slots formed at opening end portion of the housing.

In a further aspect, the housing has a generally cylindrical shape.

In a further aspect, the housing has a cross section that is substantially circular or polygonal.

In a further aspect, the housing is made of a material of a plastic, a thermoplastic, or a metal.

In a further aspect, the housing has a length between 4 cm and 12 cm, and an average nominal diameter between 1 cm and 4 cm.

In a further aspect, the devices further comprises one or more of the following: (i) a 2D Data Matrix Bar Code printed on or attached to a bottom of the housing or an exterior surface of the housing, (ii) a readable product identification printed on or attached to the bottom of the housing or the exterior surface of the housing, and (iii) a radio-frequency identification (RFID) tag printed on or attached to the bottom of the housing or the exterior surface of the housing.

In a further aspect, the absorbent member is made of a porous or wicking material.

In a further aspect, the absorbent member is a sponge.

In a further aspect, the absorbent member collects between 1 μL and 2000 μL, between 5 μL and 200 μL, or between 20 μL and 100 μL of the biological sample.

In a further aspect, the invention provides kits for health care, comprising:

(a) a collector comprising an absorbent member for collecting a biological sample;

(b) a housing comprising an open end portion, a closed end portion, and an interior space; and (c) a retainer insertable into the interior space of the housing, the retainer comprising a vessel for receiving a solution and a penetrable seal for enclosing the solution within the vessel, wherein, the collector is removably engagable with the open end portion of the housing and capable of sealingly closing the open end portion of the housing, and wherein, when the collector is engaged with the open end portion of the housing, the absorbent member is received in the housing and the collector breaks the penetrable seal of the retainer that has been inserted into the interior space of the housing and propels the solution to flow through the absorbent member, thereby releasing the biological sample from the absorbent member and facilitating mixing of the biological sample with the solution.

In an additional aspect, the kit further comprises a lancet for penetrating a membrane of an end user to release the biological sample.

In an additional aspect, the kit further comprises a casing for accommodating the collector, the housing and the retainer.

In an additional aspect, the kit further comprises further comprising a preparation pad for cleaning and preparing a collection site.

In an additional aspect, the preparation pad is a pre-prepared alcohol pad.

In an additional aspect, the kit is shipped to an end user with the retainer placed outside of the housing.

In an additional aspect, the kit is shipped to an end user with the retainer having been inserted into the housing.

In a further aspect, the invention provides methods for collecting and stabilizing a biological sample, the method comprising:

(a) providing a collector comprising an absorbent member, a housing, and a retainer insertable into the housing;

(b) collecting the biological sample by the absorbent member of the collector; and (c) sealingly engaging the collector with the housing, wherein, the sealingly engaging of the collector with the housing breaks a penetrable seal of the retainer that has been inserted into an interior space of the housing and propels a solution retained in the retainer to flow through the absorbent member, thereby releasing the biological sample from the absorbent member and facilitating mixing of the biological sample with the solution.

In an additional aspect, the method further comprises: penetrating a membrane of a user by a lancet to provide the biological sample.

In an additional aspect, the method further comprises cleaning and preparing a collection site prior to penetrating the membrane.

In an additional aspect, the method further comprises cleaning and preparing a collection site by a preparation pad prior to penetrating the membrane.

In an additional aspect, the method further comprises detecting a target sequence in the biological sample collected by the collector.

BRIEF DESCRIPTION OF THE DRAWINGS

The accompanying drawings, which are incorporated into and constitute a part of this specification, illustrate one or more embodiments of the present application and, together with the detailed description, serve to explain the principles and implementations of the application. In addition, both US Publication Nos. 2010/0267585 and 2013/0005594 are expressly incorporated herein by reference in their entirety, and specifically all Figures and Legends therein.

FIG. 1C is a partially exploded perspective view illustrating the device of FIG. 1A.

FIG. 1D is a cross-sectional view of FIG. 1C along the line 1D-1D.

FIG. 3A is an exploded side view illustrating a retainer in a device for collecting and stabilizing a biological sample in accord with some embodiments of the present invention.

FIG. 3B is a cross-sectional view of FIG. 3B along the line 3B-3B.

FIG. 3C is a side view illustrating the retainer of FIG. 3A.

FIG. 3D is a cross-sectional view of FIG. 3C along the line 3D-3D.

FIG. 6C is a partially exploded perspective view illustrating the device of FIG. 6A.

FIG. 6D is a cross-sectional view of FIG. 6C along the line 6D-6D.

FIG. 7A is a partially exploded side view illustrating a collector in a device for collecting and stabilizing a biological sample in accord with some embodiments of the present invention.

FIG. 7B is a cross-sectional view of FIG. 7B along the line 7B-7B.

FIG. 8A is an exploded side view illustrating a retainer in a device for collecting and stabilizing a biological sample in accord with some embodiments of the present invention.

FIG. 8B is a cross-sectional view of FIG. 8B along the line 8B-8B.

FIG. 8C is a side view illustrating the retainer of FIG. 8A.

FIG. 8D is a cross-sectional view of FIG. 8C along the line 8D-8D.

FIG. 10B is a partially enlarged view of FIG. 10A.

FIG. 21A depicts a similar orientation to FIG. 20, except with the capture probe(s) "downstream" of the ligation probe sets. CM is a capture moiety. As will be appreciated by those in the art, the CM can be on either the 3' or 5' terminus of the capture probe, although it usually is depicted on the 3' end. In addition, the portion of each ligation probe that does not hybridize to a target domain can contain a number of different functionalities, including, but not limited to, primer binding domains, size tags, capture sequences, etc., as is shown in FIG. 20. FIG. 21A shows a situation where the ligation probe sets are spaced over the length of the target in roughly 25-30% increments for a sample integrity assessment. As will be appreciated by those in the art and described in US 2013/0005594, the spacing of the different ligation probe sets can vary as needed. FIG. 21B depicts an alternative orientation. FIG. 21C depicts an orientation that can be used both for integrity assessment or redundancy.

DETAILED DESCRIPTION

Figure 1A:
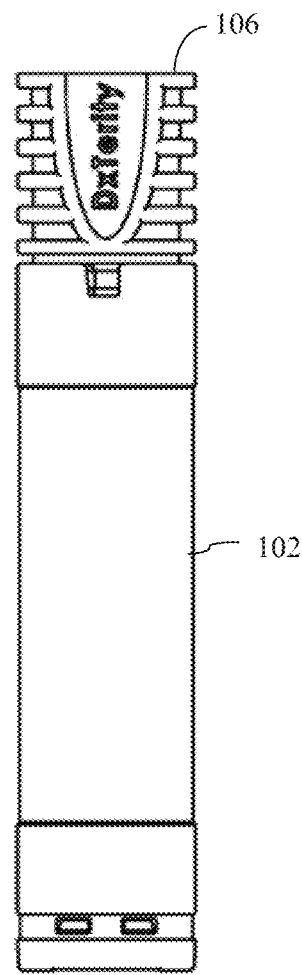
FIG. 1A is a side view illustrating a device for collecting and stabilizing a biological sample in accord with some embodiments of the present invention.
Figure 1B:
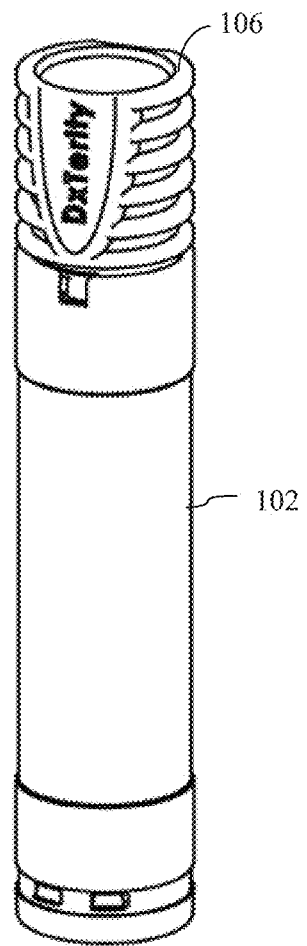
FIG. 1B is a perspective view illustrating the device of FIG. 1A.

The present invention describes a novel design for a collection device that enables simplified collection and storage of small volumes of biological fluid. The ability to collect and simultaneously store biological samples, particularly blood, allows the stable handling of the biological sample, for example, to allow the sample to be mailed using traditional carriers, without additional storage requirements. This can allow easy sampling for the growing field of molecular diagnostics that require immediate stabilization of the genomic material at the time of collection, even in a home collection setting. The design and implementation of the present system allows a patient to easily self-collect a sample, particularly blood, at home and mail the sample, where it can be processed and analyzed using a number of detection systems.

In some embodiments, the target sample is analyzed for target nucleic acid sequences, including DNA and RNA, including mRNA, for example to do diagnosis of genetic or infectious disease, detection of single nucleotide polymorphism (SNP) detection, or gene expression profiling (e.g. mRNA) for the diagnosis and/or prognosis of diseases.

In some embodiments, protein detection and/or quantification for the diagnosis and/or prognosis of disease can be done from the collected sample.

In one embodiment, the collection device enables metering of the amount of biological fluid that is collected. In another embodiment, the collection device facilitates the mixing of the biological sample with additives that aid in the stabilization and future processing of the sample. In another embodiment, the device is designed to separate plasma from blood cells. The device is also designed for easy handling by the patient or medical personnel, and for integration with standard automation and testing systems that are employed in diagnostic testing laboratories.

Embodiments of the present invention are described in the context of collection and stabilization devices and kits. Embodiments of the present invention are also described in the context of collection and stabilization methods that use such collection and stabilization devices and kits to collect and stabilize biological samples.

In various embodiments, a collection and stabilization device of the present invention generally includes a collector for collecting a sample, a retainer for storing stabilization solution or additives and a housing. In some embodiments, the collector is configured such that the collector functions as a handle while obtaining a sample and/or as a seal to seal the sample in the housing. In some embodiments, the collector is configured to have an absorbent member for collecting the biological sample or certain components of the biological sample. In some embodiments, the collector is configured to have a septum that seals the biological sample in the device. The septum is penetrable or permeable such that the biological sample is accessible for subsequent use or testing without removing the collector from the housing. In some embodiments, the collector is configured to have a plasma membrane for generating or separating plasma from the biological sample.

In various embodiments, a method of the present invention generally includes collecting a biological sample using the collector and inserting the collector into the housing. In some embodiments, the method further includes transporting or shipping the collector along with the housing to a receiver such as a testing lab for subsequent processing.

Those of ordinary skill in the art will realize that the following detailed description of the present application is illustrative only and is not intended to be in any way limiting. Other embodiments of the present application will readily suggest themselves to such skilled persons having benefit of this disclosure. Reference will now be made in detail to implementations of the present application as illustrated in the accompanying drawings. The same reference indicators will be used throughout the drawings and the following detailed description to refer to the same or like parts.

In the interest of clarity, not all of the routine features of the implementations described herein are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another. Moreover, it will be appreciated that such a development effort might be complex and time-consuming, but would nevertheless be a routine undertaking of engineering for those of ordinary skill in the art having the benefit of this disclosure.

Many modifications and variations of this disclosure can be made without departing from its spirit and scope, as will be apparent to those skilled in the art. The specific embodiments described herein are offered by way of example only, and the disclosure is to be limited only by the terms of the appended claims, along with the full scope of equivalents to which such claims are entitled.

Definitions

As used herein, the term "sample" or "biological sample" refers to a fluid from a person, an animal or a device (e.g., a testing tube). In some embodiments, the biological sample is a bodily fluid such as blood, saliva or urine from a user's fingertip, earlobe, heel or other location. In some embodiments, the biological sample refers to a small amount of fluid, typically in the order of 1 µL to 2000 µL, preferably from 5 µL to 200 µL, and more preferably from 20 to 100 µL.

As used herein, the term "collector" refers to a component of the collection and stabilization device of the present invention that is designed for collecting or obtaining a biological sample. In some embodiments, the collector is configured to perform other functions, such as sealing a biological sample in a housing or as a handle for a user to hold the collector while taking the biological sample. Accordingly, the term "collector" in some cases is interchangable with "cap", "device cap", "collector cap", "handle", "fingerstick", "stick" or the like.

As used herein, the term "retainer" refers to a component of the collection and stabilization device of the present invention that is designed for holding a solution, additives, reagents or other chemical/biological substances. In some embodiments, the solution, additives, or reagents include a stabilization buffer, such as DxTerity RNA blood stabilization buffer (DxCollect™) described in US Publication No. 2013/0005594, as is further outlined below or a buffer for eluting blood plasma. Accordingly, the term "retainer" in some cases is interchangable with "container", "cup", "buffer container", "buffer cup" or the like.

As used herein, the term "housing" refers to a component of the collection and stabilization device of the present invention that is designed for holding the retainer and engaging or coupling with the collector. In some embodiments, it has a tube-like configuration and provides protection to the biological sample while shipping or transporting the device. Accordingly, the term "housing" in some cases is interchangable with "tube", "transport tube" or the like.

As used herein, the term "absorbent member" refers to a component of the collector that is designed for obtaining and tentatively holding a biological sample. In some embodiments, the absorbent member is made of a sponge like wicking material comprising cellulosic, polyester, polyvinyl alcohol, foam, porous media or other suitable materials. Accordingly, the term "absorbent member" in some cases is interchangable with "sponge", "wicking sponge", "wicking material", or the like. In some embodiments, selection of the material and configuration (e.g., shape, size) of the absorbent member are in accord with the type and the amount of the biological sample to be collected. In some embodiments, the material is selected to collect certain components of the biological sample.

As used herein, the term "releasing a biological sample", "releasing the biological sample", "eluting a biological sample" or the like does not necessarily refer to complete release of the entire biological sample that has been collected by the collector. In some embodiments, the term "releasing a biological sample", "releasing the biological sample", "eluting a biological sample" or the like refers to releasing only a percentage, for instance, between 30% and 50%, between 50% and 70% or between 70% and 90% of the biological sample that has been collected by the collector. In some embodiments, the term "releasing a biological sample", "releasing the biological sample", "eluting a biological sample" or the like refers to releasing only a targeted component or components of the biological sample.

As used herein, the term "propelling a solution to flow through the absorbent member", "pushing a solution to flow through the absorbent member" or the like does not necessarily refer to propelling the entire solution that has been stored in the retainer through the absorbent member. In some embodiments, the term "propelling a solution to flow through the absorbent member", "pushing a solution to flow through the absorbent member" or the like refers to propelling only a percentage, for instance, between 30% and 50%, between 50% and 70% or between 70% and 90% of the solution that has been stored in the retainer through the absorbent member.

As used herein, the term "solution", "additives" or "reagents" refers to chemical or biological material that aid in the stabilization and future processing of the samples. In some embodiments, the solution in the retainer contains additives that alter the properties of the biological sample, for example, by stabilizing the components against degradation, partially or fully lysing the cells of the biological sample, separating one component or species from the biological sample, adding a chemical reagent for diagnostic testing, or reducing clotting. In some embodiments, the solution, additives, or reagents include a stabilization buffer, such as DxTerity RNA blood stabilization buffer (DxCollect™) described in US Publication No. 2013/0005594 and below, or a buffer for eluting blood plasma. Alternatively, cell-free DNA/RNA testing can be done using cell stabilization buffers like those sold by Streck by Streck under the trade name Cell Free DNA BCT® and Cell Free RNA BCT®.

As used herein, the terms "top" or "bottom", "inward" or "outward", "longitudinal", "perpendicular" or "circumferential" etc., are used to describe features of the exemplary embodiments with reference to the positions of such features as displayed in the figures. They are used for convenience in explanation, and do not limit features in such positions.

As used herein, the term "nominal diameter" refers to a characteristic dimension of a cross-sectional surface area of a feature. For instance, the nominal diameter for a cylindrical feature with a circular cross section is the same as the diameter of the circular cross section. For a feature with irregular or complex cross section, the nominal diameter may be defined by the diameter of a hypothetical circle which has the same area as of the irregular or complex cross section.

As used herein, the term "average" refers to the arithmetic mean value, or some other measure of central tendency, of a characteristic dimension. For example, in a case of a feature (e.g., housing or collector) having a variable cross section along its longitudinal axis, the average nominal diameter of the feature is the mean nominal diameter of the feature over its length.

As used herein, "sample" refers to bodily fluids (including, but not limited to, blood, urine, serum, lymph, saliva, anal and vaginal secretions, perspiration and semen, of virtually any organism, with mammalian samples being preferred and human samples being particularly preferred). The sample contains target nucleic acids and/or target proteins.

By "nucleic acid" or "oligonucleotide" or grammatical equivalents herein means at least two nucleotides covalently linked together. The target nucleic acids may comprise DNA or RNA. A nucleic acid of the present invention will generally contain phosphodiester bonds (for example in the case of the target sequences), although in some cases, as outlined below, nucleic acid analogs are included that may have alternate backbones (particularly for use with the ligation, label or capture probes), comprising, for example, phosphoramide (Beaucage et al., *Tetrahedron* (1993) 49(10):1925 and references therein; Letsinger, *J. Org. Chem.* (1970) 35:3800; Sprinzl et al., *Eur. J. Biochem.* (1977) 81:579; Letsinger et al., *Nucl. Acids Res.* (1986) 14:3487; Sawai et al, *Chem. Lett.* (1984) 805; Letsinger et al., *J. Am. Chem. Soc.* (1988) 110:4470; and Pauwels et al., Chemica *Scripta* (1986) 26:141), phosphorothioate (Mag et al., *Nucleic Acids Res.* (1991) 19:1437; and U.S. Pat. No. 5,644,048), phosphorodithioate (Briu et al., *J. Am. Chem. Soc.* (1989) 111:2321, O-methylphophoroamidite linkages (see Eckstein, Oligonucleotides and Analogues: A Practical Approach, Oxford University Press), and peptide nucleic acid backbones and linkages (see Egholm, *J. Am. Chem. Soc.* (1992)114:1895; Meier et al., *Chem. Int. Ed. Engl.* (1992) 31:1008; Nielsen, *Nature*, (1993) 365:566; Carlsson et al., *Nature* (1996) 380:207, all of which are incorporated herein by reference in their entirety). Other analog nucleic acids include those with bicyclic structures including locked nucleic acids, Koshkin et al., *J. Am. Chem. Soc.* (1998) 120:13252 3); positive backbones (Denpcy et al., *Proc. Natl. Acad. Sci. USA* (1995) 92:6097; non-ionic backbones (U.S. Pat. Nos. 5,386,023, 5,637,684, 5,602,240, 5,216,141 and 4,469,863; Kiedrowshi et al., *Angew. Chem. Intl. Ed. English* (1991) 30:423; Letsinger et al., *J. Am. Chem. Soc.* (1988) 110:4470; Letsinger et al., *Nucleoside & Nucleotide* (1994) 13:1597; Chapters 2 and 3, ASC Symposium Series 580, Ed. Y. S. Sanghui and P. Dan Cook; Mesmaeker et al., *Bioorganic & Medicinal Chem. Lett.* (1994) 4:395; Jeffs et al., *J. Biomolecular NMR* (1994) 34:17; Xu et al., *Tetrahedron Lett.* (1996) 37:743) and non-ribose backbones, including those described in U.S. Pat. Nos. 5,235,033 and 5,034, 506, and Chapters 6 and 7, ASC Symposium Series 580, Ed. Y. S. Sanghui and P. Dan Cook. Nucleic acids containing one or more carbocyclic sugars are also included within the definition of nucleic acids (see Jenkins et al., *Chem. Soc. Rev.* (1995) pp 169-176). Several nucleic acid analogs are described in Rawls, *C & E News* Jun. 2, 1997 page 35. All of these references are herein expressly incorporated by reference in their entirety for all purposes, and in particular for all teachings related to nucleic acids. These modifications of the ribose-phosphate backbone may be done to facilitate the addition of labels or other moieties, to increase or decrease the stability and half-life of such molecules in physiological environments, etc.

By "target sequence" or "target nucleic acid" or grammatical equivalents herein means a nucleic acid sequence on a single strand of nucleic acid. The target sequence may be a portion of a gene, a regulatory sequence, genomic DNA, cDNA, RNA including mRNA, MicroRNA and rRNA, or others. As is outlined herein, the target sequence may be a target sequence from a sample, or a secondary target such as a product of an amplification reaction, etc. It may be any length, with the understanding that longer sequences are more specific. As will be appreciated by those in the art, the complementary target sequence may take many forms. For example, it may be contained within a larger nucleic acid sequence, i.e. all or part of a gene or mRNA, a restriction fragment of a plasmid or genomic DNA, among others. Any and all combinations of these may serve as target nucleic acids in a particular assay. In many cases, multiplex assays are done, where a plurality of target sequences are simultaneously detected, such as for gene expression profiling as is more fully described below.

In general, each target sequence is comprised of a plurality of different target domains. Each target sequence has at least a pair of ligation domains for hybridization to a set of ligation probes, or more, as described below. For example, a first target domain of a sample target sequence may hybridize to a first ligation probe, and a second target domain in the target sequence may hybridize to a second ligation probe, such as to bring the chemical ligation moieties into spatial proximity sufficient to allow spontaneous chemical ligation.

In general, each pair of target ligation domains is adjacent to each other, that is, there are no nucleotides separating the two domains. This finds use in both general detection of target sequences (e.g. gene expression profiling using mRNA as the target sequences), transfer reactions as discussed below, as well as for single nucleotide polymorphism (SNP) detection. For SNP detection, the target sequence comprises a position for which sequence information is desired, generally referred to herein as the "detection position". In some embodiments, the detection position is a single nucleotide, although in some embodiments, it may comprise a plurality of nucleotides, either contiguous with each other or separated by one or more nucleotides. By "plurality" as used herein is meant at least two. As used herein, the base of a ligation probe which basepairs with the detection position base in a hybrid is termed the "interrogation position".

Figure 11:
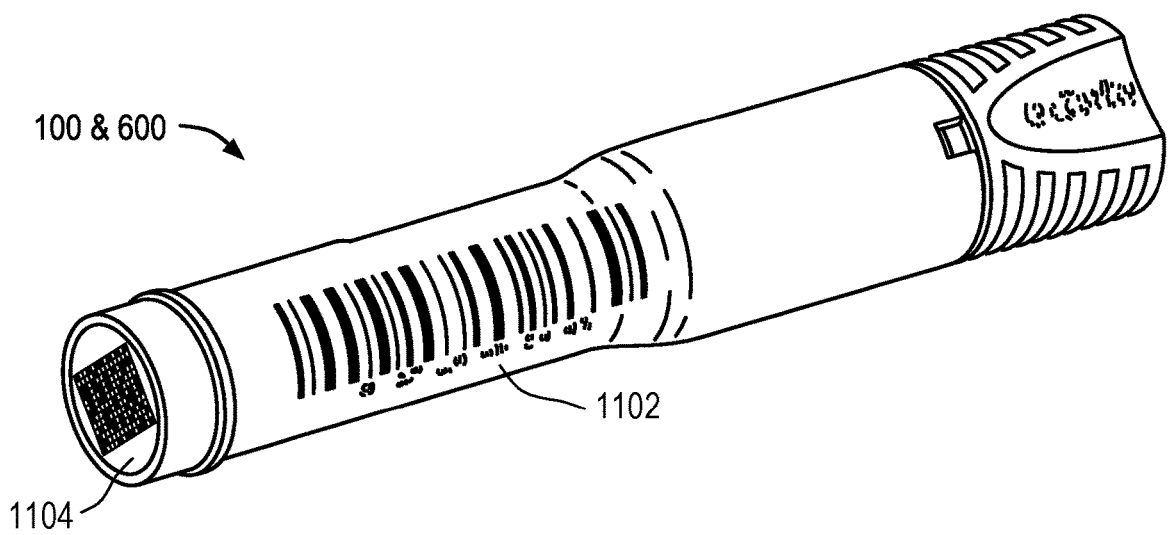
FIG. 11 is a perspective view illustrating a device for collecting and stabilizing a biological sample in accord with some embodiments of the present invention.
Figure 12:
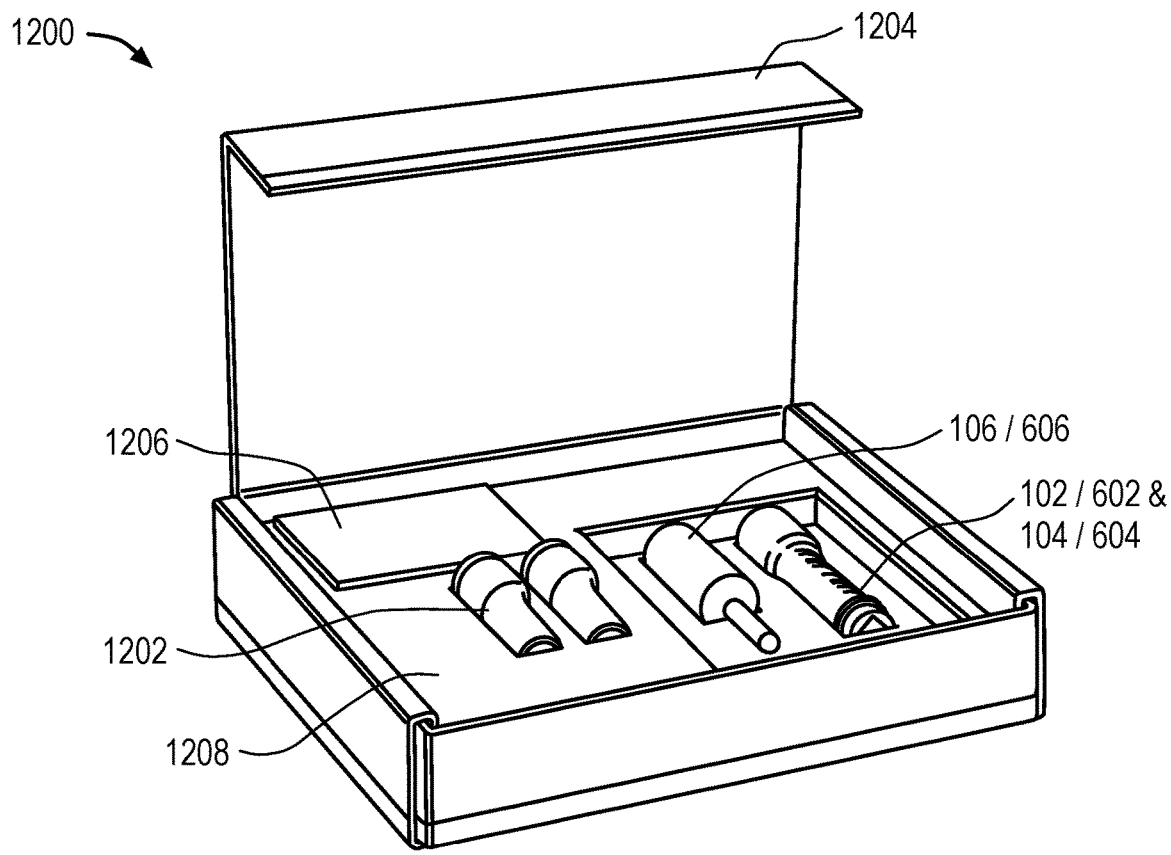
FIG. 12 is a perspective view illustrating a kit including a device for collecting and stabilizing a biological sample in accord with some embodiments of the present invention.

Each sample target nucleic acid can additionally have multiple pairs of ligation domains. That is, 1, 2, 3 or more sets of ligation probes can hybridize to the same target sequence at multiple locations, as is generally depicted in FIG. 11 or 12. As is more fully outlined below, the use of multiple ligation domains per target nucleic acid can serve as the basis to assess the integrity of the target nucleic acids (and/or the original sample) in the sample.

The sample target nucleic acids may contain other domains, in addition to ligation domains. In certain embodiments, the target nucleic acids of the invention include a target capture domain to which a target capture domain is able to hybridize. In general, as depicted in FIG. 11 and depending on the purpose of the assay, a target capture domain can be "upstream", "downstream" or "in-between" one or more of the ligation domains of the target nucleic acid.

Unless specified, the terms "first" and "second" are not meant to confer an orientation of the sequences with respect to the 5'-3' orientation of the target sequence. For example, assuming a 5'-3' orientation of the complementary target sequence, the first target domain may be located either 5' to the second domain, or 3' to the second domain. For ease of reference and not to be limiting, these domains are sometimes referred to as "upstream" and "downstream", with the normal convention being the target sequence being displayed in a 5' to 3' orientation. However, it should be noted that ligation domains have an orientation such that the 3' and 5' ligation moieties of the ligation probe sets hybridize either completely adjacently (e.g. no intervening nucleobases) or within a distance that the linkers attaching the ligation moieties allow for ligation.

Devices, Kits And Methods

FIGS. 1A-1D illustrate an exemplary device 100 for collecting and stabilizing biological samples in accordance with some embodiments of the present invention. As illustrated, the exemplary device 100 generally includes a collector 106 for collecting a biological sample, a retainer 104 for storing a solution, additives, reagents or the like that aid in the stabilization and future processing of the biological sample, and a housing 102 for accommodating the retainer 104 and engaging with the collector 106. In various embodiments, the collector 106 includes an absorbent member 118 for collecting the biological sample. The retainer 104 includes a vessel 114 or a container for receiving the solution and a penetrable seal 116 for enclosing the solution within the vessel 114. The retainer 104 is configured to be insertable into the housing 102. In some embodiments, the housing 102 includes an open end portion 108 for engaging with the collector 106, an closed end portion 110 and an interior space 112 for receiving the retainer 104.

In some embodiments, the collector 106 is removably engaged with the housing 102 or with the opening end portion of the housing 102. For instance, the collector 106 can be screwed on or off the housing 102. In some embodiments, the collector 106 is configure to mate with the housing 102 and sealingly (e.g., liquid tight) engaged with the housing 102 to prevent liquid leakage. The sealingly engagement of the collector 106 and the housing 102 can be achieved by screw fitting, press fitting, use of sealing ring(s), and various other suitable ways.

Figures 5A, 5B, 5C:
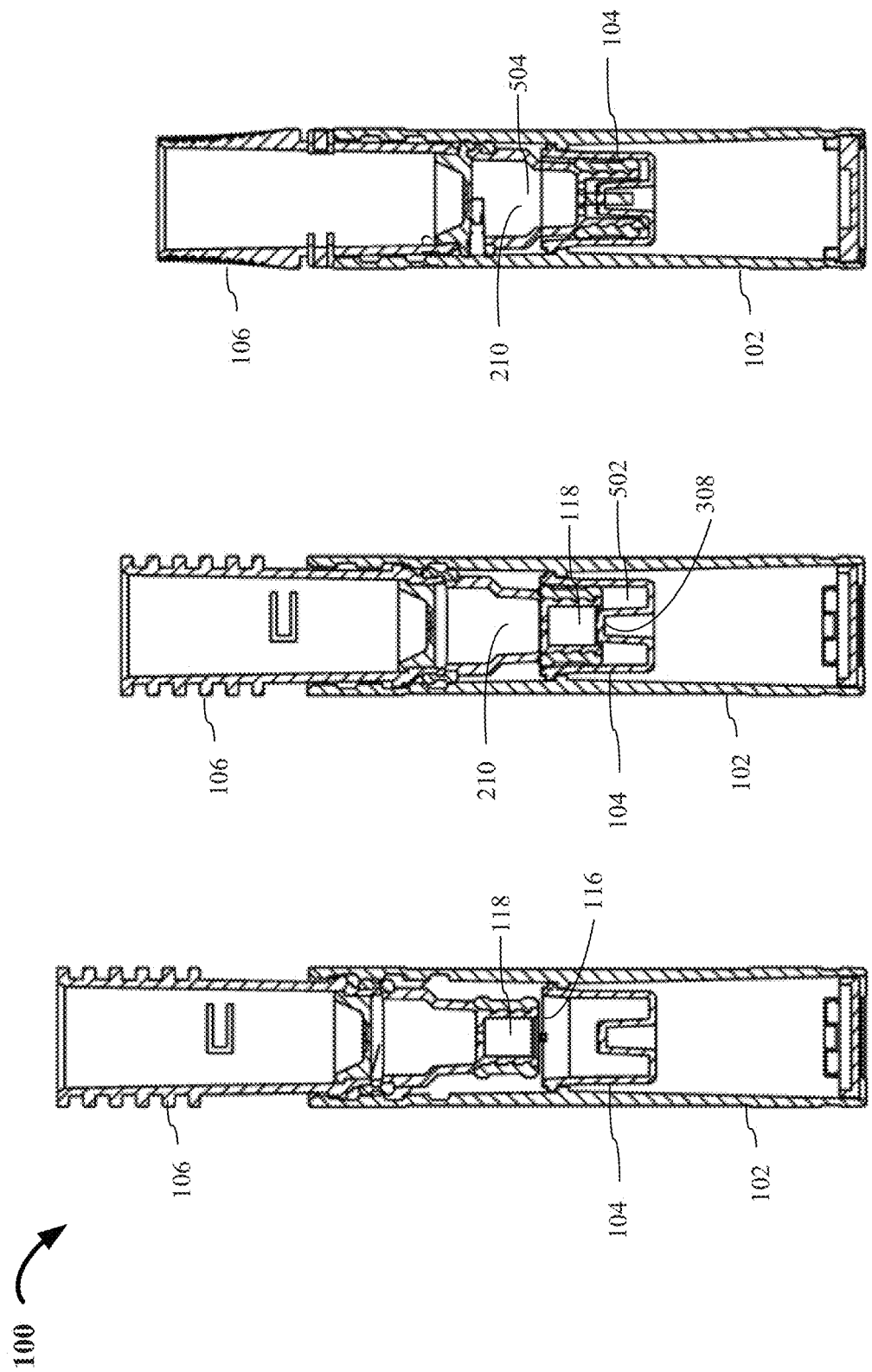
FIG. 5A, FIG. 5B and FIG. 5C are cross-sectional views illustrating a device for collecting and stabilizing a biological sample in accord with some embodiments of the present invention, where a collector is engaging with a housing at different stages.
Figures 6A, 6B:
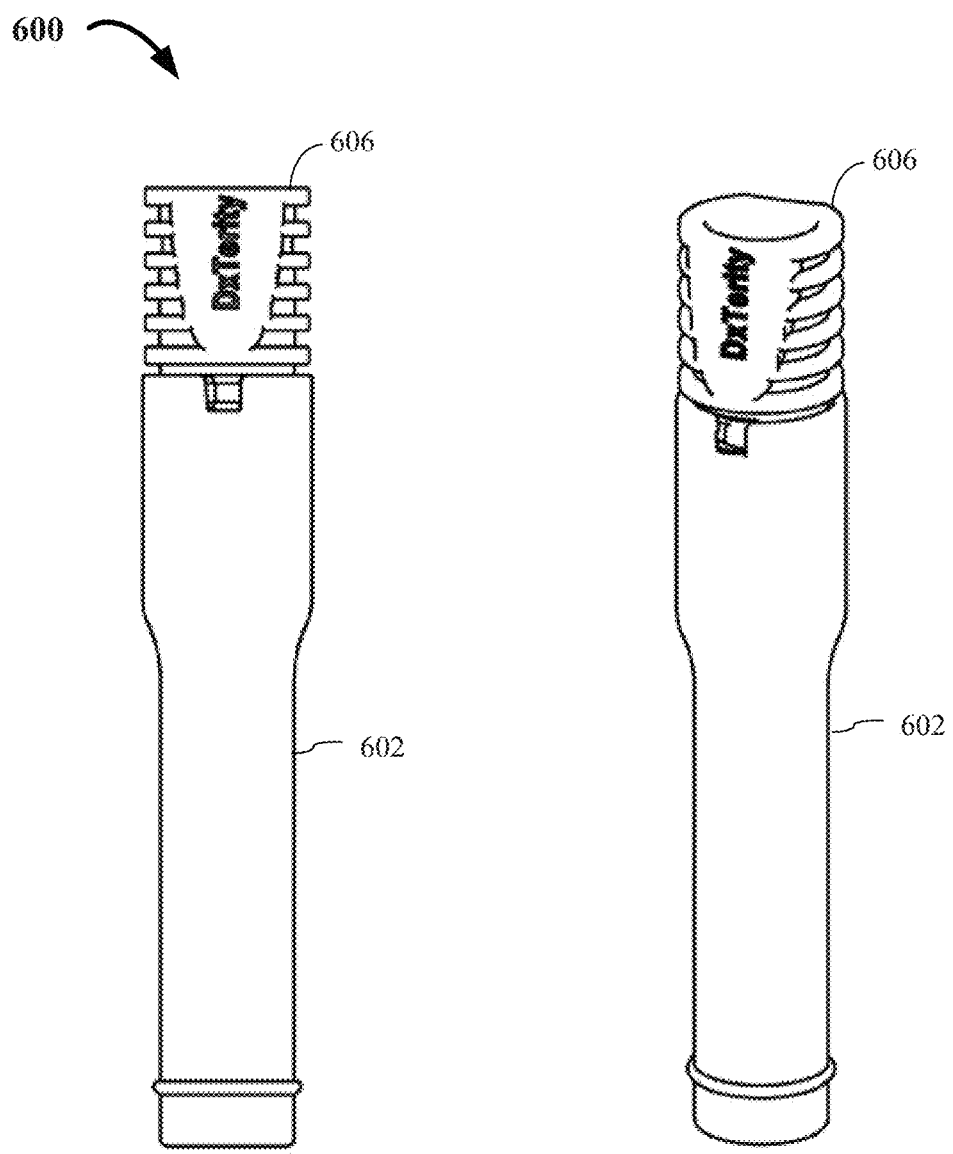
FIG. 6A is a side view illustrating a device for collecting and stabilizing a biological sample in accord with some embodiments of the present invention.
FIG. 6B is a perspective view illustrating the device of FIG. 6A.
Figure 7D:
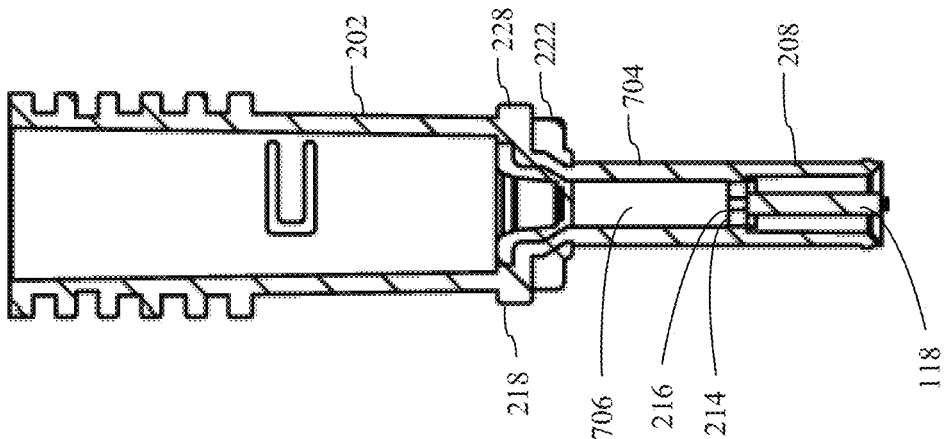
FIG. 7D is a cross-sectional view of FIG. 7C along the line 7D-7D.
Figure 7C:
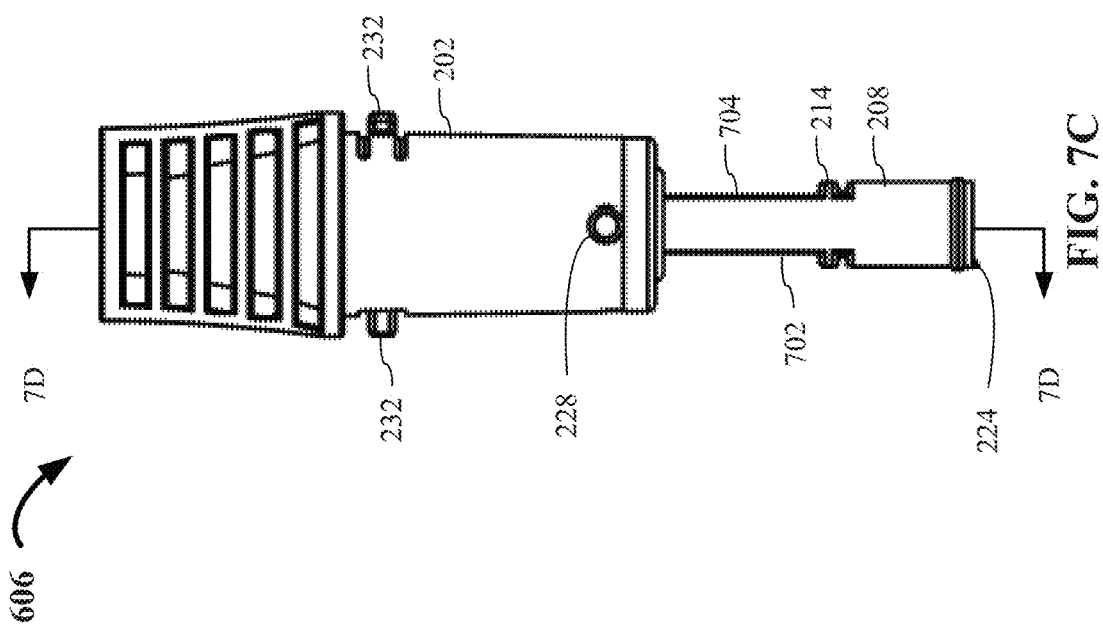
FIG. 7C is a side view illustrating the collector of FIG. 7A.

When the collector 106 is engaging or engaged with the housing 102, the absorbent member 118 is received in the housing 102. At a certain point, for example, as illustrated in FIG. 5A, the collector 106 (e.g., the tip of the collector) breaks the penetrable seal 116 of the retainer 104 that has been inserted into the interior space 112 of the housing 102. As the collector 106 advances further into the housing 102 as illustrated in FIGS. 5B and 5C, the collector 106 propels the solution 502 stored in the retainer 104 to flow through the absorbent member 118. As a result, the biological sample is released from the absorbent member 118 and mixed with the solution to form a stabilized biological sample mixture 504.

In some embodiments, the collector 106 and the retainer 104 are configured so that upon insertion of the collector 106 into the retainer 104, the solution is pushed through the absorbent member 118 and helps elute the biological sample (e.g., blood) from the absorbent member 118. In a preferred embodiment, the solution in the retainer 104 mixes with the eluted biological sample during the process of inserting the collector 106 into the retainer 104. In some embodiments, the solution in the retainer 104 contains additives that alter the properties of the biological sample, for example, by stabilizing the components against degradation, partially or fully lysing the cells of the biological sample, separating one component or species from the biological sample, adding a chemical reagent for diagnostic testing, or reducing clotting.

The absorbent member 118 can be made of a variety of materials and configured in a variety of shapes and sizes. Generally, the material is selected and the absorbent member 118 is configured in accord with the type and the amount of the biological sample to be collected. In some embodiments, the material is selected so that the absorbent member 118 may irreversibly bind and retain certain components of the biological sample. Alternatively, the material may be chosen so that the absorbent member 118 possesses minimal retention of some or all of the biological components when it is compressed or the biological sample is eluted off. In various embodiments, the absorbent member 118 is made of a wicking material comprising cellulosic, polyester, polyvinyl alcohol, foam or other suitable materials. In an embodiment, the absorbent member 118 is a sponge made of polyvinyl alcohol foam.

In some embodiments, the absorbent member 118 is configured to absorb or retain a predetermined amount of the biological sample. For instance, in some embodiments, the absorbent member 118 collects between 1 µL and 2000 µL, between 5 µL and 200 µL, or between 20 µL and 100 µL of the biological sample. The absorbent member 118 can be of a cube, a sheet, a column or any suitable shapes and sizes as long as it can be attached or fitted to the collector 106. In a preferred embodiment, the absorbent member 118 has a shape and size that fit to a cavity 212 of the collector 106.

By way of illustration, FIGS. 2A-2D depict an exemplary collector 106 for collecting a biological sample in accordance with some embodiments of the present invention. As illustrated, the exemplary collector 106 comprises a body or a body portion 202 and a stem or a stem portion 204. In an embodiment, the body portion 202 and the stem portion 204 are made separately and then fixedly coupled to each other. In a preferred embodiment, the body portion 202 is monolithically or integrally formed with the stem portion 204, for example, by injection molding or other existing manufacturing methods. In some embodiments, the body portion 202 is configured such that it serves as a handle when taking the biological sample and as a seal when engaging with the open end portion 108 of the housing 102. In some embodiments, the stem portion 204 is configured to include a first segment 206 proximal to the body portion 202 and a second segment 208 distal to the body portion 202. In such embodiments, the absorbent member 118 is attached to or fitted in the second segment 208 of the stem portion 204. When the collector 106 is engaged with the housing 102 or the open end portion 108 of the housing 102 (for example, as shown in FIG. 5C), the absorbent member 118 and at least a portion of the second segment 208 are received in the retainer 104 so as to propel the solution to flow through the absorbent member 118.

The body portion 202 and the stem portion 204 of the collector 106 in the present invention can be made of various materials. For example, the body portion and the stem portion 204 can be made of a plastic, a thermoplastic, or a metal. Examples of plastics include an inert thermoplastic, polycarbonate, polyethylene terephthalate, polyurethane, or a medical grade polypropylene. Preferably, the collector 106 is made of a material rigid enough to provide easy and precise handling of the collector 106. More preferably, the collector 106 is made with a relatively inert thermoplastic such as medical grade polypropylene. In one embodiment, the body portion 202 and the stem portion 204 are made of different materials. In another embodiment, the body portion 202 and the stem portion 204 are made of the same material such as a medical grade polypropylene.

In various embodiments, the body portion 202 and the stem portion 204 are substantially cylindrical and hollow. In some embodiments, such as those illustrated in FIGS. 1A-2D, the body portion 202 and the stem portion 204 are substantially cylindrical, each with a substantially circular cross section (i.e., the cross section perpendicular to the longitudinal axis of the body portion 202 or the stem portion 204). The body portion 202 may be approximately 2 cm to 8 cm long with an average nominal diameter between 1 cm and 3 cm. The stem portion 204 may be approximately 1 cm to 5 cm long with an average nominal diameter between 0.5 cm and 2.5 cm. In a preferred embodiment, the body portion 202 is approximately 4 cm long with an average nominal diameter of approximately 1.5 cm, and the stem portion 204 is approximately 2 cm long with an average nominal diameter of approximately 1 cm.

It is to be understood that the body portion 202 and the stem portion 204 can be of any suitable shapes and sizes, not necessarily with a substantially circular cross section. For example, the body portion 202 can be configured to have at least a segment with a polygonal (e.g., hexagon, heptagon), asymmetric or irregular cross section. Such a segment may be used as a handle for a user to hold the collector 106 while taking the biological sample or engaging the collector 106 with the housing 102. Similar, the body portion 202 can be configured to have at least a segment (e.g., the second segment 208) with a cross section in accord with the retainer 104 to help propelling the solution out of the retainer 104.

In some embodiments, the first segment 206 proximal to the body portion 202 is formed with a reservoir 210. The reservoir 210 has a volume that is between 1 µL and 5000 µL, preferably between 20 µL and 1000 µL, or more preferably between 400_, and 500 µL. The reservoir 210 allows the biological sample released from the absorbent member 118 to mix with the propelled solution. The reservoir 210 can be used to store the mixture of the biological sample and the solution (e.g., 504 in FIG. 5C) until the mixture is retrieved for subsequent processes.

In some embodiments, the second segment 208 distal to the body portion 202 is formed with a cavity 212, and the absorbent member 118 is disposed or inserted in the cavity 212. The cavity 212 can hold the absorbent member 118 using an adhesive or simply by friction force. In such embodiments, the stem portion 204 is configured to have a partition 214 formed between the first segment 206 and the second segment 208. The partition 214 prevents the absorbent member 118 from being pushed into the first segment 206 when the collector 106 is engaging with the housing 102. Meanwhile, the partition 214 is formed with one or more holes or slots 216, through which the first segment 206 is in fluidic communication with the second segment 208. In some embodiments, the partition 214 is formed with a plurality of holes or slots 216 circumferentially distributed along the central axis of the partition 214. Thus, while preventing the absorbent member 118 from being pushed into the first segment 206, the partition 214 allows the released biological sample and the propelled solution flow through and into the first segment 206.

In some embodiments, the partition 214 is not formed with a hole or slot but is made of a porous material that allows the first segment 206 in fluidic communication with the second segment 208. In some embodiments, the partition 214 is made of a material that can remove an undesired component or components from the biological sample such as blood cells from a blood sample.

To prevent the mixture of the biological sample and the solution from flowing out through the body portion 202, in some embodiments, the collector 106 includes a septum 218 disposed within the body portion 202 and preferably adjacent to the stem portion 204. The septum 218 is penetrable or pierceable, for example, by a pipette, so that the mixture of the biological sample and the solution is accessible and can be retrieved for subsequent use or processing without removing the collector 106 from the housing 102. Ideally, the penetrable or pierceable septum 218 is self-resealing and can be penetrated multiple times and still provide a liquid tight seal to the biological sample or the mixture of the biological sample and the solution. The septum 218 can be made from a variety of materials including vulcanized rubber, interwoven fabric, or a thermoplastic elastomer. In a preferred embodiment, the septum 218 is made of a thermoplastic elastomer.

Additionally or optionally, the collector 106 includes one or more seals, preferably elastomeric seals. For example, in some embodiments, the collector 106 includes a first elastomeric seal 220 disposed on an exterior surface of the second segment 208 of the stem portion 204. The first elastomeric seal 220 provides sealing between the exterior surface of the second segment 208 of the stem portion 204 and an interior surface of the retainer 104 when the collector 106 is engaging or engaged with the open end portion 108 of the housing 102.

In addition to the first elastomeric seal 220, in some embodiments, the collector 106 includes a second elastomeric seal 222. The second elastomeric seal 222 can be disposed at various places. In one embodiment, the second elastomeric seal 222 is disposed on an exterior surface of the first segment 206 of the stem portion 204. In such an embodiment, the second elastomeric seal 222 provides sealing between the exterior surface of the first segment 206 of the stem portion 204 and the interior surface of the housing 102 when the collector 106 is engaging or engaged with the housing 102. In another embodiment, the second elastomeric seal 222 is disposed on an exterior surface of the body portion 202 adjacent to the stem portion 204. Thus, when the collector 106 is engaging or engaged with the open end portion 108 of the housing 102, the second elastomeric seal 222 provides sealing between the exterior surface of the body portion 202 and the interior surface of the housing 102. In some embodiments, the second elastomeric seal 222 also serves as a coupler that couples the body portion 202 with the stem portion 204.

The first and second elastomeric seals can be made of various materials, including but not limited to vulcanized rubber, interwoven fabric, or a thermoplastic elastomer. The first and second elastomeric seals can be made of the same material or different materials. In one embodiment, the first and second elastomeric seals are made separately and then coupled to the collector 106. In another embodiment, the first and second elastomeric seals are made integrally or monolithically with the collector 106, for example, by injection molding with two or more different materials. In still another embodiment, the first and second elastomeric seals are applied to the collector 106 like a coating.

In some embodiments, the collector 106 also includes a means or a mechanism for breaking the penetrable seal 116 of the retainer 104 when the collector 106 is engaging with the housing 102. The means for breaking the penetrable seal 116 of the retainer 104 can be configured to have various shapes and sizes. For example, it can be a protruded pointer, a sharp edge or simply the relatively rigid wall of the second segment 208 of the stem portion 204. In a preferred embodiment, the means for breaking the penetrable seal 116 of the retainer 104 includes a tooth 224 or a plurality of teeth protruded from an edge of the second segment 208 of the stem portion 204.

In some embodiments, the collector 106 is configured to have various additional or optional features. For instance, in some embodiments, a rib 226 is formed on an exterior surface of the second segment 208 of the stem portion 204. In the illustrated embodiments, the rib 226 is formed and circumferentially along the exterior surface of the second segment 208 of the stem portion 204. When the collector 106 is engaging with the open end portion 108 of the housing 102, the rib 226 acts as a plunger and help propelling the solution to flow through the absorbent member 118. In embodiments where a seal (e.g., the first elastomeric seal 220) is disposed on the second segment 208 of the stem portion 204, the rib 226 also helps retaining the seal in place. In such embodiments, the rib 226 together with the seal collectively acts as a plunge. In some embodiments, a plurality of ribs is formed on the exterior surface of the second segment 208 of the stem portion 204.

Figure 2A:
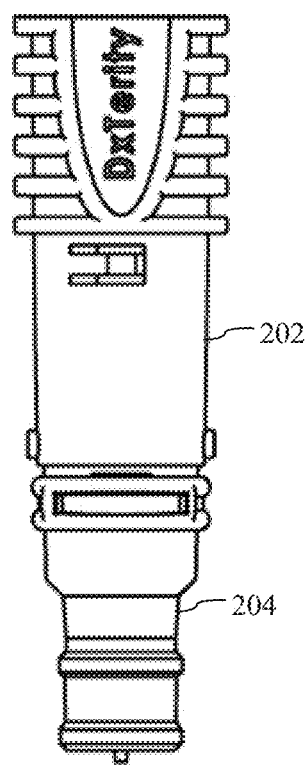
FIG. 2A is a partially exploded side view illustrating a collector in a device for collecting and stabilizing a biological sample in accord with some embodiments of the present invention.
Figure 2B:
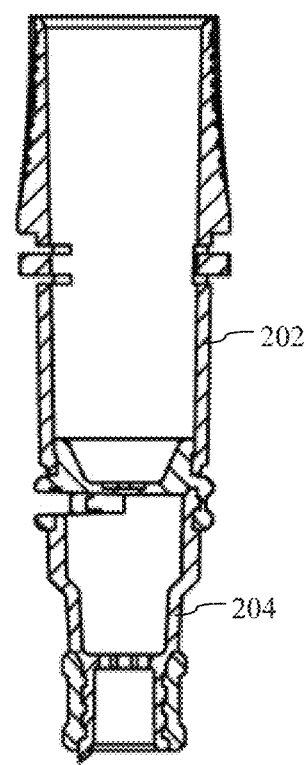
FIG. 2B is a cross-sectional view of FIG. 2B along the line 2B-2B.
Figure 2D:
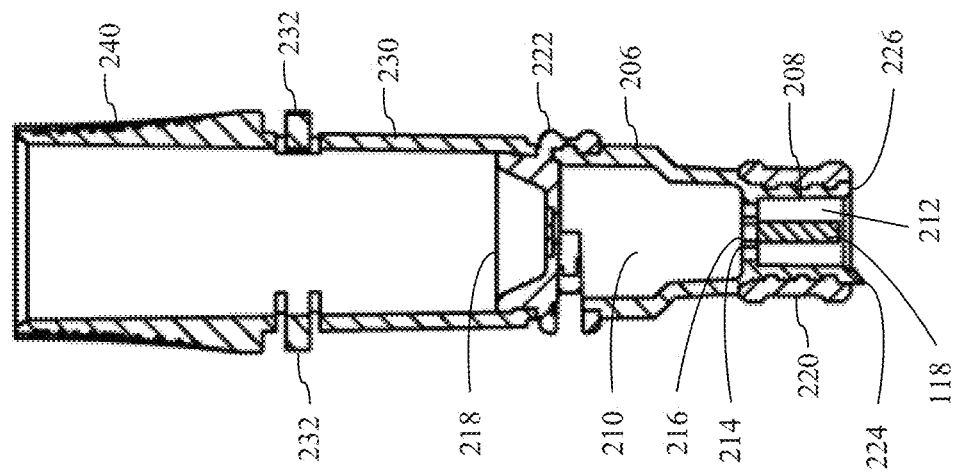
FIG. 2D is a cross-sectional view of FIG. 2C along the line 2D-2D.
Figure 2C:
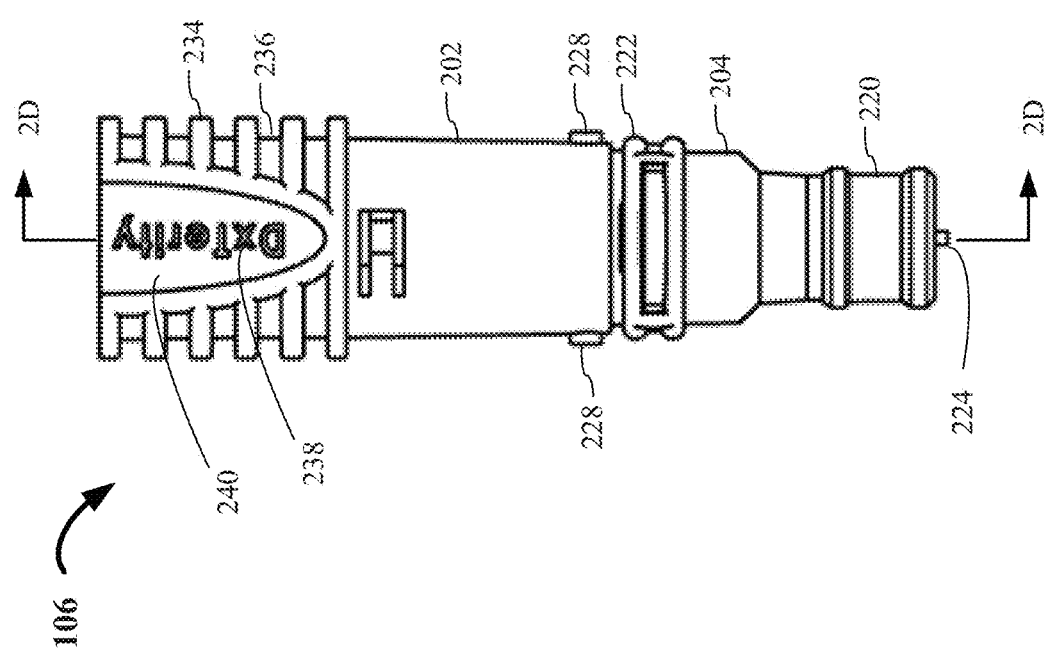
FIG. 2C is a side view illustrating the collector of FIG. 2A.

In some embodiments, the collector 106 and the housing 102 are configured so that the collector 106 can be screwed onto the housing 102. For instance, in an preferred embodiment, the housing 102 is formed with an internal thread or a guide track 402 such as those illustrated in FIGS. 4B and 4D, and the collector 106 is configured to have one or more pins 228 for guiding and screwing the collector 106 to the housing 102. Preferably, the one or more pins 228 are formed on a side wall 230 of the body portion 202 and proximal to the stem portion 204. More preferably, the collector 106 is configured to have two pins 228 formed on the side wall 230 of the body portion 202 and opposite or substantially opposite to each other as illustrated in FIG. 2C. In some embodiments, the one or more pins 228 also serve as a stopper to prevent the collector 106 from being pushed unintentionally too deep into the housing 102 and damaging the retainer 104. It is to be understood that the collector 106 and the housing 102 can be engaged in other ways, for example, by press fitting.

In some embodiments, the collector 106 and the housing 102 are configured with a locking means or mechanism for interlocking the collector 106 with the housing 102 once the collector 106 is engaged with the housing 102. Such a locking means prevents unintentional removal of the collector 106 from the housing 102, for example, during shipping or transporting the device 100 from different locations. For instance, in some embodiments, the housing 102 is configured to have at least one slot 410 and the collector 106 is configured to have at least one detention 232 corresponding to the at least one slot 410 formed in the housing 102. In a preferred embodiment, the locking means is configured to provide a visual, tactile or auditory signal that indicates proper engagement of the collector 106 with the housing 102. As an example, FIG. 4C illustrates two slots 410 formed at the open end portion 108 of the housing 102, and FIG. 2D illustrates two detentions or clips 232 formed on a side wall 230 of the body portion 202 of the collector 106. When the collector 106 is engaged with the housing 102, the two clips 232 are received by the two slots 410, providing a click sound to indicate that the two clips 232 are snapped into the two slots 410. Preferably, the two slots are formed opposite or substantially opposite to each other and the corresponding two clips are formed opposite or substantially opposite to each other.

In some embodiments, the collector 106 is configured to function as a handle so that the collector 106 can be held steadily when used to take a biological sample or when being engaged with the housing 102. For instance, in some embodiments, the collector 106 is configured with an external grip (e.g., 234, 236) formed on a side wall 230 of the body portion 202 of the collector 106 and preferable at a location distal to the stem portion 204. The external grip (e.g., 234, 236) can be formed in various configurations, including recesses, grooves, ribs, pins, protrusions, or any combination of recesses, grooves, ribs, pins, and protrusions. The number and sizes of the recesses, grooves, ribs, pins, and protrusions can also be readily varied. By way of illustration, FIG. 2C illustrates an external grip including ribs 234 and grooves 236 formed on the side wall 230 of the body portion 202 and distal to the stem portion 204.

In some embodiments, the collector 106 is configured to have a surface 240 for placing a brand name or other identification/decoration 238 on the surface 240. The surface 240 can be flat, curvy, concave or convex. The brand name or other identification/decoration 238 can be engraved, printed, or molded on the surface 240, or via other suitable means. As an example, FIG. 2C illustrates a brand name 238 (i.e., DxTerity) integrally or monolithically molded on the surface 240.

Figures 15A, 15B, 15C:
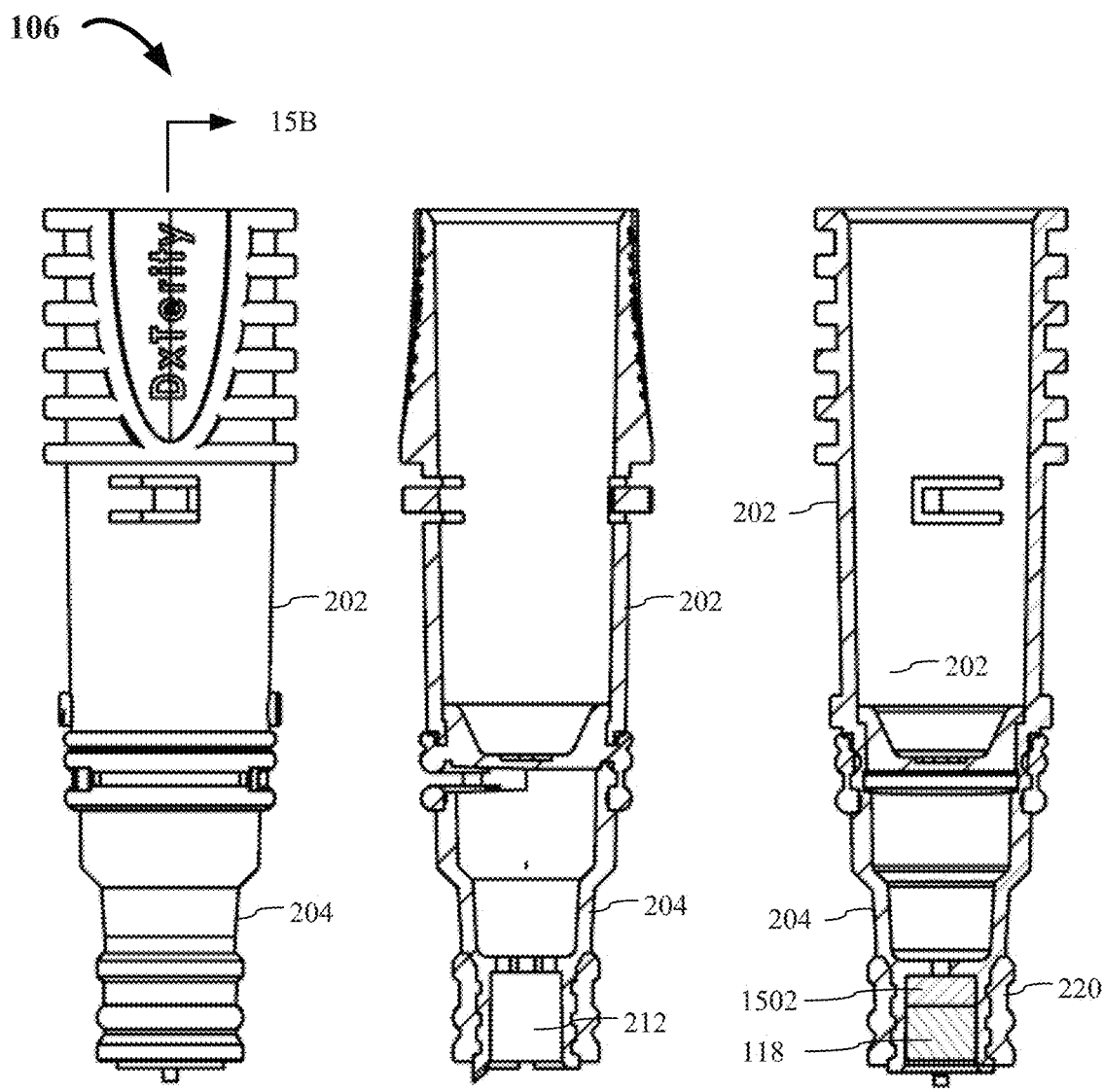
FIG. 15A is a partially exploded side view illustrating a collector in a device for collecting and stabilizing a biological sample in accord with some embodiments of the present invention.
FIG. 15B is a cross-sectional view of FIG. 15B along the line 15B-15B.
FIG. 15C is cross-sectional view illustrating the collector of FIG. 2A when assembled.

In some embodiments, the collector 106 includes a filter or a membrane for generating or separating specifically targeted cells or species from the biological sample. As an example, FIGS. 15A-15C illustrate a plasma membrane 1502 for generating or separating plasma from the biological sample. In some embodiments, the plasma membrane 1502 is disposed within the second segment 208 of the stem portion 204. In some embodiments, the plasma membrane 208 is disposed within the cavity 212 which is formed at the second segment 208 of the stem portion 204. Generally, the plasma membrane 1502 is inserted into the cavity 212 prior to the absorbent member 118, for example, before taking the biological example or at the manufacturing facility site before shipping the device to an end user.

Turning now to FIGS. 3A-3D, there is depicted an exemplary retainer 104 including a vessel 114 and a penetrable seal 116. The vessel 114 as shown has an open top 302 and a closed bottom 304. In some embodiments, the central portion 308 of the closed bottom 304 is recessed inwardly toward the open top 302 for compressing the absorbent member 118. Alternatively, in some embodiments, the central portion 308 of the closed bottom 304 is a protrusion such as a solid column or post protruded inward from the closed bottom 304. Having an inwardly recessed central portion or a protrusion 308 reduces the dead volume and enhances the releasing of the biological sample. For instance, after collection of a biological fluid, the collector 106 is inserted into the housing 102 that contains a retainer 104. As the collector 106 advances into the housing 102, the collector 106 (e.g., the tooth 224) breaks the penetrable seal 116 as illustrated in FIG. 5A, and the absorbent member 118 comes into contact with the inwardly recessed central portion or the protrusion 308 as illustrated in FIG. 5B. As the collector 106 advances further into the housing 102, the inwardly recessed central portion or the protrusion 308 compresses the absorbent member 118 and consequently squeezes the biological sample out of the absorbent member 118.

Having an inwardly recessed central portion or a protrusion formed in the central portion of the vessel 114 has other advantages. For instance, the solution or majority of the solution when stored in the vessel 114 occupies the peripheral space of the vessel 114. Accordingly, the solution can be easily propelled out through the absorbent member 118, further enhancing the release of the biological sample. In some embodiments, the vessel 114 of the retainer 104 is tapered with the open top 302 wider than the closed bottom 304, e.g., the open top 302 has a larger nominal diameter than the closed bottom 304.

In some embodiments, the housing 102 is formed with a means to support the retainer 104. For instance, in some embodiments, the housing 102 is configured to have a seat such as the first seat 404 illustrated in FIGS. 4B and 4D. By way of illustration, the first seat 404 as shown is formed on an interior surface of the housing 102, and supports the retainer 104 once the retainer 104 is inserted into the interior space 112 of the housing 102. Corresponding to the first seat 404, in some embodiments, the vessel 114 is formed with a flange such as the first flange 310 illustrated in FIGS. 3B, 3D and 4D. The flange is preferably formed on an exterior surface of the vessel 114 of the retainer 104 so that when the retainer 104 is inserted into the interior space 112 of the housing 102, the flange abuts the first shoulder. In a preferred embodiment, the first seat 404 is formed in a shape of a shoulder or a flange extruded radially inwardly from the interior surface of the housing 102, and the first flange 310 extends radially outwardly from the exterior surface of the vessel 114 of the retainer 104. The first seat 404 does not necessarily need to be in a contiguous form or circumferentially along the entire periphery of the interior surface of the housing 102. For instance, in an embodiment, the first seat 404 includes a plurality of ribs spaced apart (evenly or unevenly) circumferentially along the interior surface of the housing 102. Similarly, the flange does not necessarily need to be in a contiguous form or circumferentially along the entire periphery of the exterior surface of the vessel 114 of the retainer 104.

Like the body portion 202 and the stem portion 204 of the collector 106, the vessel 114 of the retainer 104 can be made of various materials. For example, the vessel 114 can be made of a variety of materials including but not limited to plastics or metals. Examples of plastics include polypropylene, polyethylene, Polyethylene Terephthalate (PET), polystyrene or polycarbonate. In a preferred embodiment, the vessel 114 is made of a medical grade polypropylene.

The retainer 104 of the present invention can be configured in a variety of shapes and sizes as long as it can be inserted into the housing 102. Preferably, the vessel 114 of the retainer 104 has a cylindrical shape, with a substantially circular or polygonal cross section. In an embodiment, it shapes like a cup. In some embodiments, the vessel 114 of the retainer 104 has a volume between 20 µL and 2000 µL, preferably between 50 µL and 1000 µL, or more preferably between 100 µL and 500 µL.

In some embodiments, the penetrable seal 116 is made of a thermoplastic material, a foil coated thermoplastic material, a heat sealable material, or a material coated with a pressure sensitive adhesive. The penetrable seal 116 is applied onto the vessel 114 by heat.

Figure 4A:
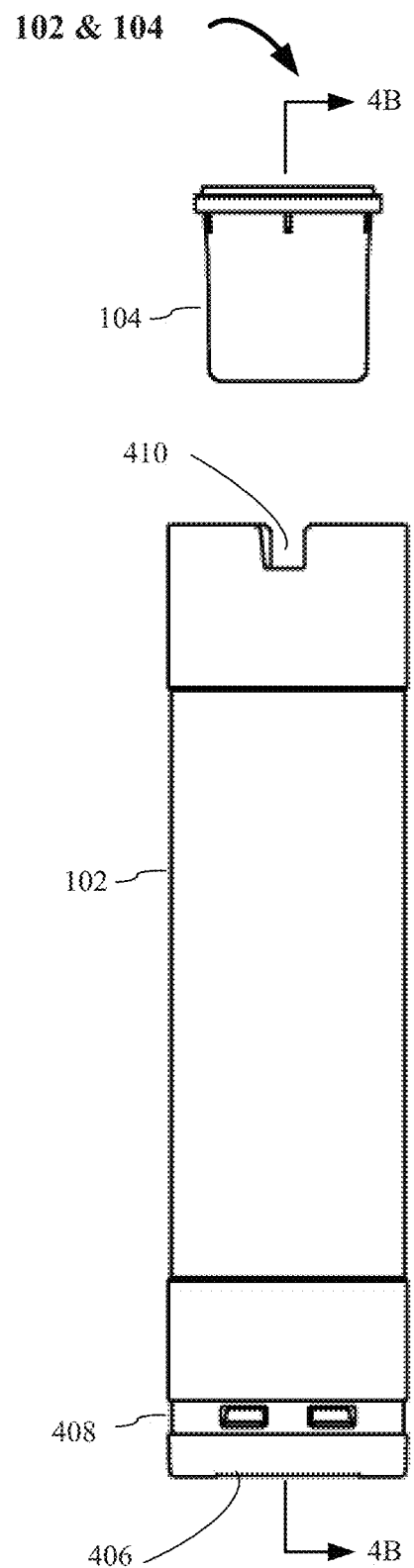
FIG. 4A is an exploded side view illustrating a retainer and a housing in a device for collecting and stabilizing a biological sample in accord with some embodiments of the present invention.
Figure 4B:
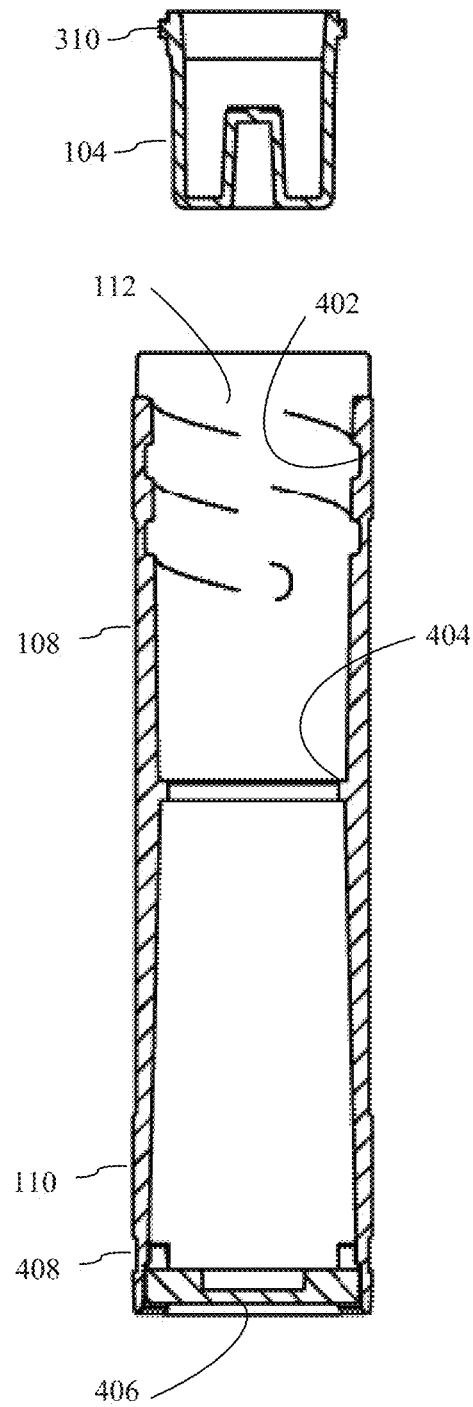
FIG. 4B is a cross-sectional view of FIG. 4B along the line 4B-4B.
Figure 4C:
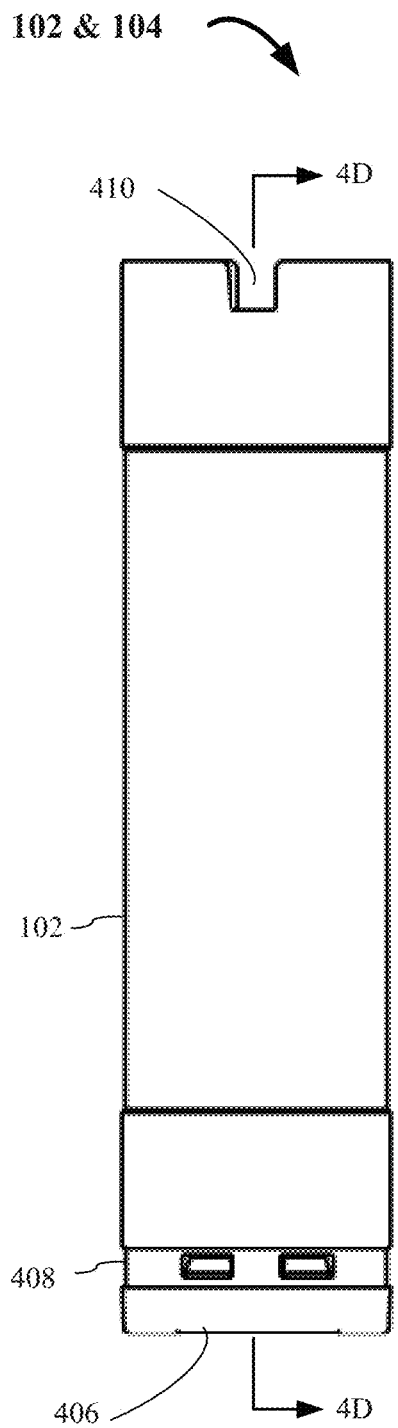
FIG. 4C is a side view illustrating the retainer and the housing of FIG. 4A.
Figure 4D:
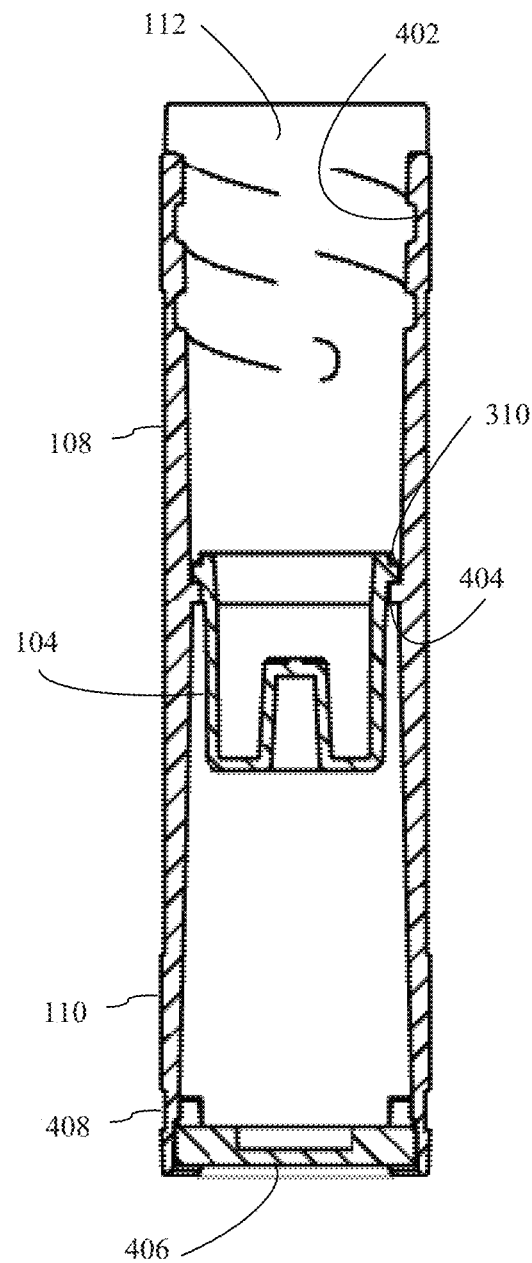
FIG. 4D is a cross-sectional view of FIG. 4C along the line 4D-4D.

FIGS. 4A-4B illustrate an exemplary housing 102 and an exemplary retainer 104 in accordance with some embodiments of the present invention. The housing 102 in general is elongated and has an open end portion 108, an closed end portion 110 and an interior space 112 for accommodating the retainer 104 and engaging with the collector 106. In a preferred embodiment, the housing 102 has a generally cylindrical shape with a substantially circular or polygonal cross section. The housing 102 may be about 4 cm and 12 cm long with an average nominal diameter between 1 cm and 4 cm. In a preferred embodiment, the housing 102 is approximately 7 cm long with an average nominal diameter of approximately 1.8 cm. The housing 102 can be made of various materials, including not limited to plastics and metals. For instance, the housing 102 can be made of polypropylene, polyethylene, Polyethylene Terephthalate (PET), polystyrene or polycarbonate. In one embodiment, the housing 102 is molded with a thermoplastic by injection molding.

In some embodiments, the housing 102 is configured to have optional or additional features. For instance, as described herein, the open end portion 108 of the housing 102 in some embodiments are threaded with internal threads 402 to facilitate engagement with the collector 106 and/or insertion of the retainer 104. In some embodiments, the opening end portion of the housing 102 is also formed with a locking means such as one or more slots for interlocking with the collector 106.

In some embodiments, the housing 102 is configured to have additional features so that the housing 102 can be placed and/or retained in a rack for downstream processing, for example, using a liquid handling robot or other standard automation and testing systems. In one embodiment, the closed end portion 110 of the housing 102 is formed with a groove extended radially inwardly from an exterior surface of the closed end portion 110 of the housing 102. In another embodiment, the closed end portion 110 of the housing 102 is formed with a shoulder or flange extended radially outwardly from the exterior surface of the closed end portion 110 of the housing 102. In yet another embodiment, the closed end portion 110 of the housing 102 is formed with a recess 406 at a bottom of the closed end portion 110 of the housing 102. By way of illustration, FIGS. 4A-4B illustrate a groove 408 and a recess 406 formed at the closed end portion 110 of the housing 102. FIGS. 9A-9D illustrate a ring-like rib or flange 902 and a recess 406 formed at the closed end portion 110 of the housing 102. It is to be understood that the groove, shoulder, flange or recess can take various other configurations including shapes, sizes and locations and in any combination thereof.

In some embodiments, the device 100 includes identification and/or tag for identifying and tracking the device. Examples of identification and tag include a 2D Data Matrix Bar Code, a readable product identification and/or a radio-frequency identification (RFID) tag as illustrated in FIG. 11. In the illustrated embodiment, the Bar Code or the RFID tag is printed on or attached to a bottom of the housing 102, and the product identification is printed on or attached to an exterior surface of the housing 102. It is to be understood that the 2D Data Matrix Bar Code, the readable product and/or the RFID tag can be placed in some other locations, for example, on an exterior surface of the housing 102 proximal to the open end portion 108. It is also to be understood that the device 100 can include other code, identification or information attached, printed, or engraved to the housing 102 or to the collector 106.

Turning to FIGS. 6A-6D, there depicts an alternative exemplary device 600 for collecting and stabilizing biological samples in accordance with some embodiments of the present invention. The device 600 has a number of features that are similar to or substantially the same as those of the device 100. For instance, like the device 100, the device 600 also includes a collector 606, a retainer 604 and a housing 602. The collector 606 includes an absorbent member 118 for collecting the biological sample. The retainer 604 includes a vessel 614 for receiving a solution and a penetrable seal 116 for enclosing the solution within the vessel 614. The housing 602 has an open end portion 608 for engaging with the collector, an closed end portion 610 and an interior space 112 for receiving the retainer.

FIGS. 7A-7D depict an exemplary collector 606 for collecting a biological sample in accordance with some embodiments of the present invention. The exemplary collector 606 is configured to include a body portion 202 as described herein with respect to the collector 106 and a stem portion 702. In the illustrated embodiment, the stem portion 702 includes a first segment 704 proximal to the body portion 202 and a second segment 208 distal to the body portion 202. The absorbent member 118 is attached to, glued on or fitted in the second segment 208 of the stem portion 702. Like the stem portion 204 of the collector 106, in some embodiments, the stem portion 702 is configured to have a partition formed between the first segment 704 and the second segment 208 to prevent the absorbent member from being pushed into the first segment 704 while allowing the released biological sample and the propelled solution flow through and into the first segment 704.

Unlike the stem portion 204 of the collector 106, the first segment 704 of the stem portion 702 is not formed with a reservoir. Instead, the first segment 704 of the stem portion 702 is formed with one or more open slots 706 to allow the released biological sample and the propelled solution flow through.

In accord with the stem portion 702, the retainer 604 is configured to include a reservoir 802, preferably formed adjacent to the open top 302 of the vessel 614, as illustrated in FIGS. 8A-8D. In some embodiments such as those illustrated in FIGS. 10A-10B, the reservoir 802 is configured to receive the first segment 704 of the stem portion 702. Together with the first segment 704 of the stem portion 702, the reservoir 802 facilitates the mixing of the biological sample with the solution and stores the mixture of the biological sample and the solution.

Figure 8G:
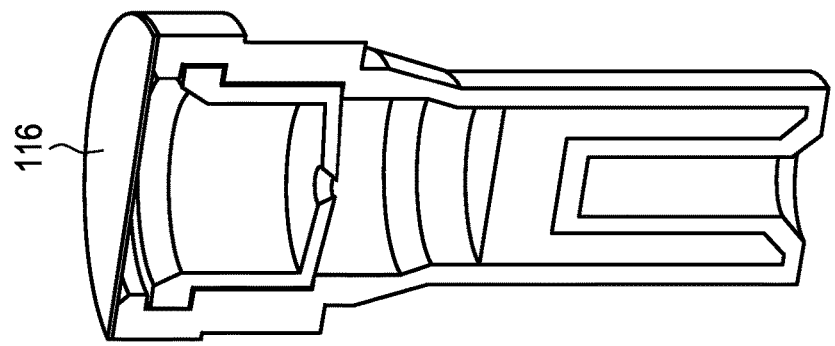
FIG. 8G is a cutout view illustrating the retainer of 8F.
Figure 8F:
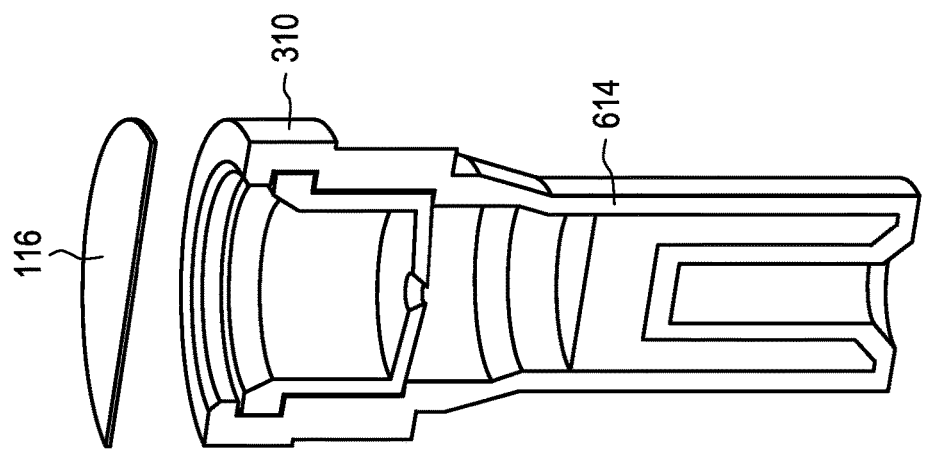
FIG. 8F is a cutout partially exploded view illustrating a retainer in a device for collecting and stabilizing a biological sample in accord with some embodiments of the present invention.
Figure 8E:
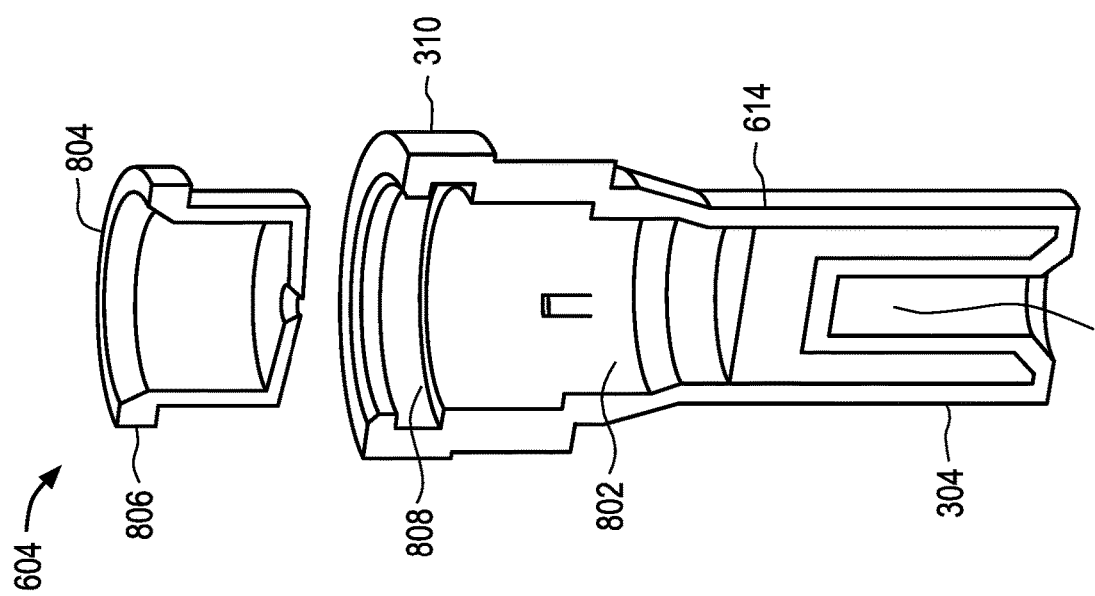
FIG. 8E is a cutout partially exploded view illustrating a retainer in a device for collecting and stabilizing a biological sample in accord with some embodiments of the present invention.
Figure 9A:
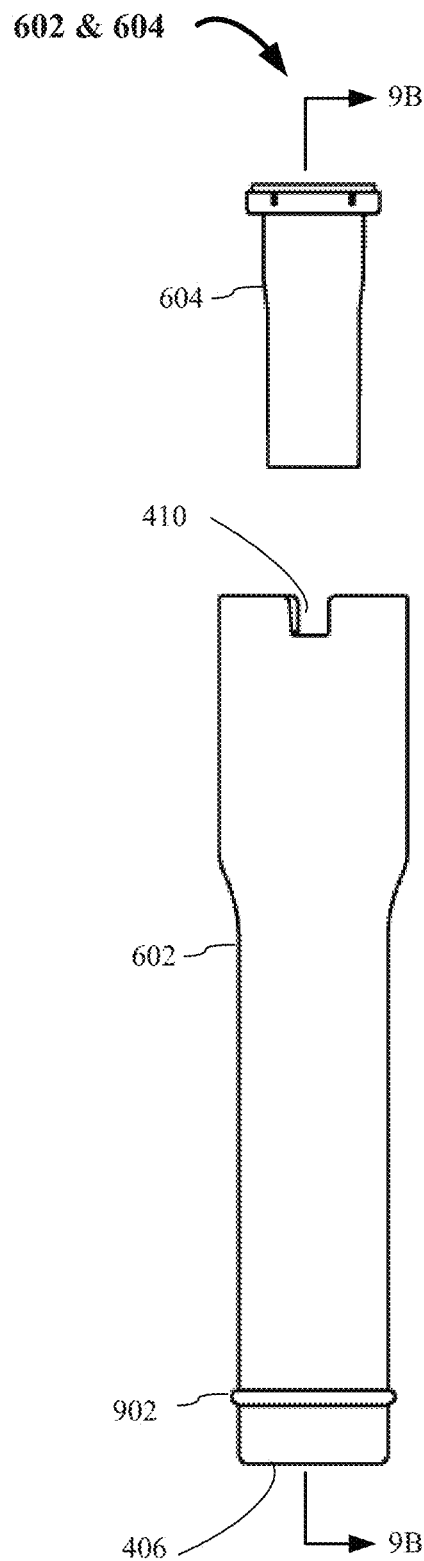
FIG. 9A is an exploded side view illustrating a retainer and a housing in a device for collecting and stabilizing a biological sample in accord with some embodiments of the present invention.
Figure 9B:
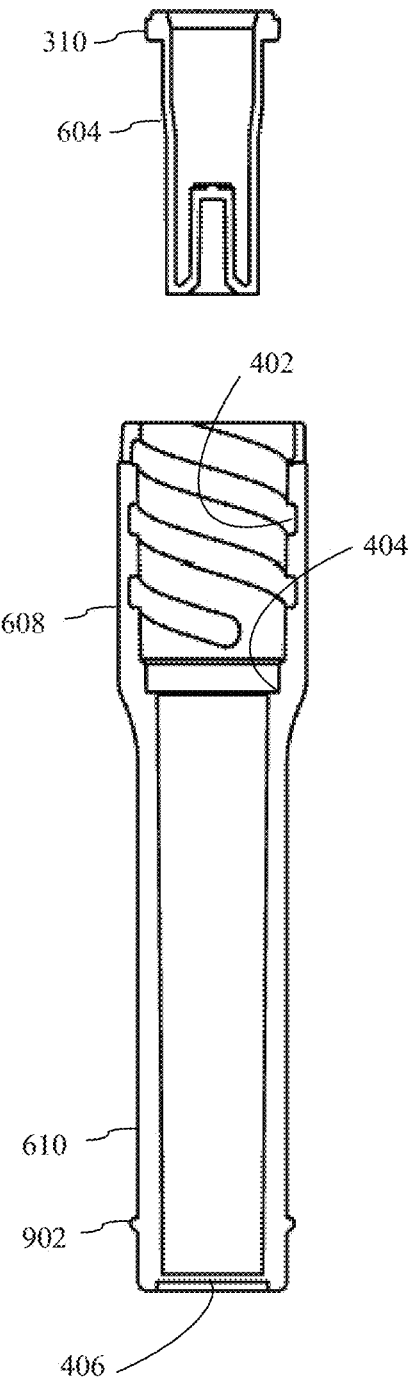
FIG. 9B is a cross-sectional view of FIG. 9B along the line 9B-9B.
Figure 9C:
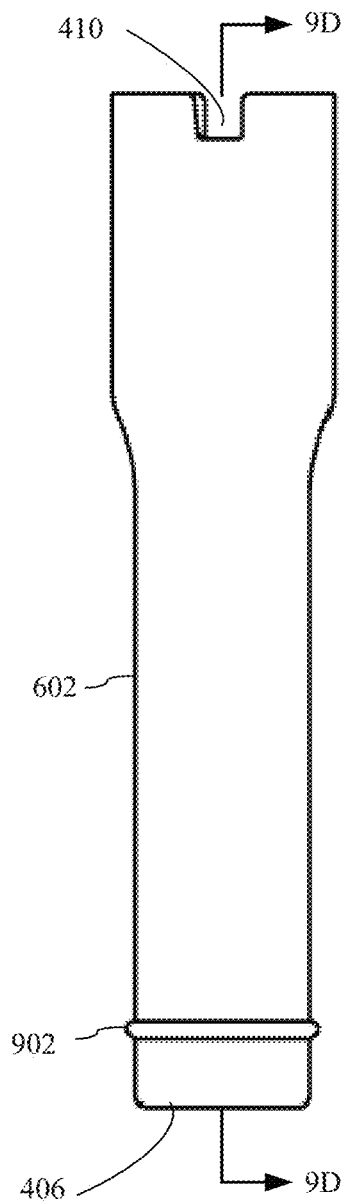
FIG. 9C is a side view illustrating the retainer and the housing of FIG. 9A.
Figure 9D:
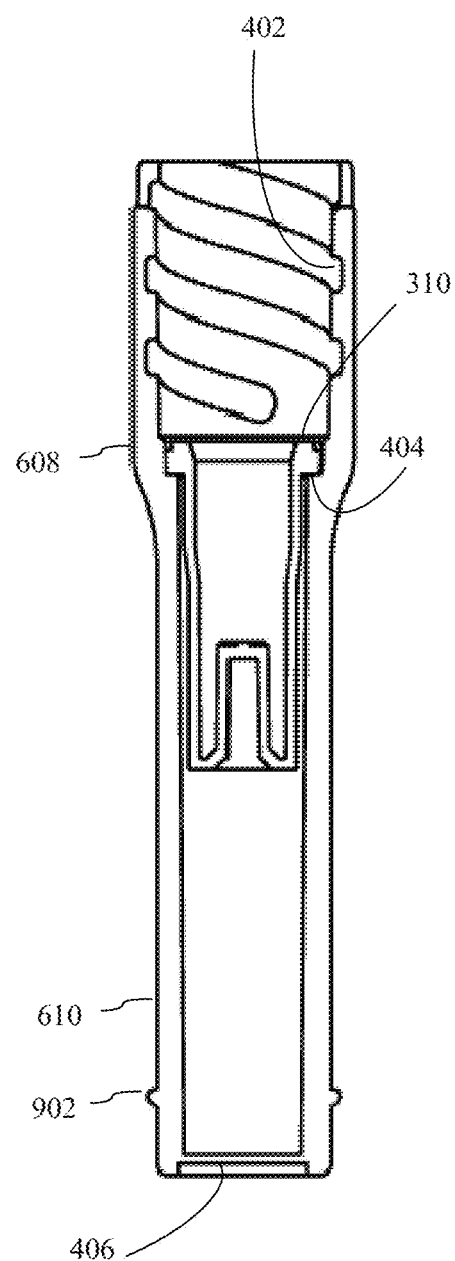
FIG. 9D is a cross-sectional view of FIG. 9C along the line 9D-9D.

In some embodiments, the retainer 604 includes a retention, such as the retention 804 illustrated in FIGS. 8E-8G, to retain the solution within the retainer 604. The solution retention 804 is preferably disposed between the solution received in the vessel and the penetrable seal. As shown in FIGS. 8E-8G, after the solution is received in the vessel, the solution retention 804 can be pushed into the vessel before sealing the vessel 614 with the penetrable seal 116. To support the solution retention 804, in some embodiments, the vessel 614 is configured with a seat or shoulder 808 formed on an interior surface of the vessel 614. Correspondingly, the solution retention 804 is configured with a flange 806 formed on an exterior surface of the solution retention 804. When the solution retention 804 is pushed into the vessel 614, the flange 806 abuts the seat or shoulder 808, thereby supporting the solution retention 804 in place and preventing the solution retention 804 from being pushed into the solution.

Turning now to FIG. 12, there depicts an exemplary kit for collecting and stabilizing a biological sample in accord with some embodiments of the present invention. The kit can be used at an end user's home, a homecare, or other facilities. It allows a user to self-collect a biological sample at his/her location (e.g., home) and then mail the sample, for instance, to a testing lab for subsequent processing. It is to be understood that the kit can also be used by a healthcare professional (e.g., a nurse) or other personnel to take a sample.

The kit in general includes a collector (e.g., collector 106, 606), a retainer (e.g., retainer 104, 604) and a housing (e.g., housing 102, 602). The retainer can be made separately and pre-assembled with the housing before shipping the kit to an end user. Preferably, the retainer is assembled with the housing at a manufacturing site.

In some embodiment, the kit also includes one or more lancets 1202, for example, two lancets as illustrated in FIG. 12. The lancets 1202 can be used for penetrating a membrane of an end user (e.g., a skin of a finger) to provide the biological sample (e.g., blood). In some embodiments, the kit includes a casing 1204 such as a box for accommodating the collector, the housing with the retainer, and/or the lancets. In some embodiments, the kit includes other optional or additional components. For instance, in some embodiments, the kit includes one or more preparation pads 1206 for cleaning and preparing a collection site (e.g., finger, foot) prior to collecting the biological sample. The preparation pads may be alcohol disinfectant pads. In some embodiments, the kit includes one or more band-aids 1208 for protecting the collection site after collecting the biological samples.

Figure 13:
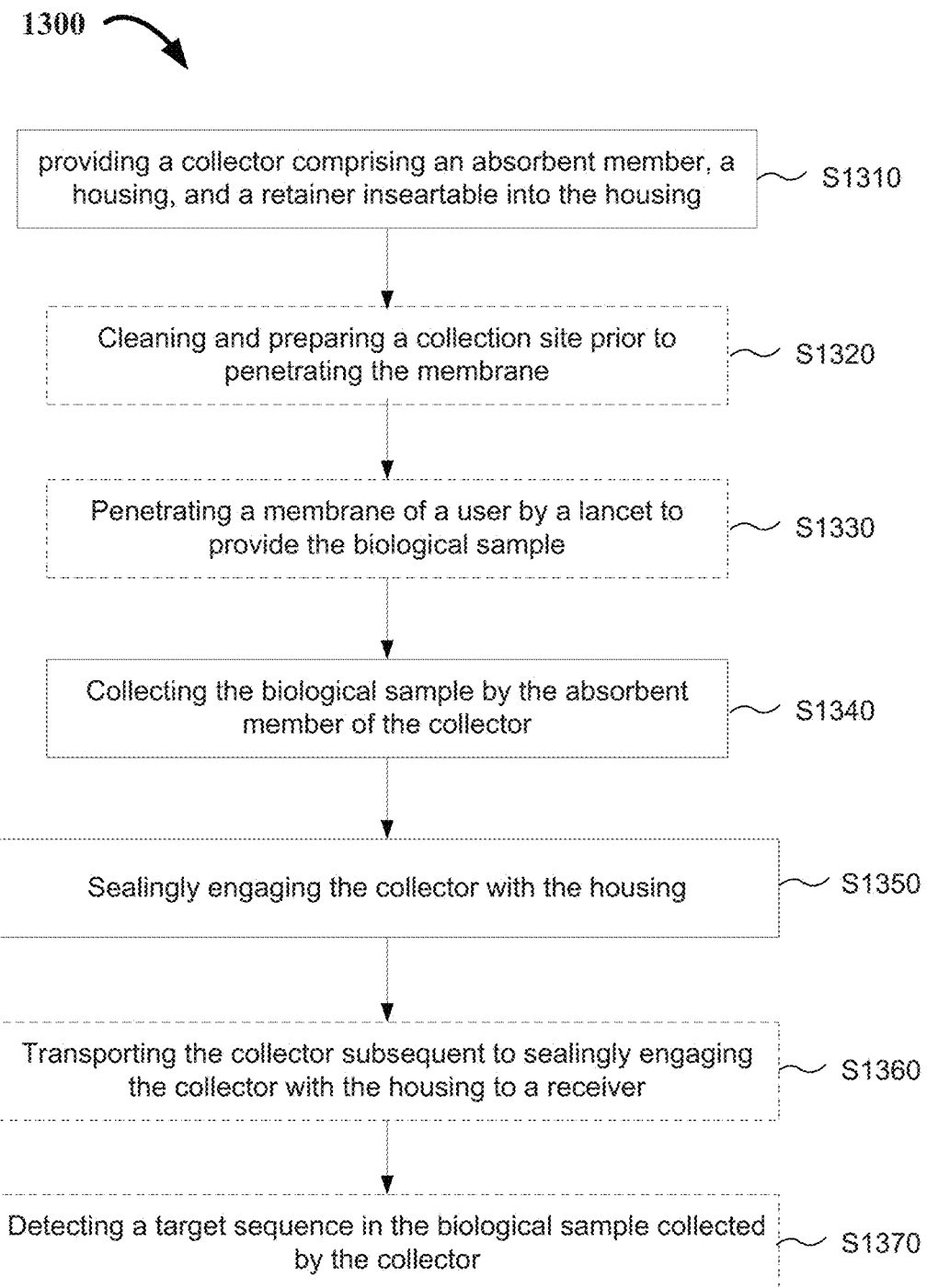
FIG. 13 is a diagram illustrating a method for collecting and stabilizing a biological sample in accord with some embodiments of the present invention.

The collection and stabilization device and kit of the present invention can be used in a variety of applications. For instance, the collection and stabilization device and kit can be used to collect and stabilize blood or other bodily fluids from a patient's fingertip, earlobe, heel or other locations. By way of illustration, FIG. 13 is a flow chart illustrating an exemplary method using the devices or the kits of the present invention to collect and stabilize a biological sample. In some embodiments, the method includes step S1310 of providing a collector comprising an absorbent member, a housing, and a retainer insertable into the housing, step S1340 of collecting the biological sample by the absorbent member of the collector, and step S1350 of sealingly engaging the collector with the housing. The retainer contains a solution and has been inserted into an interior space of the housing prior to engaging the collector with the housing. As described herein with respect to the device 100, 600, the sealingly engaging of the collector with the housing breaks a penetrable seal of the retainer and propels the solution retained in the retainer to flow through the absorbent member. Consequently, the biological sample (or a percentage or certain components of the biological sample) is released from the absorbent member and mixed with the solution to form a stabilized mixture of the biological sample with the solution.

Figure 10A:
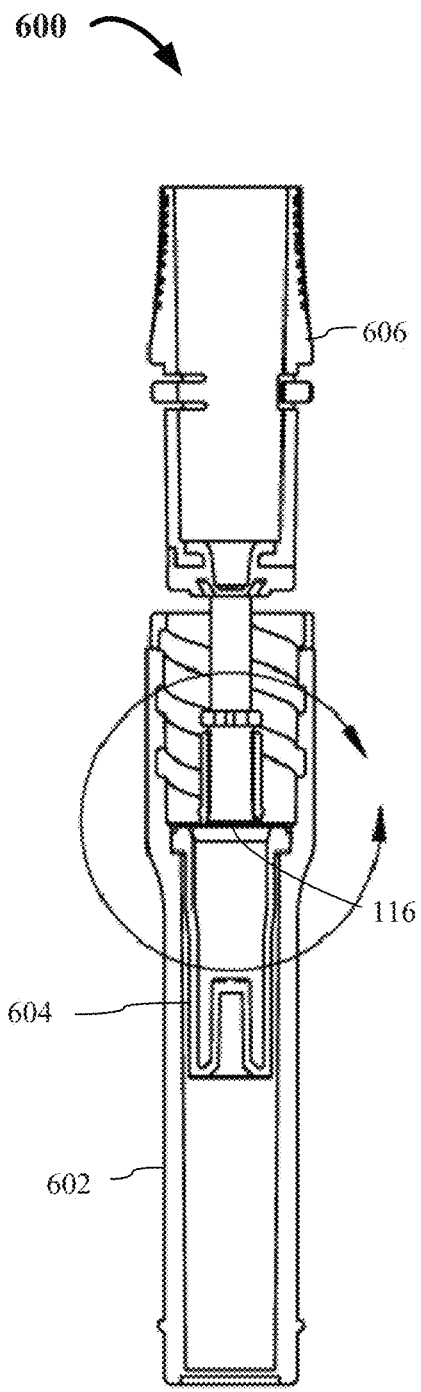
FIG. 10A, FIG. 10B, FIG. 10C and FIG. 10D are cross-sectional views illustrating a device for collecting and stabilizing a biological sample in accord with some embodiments of the present invention, where a collector is engaging with a housing at different stages.
Figure 10B:
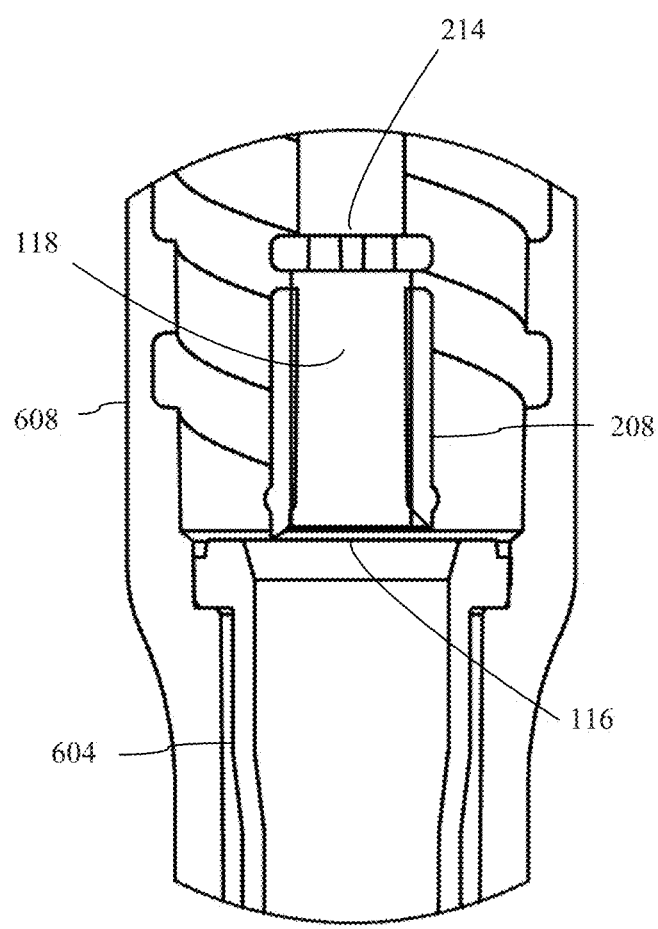
Figure 10C:
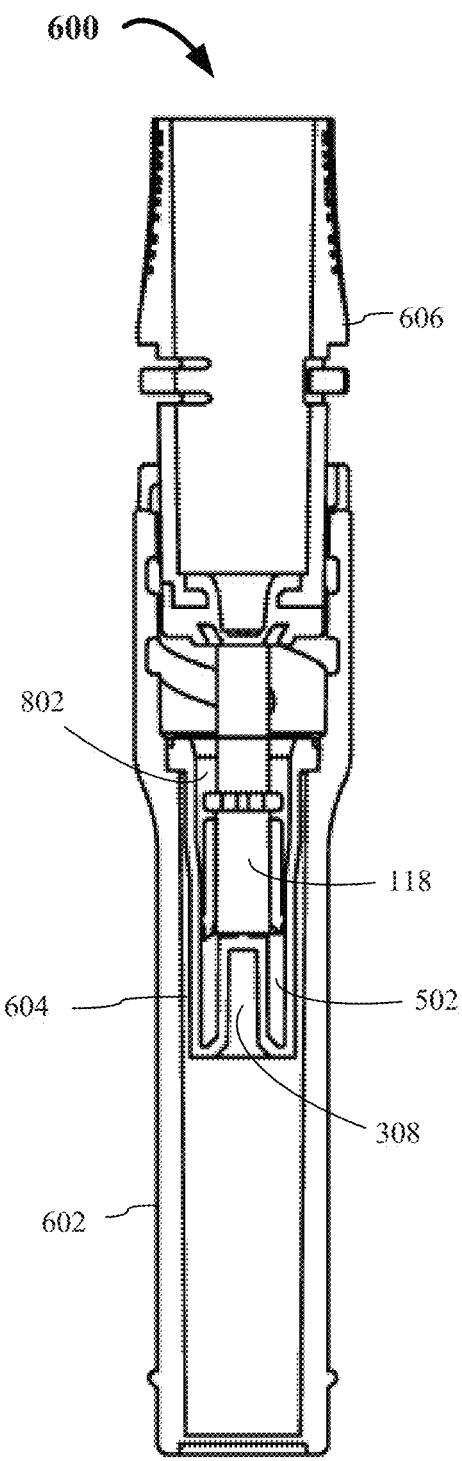
Figure 10D:
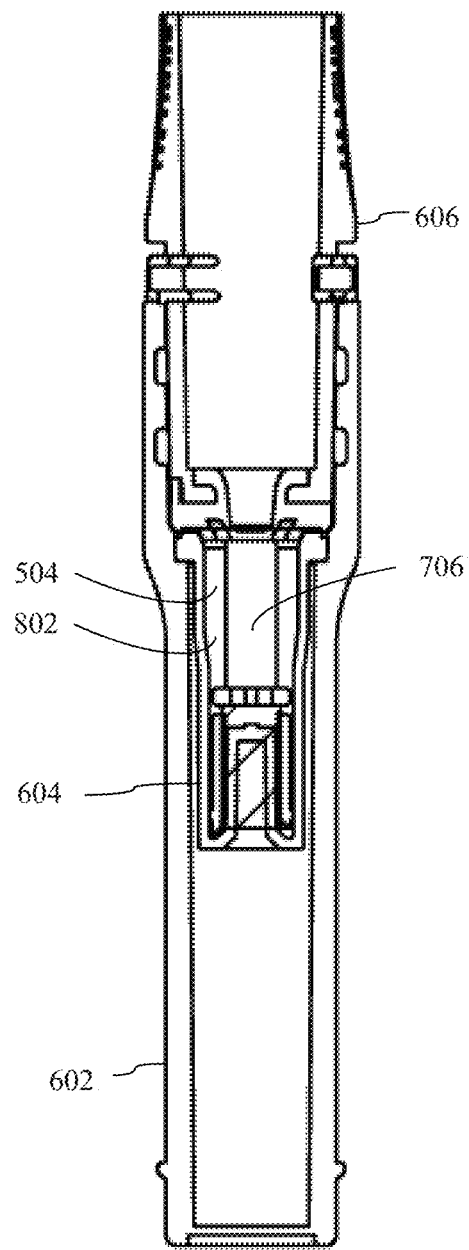

In some embodiment, the sealingly engagement involves screwing the collector into the housing. As it advances down into the housing, the collector pierces the sealing film of the retainer, exposing the absorbent member to the solution 502 in the retainer, as illustrated in FIGS. 5A and 10A-10B. As the collector advances further down into the housing, the absorbent member comes into contact with the inwardly recessed central portion or the protrusion as illustrated in FIGS. 5B and 10C. The screwing process of the collector continues, and the absorbent member is compressed until it hits a hard stop, as illustrated in FIGS. 5C and 10D. At this point, in some embodiments, the interlocking mechanism engages, prohibiting unintentional removal of the collector from the housing.

In some embodiments, the method includes some optional or addition steps. For instance, prior to collecting the biological sample, a user or a professional may use a lancet to penetrate a membrane of a user at a collection site (e.g., pierce a fingertip or foot) at step S1330. In some embodiments, prior to penetrating the membrane, the collection site is cleansed and prepared, for example, by a preparation pad and preferably a pre-prepared alcohol pad at step S1320. After the collector is sealingly engaged with the housing, the device along with the housing and the retainer is shipped or transported to a receiver (e.g., a testing lab, a provider) at step 1360. Once the collector is received, the biological sample can be retrieved, for example, by a pipette, for subsequent processing at step S1370. In some embodiments, the subsequent processing includes detecting a target sequence in the biological sample collected by the collector.

Figure 14:
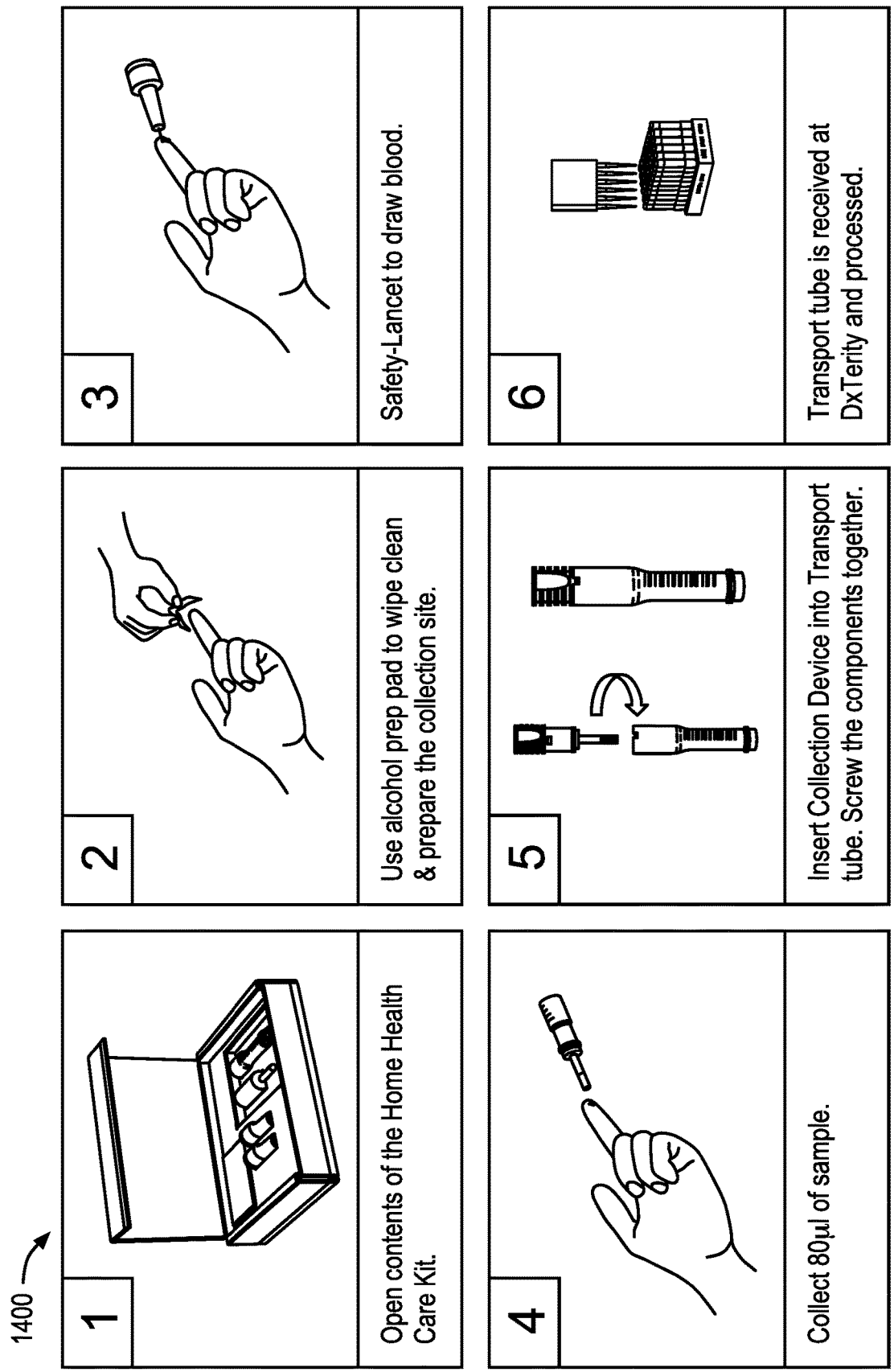
FIG. 14 is a diagram illustrating a method for collecting and stabilizing a biological sample in accord with some embodiments of the present invention.

FIG. 14 illustrates an exemplary method 1400 using the devices or the kits of the present invention to collect and stabilize blood from a fingertip. In some cases, it is preferable to wash hands thoroughly with soap and warm water and then use the alcohol prep pad to wipe clean and prepare the collection site before puncturing the fingertip. After the preparation, place the tip of the lancet onto the collection site of the targeted fingertip and press the trigger to draw blood. Touch the collector (e.g., the absorbent member in the cavity of the collector) to the collection site to absorb the blood. In some case, it is preferable to massage the finger to maintain the flow of blood so as to ensure collection of a predetermined amount (e.g., 80 μL) of the blood. Once the predetermined amount of the blood is collected or the absorbent member reaches its full capacity, insert the collector (or the stem portion of the collector) into the housing and screw the collector until it is fully engaged with the housing. Ship the collector along with the housing to a receiver (e.g., testing lab) for subsequent processing.

Detection of Samples

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, phage display, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as Genome Analysis: A Laboratory Manual Series (Vols. I-IV), Using Antibodies: A Laboratory Manual, Cells: A Laboratory Manual, PCR Primer: A Laboratory Manual, and Molecular Cloning: A Laboratory Manual (all from Cold Spring Harbor Laboratory Press), Stryer, L. (1995) Biochemistry (4th Ed.) Freeman, New York, Gait, "Oligonucleotide Synthesis: A Practical Approach" 1984, IRL Press, London, Nelson and Cox (2000), Lehninger, Principles of Biochemistry 3rd Ed., W. H. Freeman Pub., New York, N.Y. and Berg et al. (2002) Biochemistry, 5th Ed., W. H. Freeman Pub., New York, N.Y., all of which are herein incorporated in their entirety by reference for all purposes.

The present systems are directed to the collection of biological samples, particularly blood, that contain sufficient cells (including viruses) to do molecular diagnostic analyses.

As will be appreciated by those in the art, there are a number of existing technologies that are used in molecular diagnostics, any one of which can be done on the collected samples of the invention, including PCR (real-time, multiplex, digital, etc.), microarray analysis, capillary electrophoresis, etc.

In one embodiment, the samples are processed using chemical ligation, which is generally described in US Publications No. US Pub. Nos 2010/267585 and 2013/0005594, hereby expressly incorporated by reference in its entirety and particularly for the Figures and Legends, the discussion of the buffers, ligation moieties, and orientation of the ligation probes.

Figure 16:
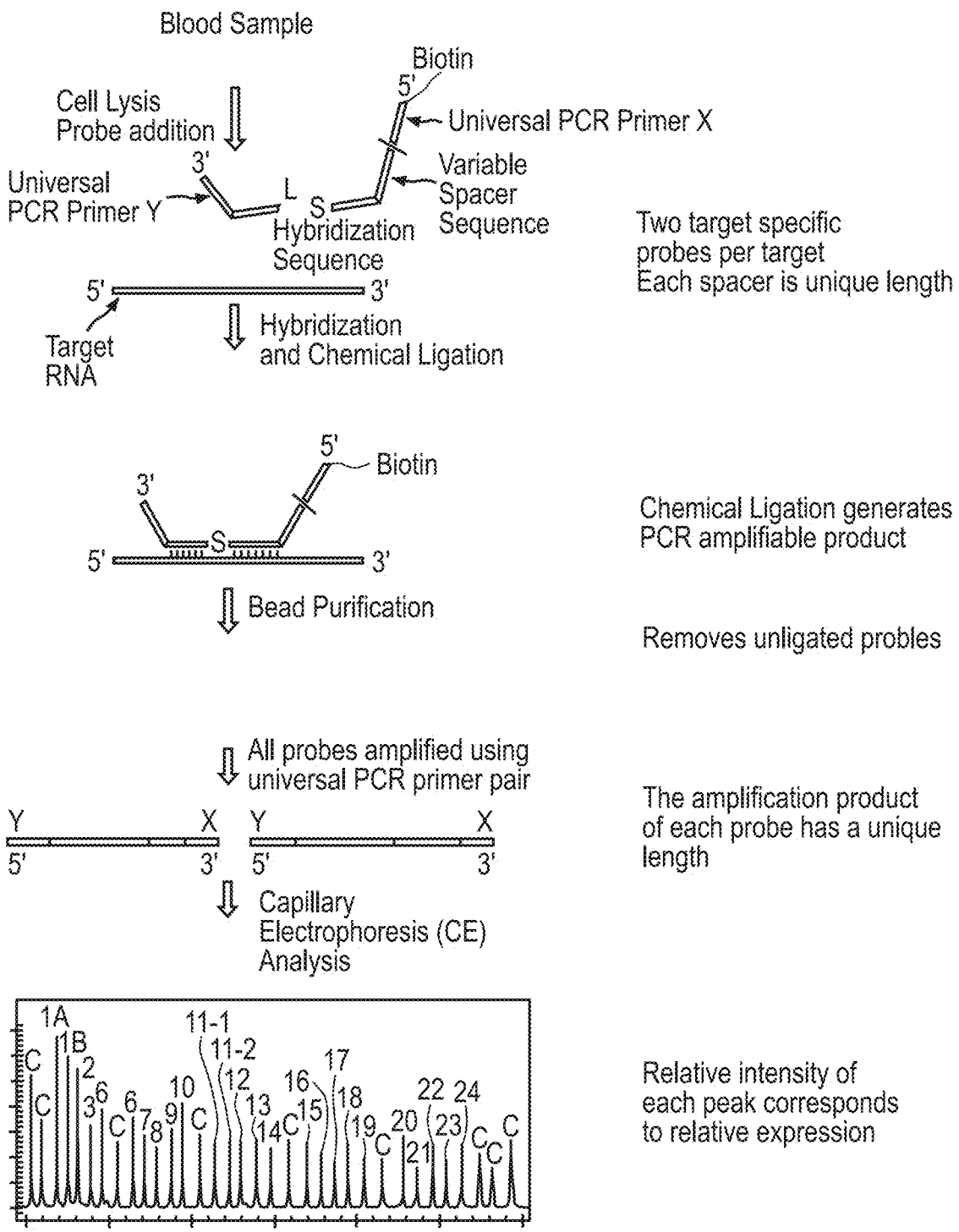
FIG. 16 is a schematic overview of one method of detecting nucleic acids from the target sample that utilizes the chemical ligation dependent probe amplification ("CLPA") reaction as discussed in US Pub. Nos 2010/0267585 and 2013/0005594, both of which are incorporated by reference in their entirety, specifically but not limited to the discussions of CLPA assays and components, including probes, assays, buffers (reaction buffers, stabilization buffers, etc.). In this embodiment, the assay shows a blood sample, although as will be understood by those in the art and described herein, additional sample types can be used. The figure shows a two probe system, although as shown in FIG. 3 of US 2010/0267585, three (or more) probe systems can be used.
Figure 17:
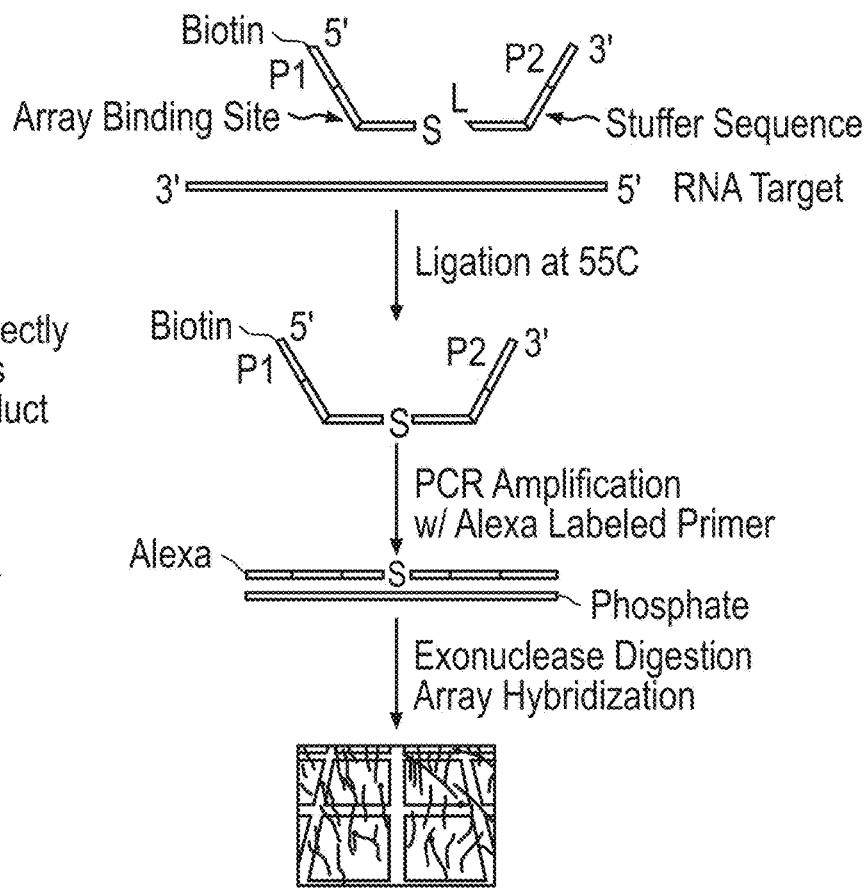
FIG. 17 is a schematic overview of a CLPA-MDM process, where a solid support system is used for detection (e.g. an array or array of beads). In this embodiment, it is preferred that at least one of the ligation probes for incorporate an array binding sequence to bind to an appropriate capture sequence on a microarray platform. For CLPA-MDM, the different CLPA reaction products are not separated by size differences but by the differences in the array binding sequence. In this embodiment, the sequence of the array binding sequence is varied so that each CLPA probe will bind to a unique site on a DNA microarray. The length of the array binding sequence in CLPA-MDM usually varies from 15 to 150 bases, more specifically from 20 to 80 bases, and most specifically from 25 to 50 bases.
Figure 18:
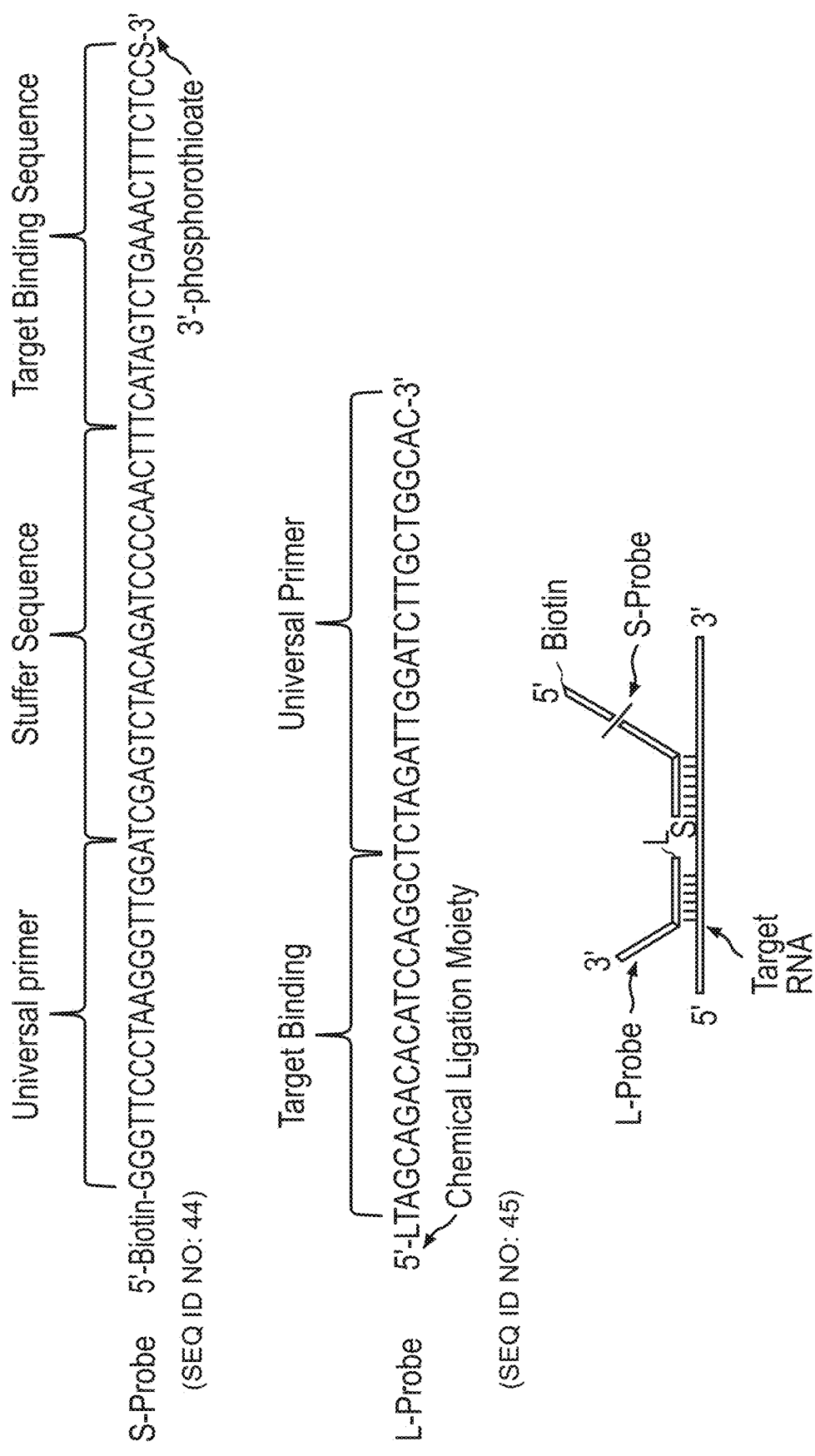
FIG. 18 is a schematic representation showing probe design for a CLPA assay in which the probe contains a size-variant stuffer sequence.
Figure 19:
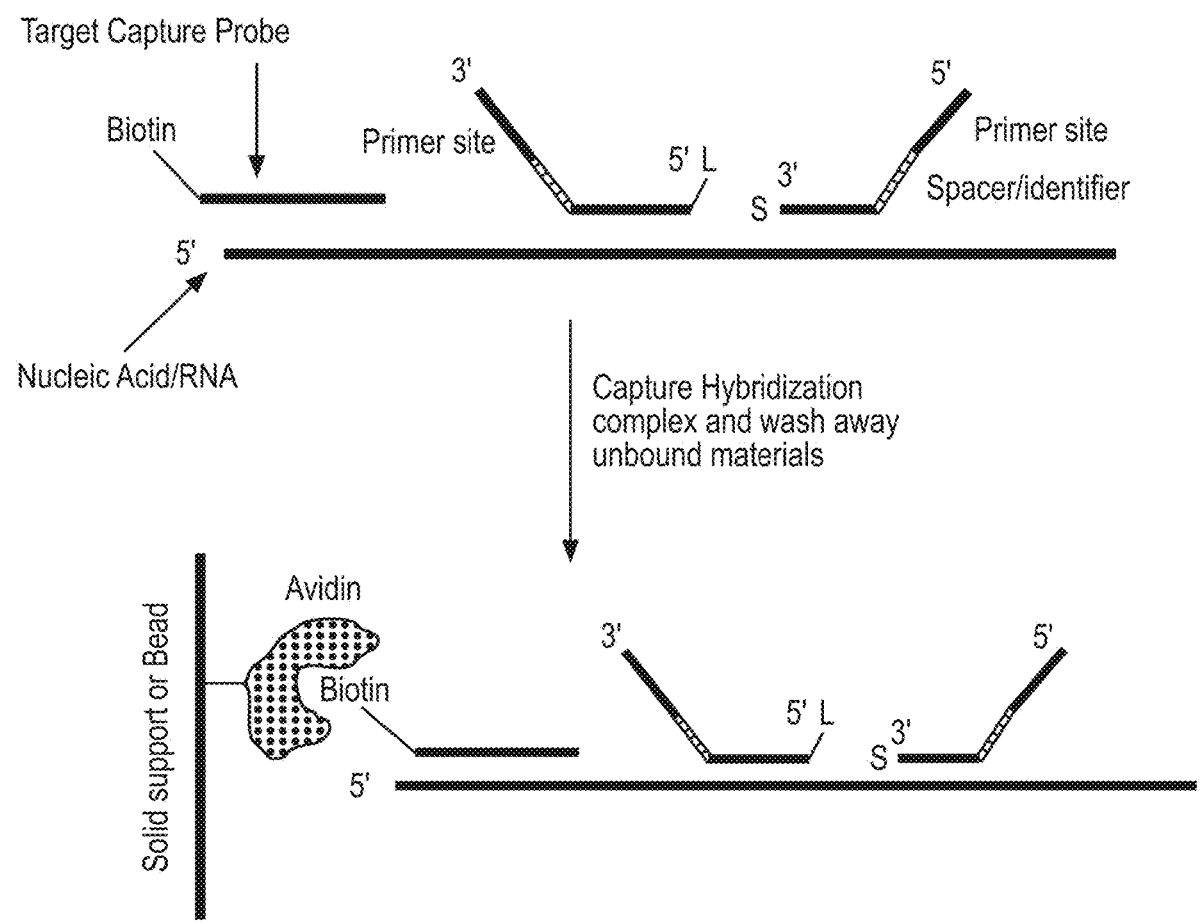
FIG. 19 is a schematic representation of a target capture method used to separate bound CLPA probe sets from solution phase/unbound CLPA probe sets.
Figure 20:
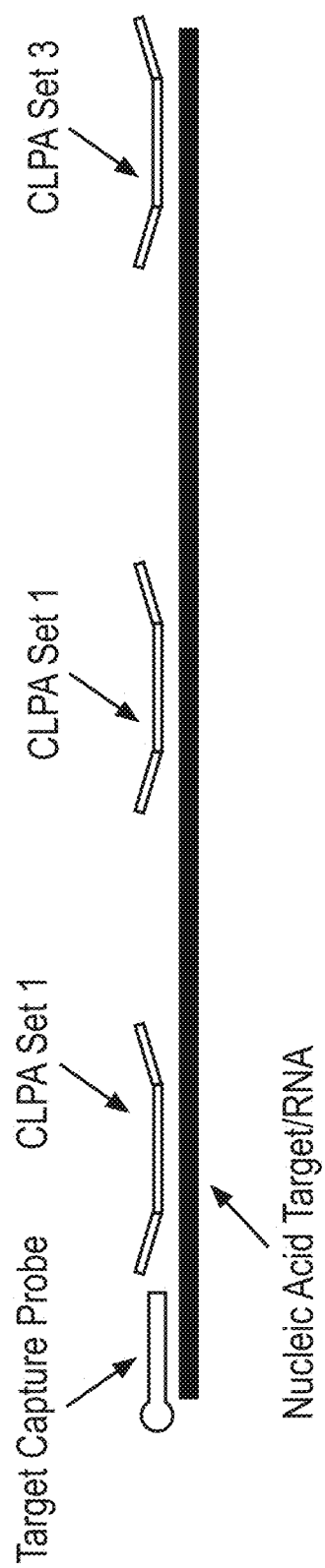
FIG. 20 is a schematic illustration of multiple, unique CLPA probe sets that are bound to the sample target along with a single target capture probe.
Figure 21A:
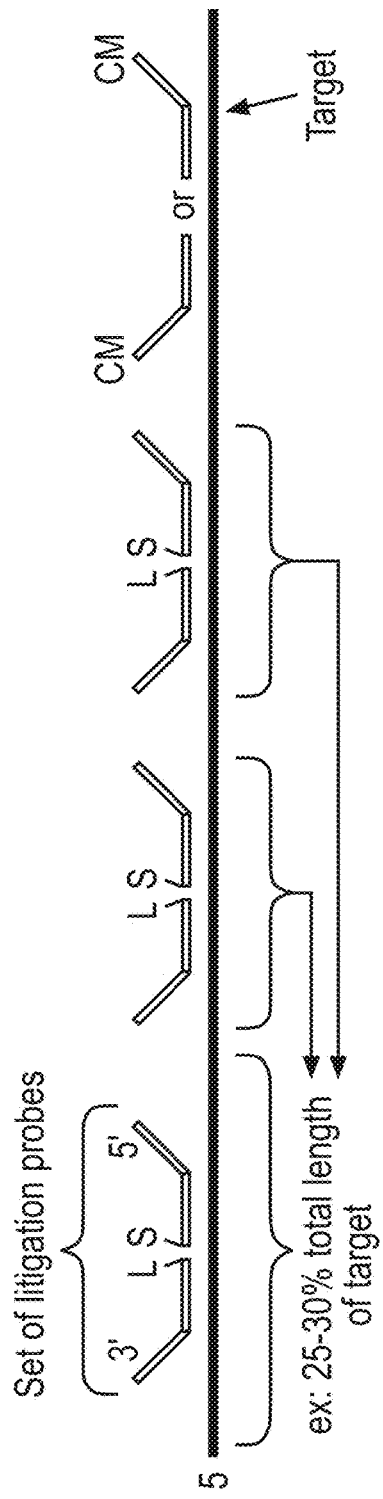
FIG. 21A, FIG. 21B and FIG. 21C are further schematic illustrations of the use of a CLPA assay, showing possible orientations of the assay which can find particular use in assessing sample integrity.
Figure 21B:
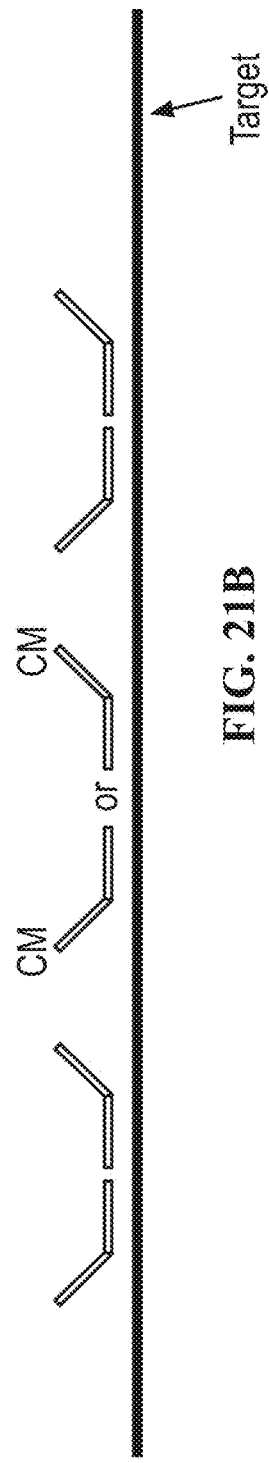
Figure 21C:
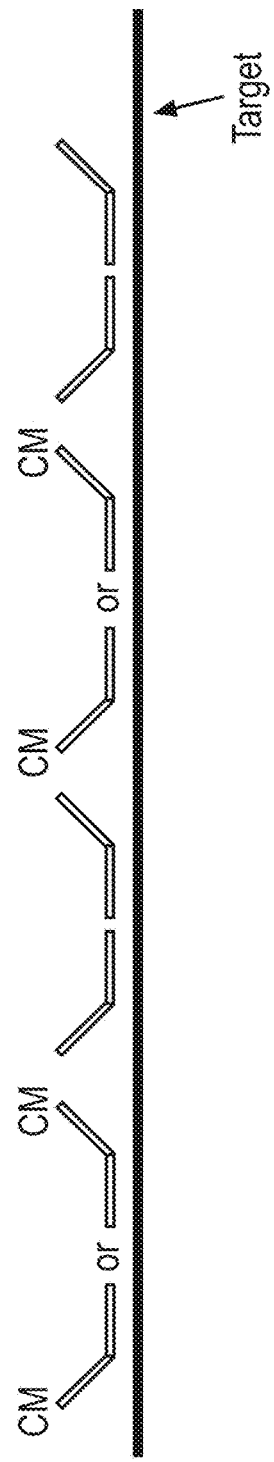
Figure 22A:
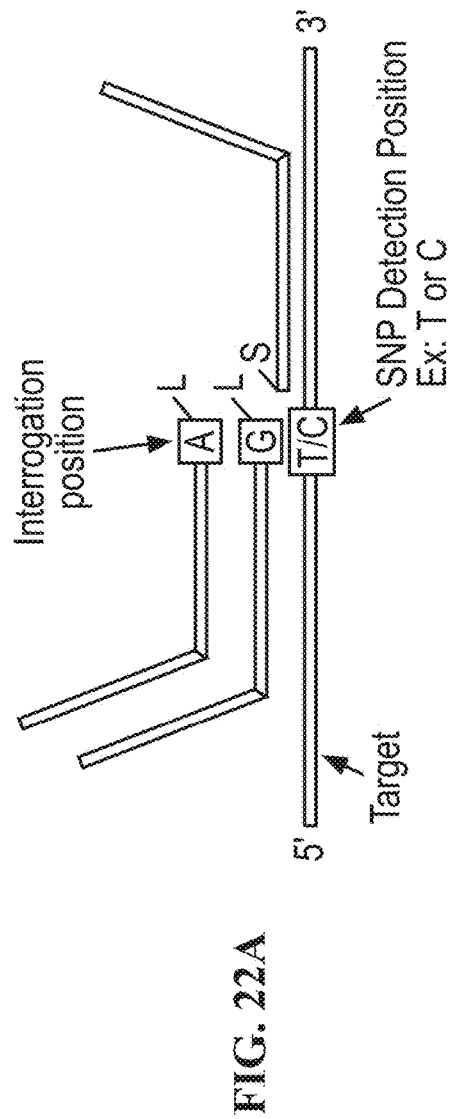
FIG. 22A, FIG. 22B and FIG. 22C depict several schematics of CLPA detection methods for use in SNP detection methods.
Figure 22B:
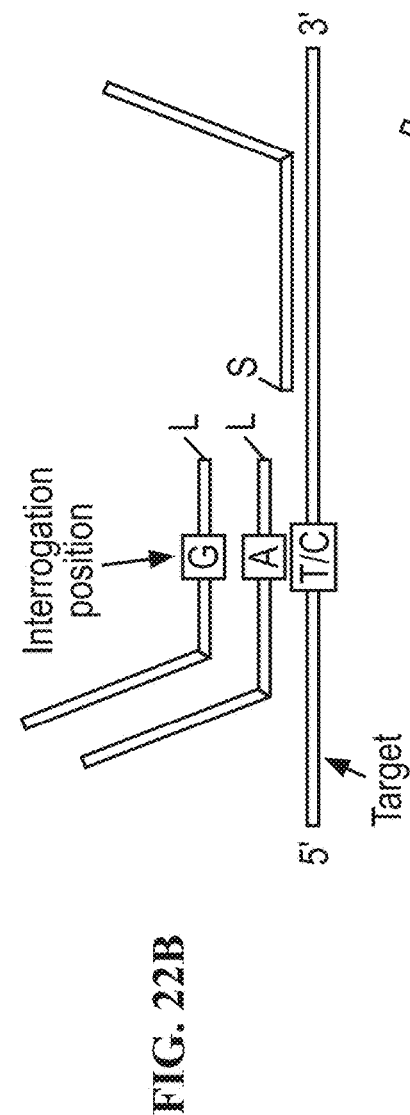
Figure 22C:
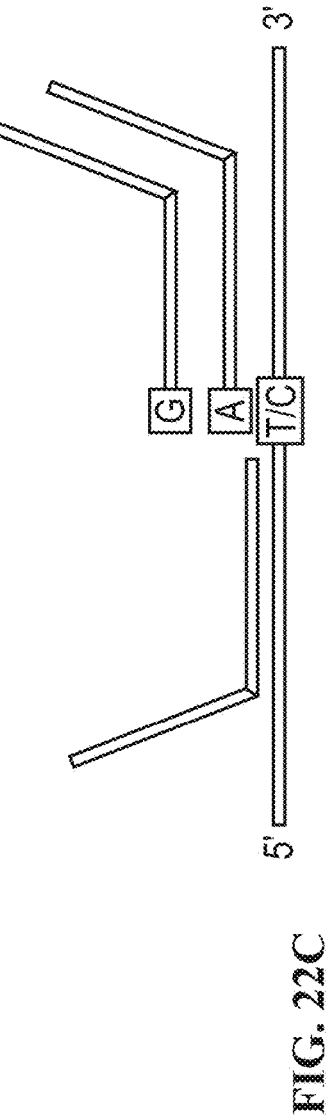

As depicted generally in FIG. 16, in CLPA, the methods utilize two or more ligation probes (also referred to herein as "oligonucleotide probes") that reversibly bind a target nucleic acid in close proximity to each other and possess complementary reactive ligation moieties. In the ligation reaction, when the probes have bound to the target in the proper orientation, they are able to undergo a spontaneous chemical ligation reaction that yields a ligated oligonucleotide product that does not rely on the use of a ligase enzyme. The presence of the target(s) of interest can then be determined by measuring the presence or amount of ligated oligonucleotide product (also referred to herein as a "ligation product") in a number of different ways. As is described below, the ligation probes can contain a variety of additional functionalities, including, but not limited to, detectable labels to aid in the identification, quantification or detection of the ligated oligonucleotide product, including, for example, direct labels such as optical (including fluorescent labels, particularly covalently attached fluorescent labels such as are known in the art), and electrochemical labels, etc., as well as optional variable spacer sequences or "size tags" comprising nucleic acid sequences that are sized to be specific for a particular target, such that detecting ligation products (or amplicons generated from such ligation products) of a particular size identifies the presence and/or amount of a particular target nucleic acid sequence (for example for use in capillary electrophoresis (CE) analysis as shown in FIG. 15, which is one (non-limiting) method of detection. Another optional functionality for inclusion in one or more of the ligation probes are capture moieties designed for subsequent capture on a solid support (e.g. microarrays, microbeads, nanoparticles, etc.), which include, but are not limited to, binding partners such as biotin, anchoring oligonucleotide sequences (also referred to herein as "anchor sequences" or "capture sequences") molecular handles that promote the concentration or manipulation of the ligated product (magnetic particles, oligonucleotide coding sequences), and promoter and primer sequences to facilitate subsequent secondary amplification of the ligated product via an enzyme like a DNA or RNA polymerase.

Preferably, the ligation reactions of the invention do not require the presence of exogeneously added ligases, nor additional enzymes, although some secondary reactions may rely on the use of enzymes such as polymerases, as described below. Amplification of the target may also include turnover of the ligation product, in which the ligation product has a lower or comparable affinity for the template or target nucleic acid than do the separate ligation probes. Thus, upon ligation of the hybridized probes, the ligation product is released from the target, freeing the target to serve as a template for a new ligation reaction. Alternatively, thermal cycling can be done to remove a ligation product from the target sequence and allow new ligation probes to hybridize for another cycle of ligation.

The invention provides compositions, apparatus and methods for the detection of one or more nucleic acid targets in a sample including, but not limited to, DNA and RNA targets. Advantages of using non-enzymatic approaches for nucleic acid target detection include lower sensitivity to non-natural DNA analog structures, ability to use RNA target sequences and lower cost and greater robustness under varied conditions. In particular, the methods described herein do not require significant sample preparation; that is, the ligation reactions can be performed in the presence of contaminants and buffers that would inhibit or inactivate enzymatic processes for detection. For example, blood samples can be collected into highly denaturing stabilization buffers, the probes added and the reactions occur, under conditions that would denature an enzymatic process. This ability to analyze target nucleic acids, particularly RNA, in impure samples is of particular use in applications such as medical diagnostics (including gene expression profiling and SNP detection), forensic applications, and testing for damage due to environmental toxins and/or radiation. In addition, methods and compositions of the present invention are useful in detection of nucleic acids from samples that are degraded, including paraffin-embedded samples in which the process of fixing and embedding in paraffin resulted in degradation of the samples' nucleic acids.

In addition, one embodiment of the invention provides for assays relating to target nucleic acid "integrity". That is, as is known in the art with mRNA, for example, or nucleic acids in fixed samples, the nucleic acids are degraded over time. As is shown in the figures, if chemical ligation is used for detection, multiple ligation complexes are used to allow for an assessment of the integrity of the sample. Similarly, the use of these multiple ligation complexes per target sequence can also be used for data and assay integrity through redundancy, similar to running samples in duplicate or triplicate, for example.

In further aspects, the collection system of the present invention provides buffers that serve to stabilize nucleic acids in a sample and other functionalities. In some embodiments, the device contains reagents which stabilize nucleic acids (also referred to herein as "sample nucleic acid" or "target nucleic acids"). By "stabilize" as used herein is meant that the nucleic acids in a sample are resistant to degradation even when stored at ambient room temperature or above for a period of time. In some embodiments, nucleic acids contained in buffers of the invention are stable at room temperature or above for about one day to about three months. Stability can be measured using any means known in the art, including assays for nucleic acid integrity as further discussed below. In further embodiments, a sample comprising nucleic acids contained in a buffer of the invention is assessed as having increased stability as compared to a sample that was not stored in the buffer if at least 10%, 20%, 30%, 40%, 50%, 60%, 70%, 80%, 90%, 95% of the nucleic acids in the sample stored in the buffer show less degradation than those in the sample that was not stored in the buffer. In yet further embodiments, a sample is identified as being stabilized by the buffers of the present invention if at least a majority of the nucleic acids in the sample show reduced degradation as compared to a sample that was not stored in the buffer. Stability of RNA samples are often assessed by Capillary Electrophoresis methodologies that look to measure the average size of the nucleic acid sample. Stabilized samples will have a longer average size than non-stabilized samples. Another aspect included herein is the use of multiple ligation probe sets combined with one or more target capture probes that can be used to assess the average size of a target nucleic acid, and by correlation, the level of degradation of the target nucleic acid.

Buffers of the invention can optionally and in any combination include one or more of a denaturant, a reducing agent, a surfactant, a pH buffer, a chelator such as EDTA, and any combination thereof. As will be appreciated, buffers of the invention may include multiple types of components within the same class—e.g., buffers of the invention may include one or more different kinds of denaturants in combination with one or more types of surfactants, and so on.

An advantage of the buffers of the present invention is that they can be used to stabilize nucleic acids such as RNA in a sample and then the sample can be directly analyzed from the buffer solutions in accordance with the methods described herein. In other words, samples contained in buffer solutions of the invention can be subjected to the chemical ligation and detection methods described herein without isolation or purification of the RNA. Another advantage of the buffers of the invention is that cell lysis occurs upon the collection of the sample in the buffer, thus not requiring an additional lysis step to release the target nucleic acids from the sample.

In an exemplary embodiment, a sample comprising RNA can be combined in a buffer solution comprising guanidinium hydrochloride, ethylenediaminetetraacetic acid (EDTA), dithiothreitol (DTT), Triton X-100, and Tris-HCL at a pH of 7.5. In another embodiment, the sample comprising RNA can be combined in a buffer solution comprising guanidinium isothiocyanate, EDTA, DTT, Triton X-100, and Tris-HCl at a pH of 7.5. The RNA is stable in such buffer solutions and it is not necessary to isolate the RNA from other sample constituents which may enhance degradation of the RNA.

In further embodiments, the buffers of the invention preferably include a denaturant, particularly a chaotropic cation, that has the effect of increasing reaction and binding efficiency in the methods and assays described herein by helping to unfold the secondary structure of the RNA. Common chaotropic molecules are guanidinium hydrochloride, guanidinium isothiocyanate, betaine or glycine betaine, urea, thiourea, and lithium perchlorate. Without being bound by theory, chaotropic agents that are effective in breaking of tertiary structure in nucleic acids are preferred and chaotropic agents that also maintain the solubility of the nucleic acid target in solution are particularly beneficial. An advantage of buffers of the invention, particularly buffers comprising a chaotropic cation, is that the buffer keeps the nucleic acids of the sample in solution. This is in contrast to other traditional buffers used in transport systems for blood-based tests, which tend to precipitate/form a cationic shell around the nucleic acids of the sample (particularly RNA). Since the buffers of the invention keep the nucleic acids in solution, and since the chemical ligation methods of the assays of the invention do not require enzymes, a sample can be collected into a buffer and the ligation probes (and in many embodiments, target capture probes) can be added to the sample and ligation products formed. To change hybridization conditions to then release the ligation products or target complexes for further analysis, the sample plus buffer can simply be diluted to dilute the denaturant and thereby change the hybridization conditions, thus allowing analysis of the nucleic acids using any of the methods described herein and known in the art.

In further embodiments, the buffers of the invention have a pH of about 5 to about 8.5. More preferably the buffer solution has a pH of about 6 to 8 and even more preferably, a pH of approximately 7.3 or 7.5.

The following sections discuss exemplary buffer components in further detail. Although each of these components is discussed separately, the present invention encompasses any combination of the following buffer components as well as any other components known in the art.

Denaturants

In preferred embodiments, buffers of the present invention include one or more denaturants. By denaturant as used herein is meant any substance that serves to unfold the double helix of nucleic acids with loss of secondary and tertiary structure. In further embodiments, the denaturants comprise a chaotropic cation, including without limitation guanidinium hydrochloride (GuHCl) and guanidinium isothiocyanate.

In further embodiments, the denaturant is guanidinium hydrochloride, which is present in a concentration from about 1 molar to about 8 molar and more preferably, a concentration of about 2 molar to about 4 molar, and even more preferably, a concentration of approximately 3 molar. In further embodiments, concentration of GuHCl in buffers of the invention range from about 0.2-10, 0.5-9, 1-8, 1.5-7, 2-6, 2.5-5, and 3.0-4.0 molar. In still further embodiments, concentrations of GuHCl in buffers of the invention are about 0.5, 1, 2, 3, 4, 5, 6, 7, 8, 9, 10, 11, 12, 13, 14 or 15 molar.

In other embodiments, the denaturant is guanidinium isothiocyanate, which is present in a concentration from about 1 molar to about 8 molar and more preferably, a concentration of about 2 molar to about 4 molar, and even more preferably, a concentration of approximately 3 molar. In further embodiments, concentration of guanidinium isothiocyanate in buffers of the invention range from about 0.2-10, 0.5, -9, 1-8, 1.5-7, 2-6, 2.5-5, and 3.0-4.0 molar. In still further embodiments, concentrations of guanidinium isothiocyanate in buffers of the invention are about 0.5, 1, 2, 3, 4, 5, 6, 7, 8, 9, 10, 11, 12, 13, 14 or 15 molar.

As will be appreciated, other denaturants known in the art can be used in buffers of the invention at similar concentrations as those listed above for guanidinium hydrochloride and guanidinium isothiocyanate.

In some embodiments, such as with the use of high concentrations of salts such as guanidinium salts, these reagents also serve as lysis agents. As will be appreciated by those in the art, in general, the use of a denaturant that also serves as a cell lysis agent is of particular use, although the present invention also contemplates the use of a first separate lysis step followed by the addition of the denaturant.

Surfactants

In some embodiments, buffers of the present invention include one or more surfactants. In further embodiments, the surfactant includes without limitation Triton X-100 and sodium N-lauroylsarcosine.

In further embodiments, the surfactant is present in buffers of the invention at a concentration from about 0.1% to about 5% by weight. In still further embodiments, the surfactant is present in a concentration of about 0.1%-10%, 0.5%-9.5%, 1%-9%, 1.5%-8.5%, 2%-8%, 2.5%-7.5%, 3%-7%, 3.5%-6.5%, 4%-6%, and 4.5%-5.5% by weight. In preferred embodiments, the surfactant has a concentration of about 0.5% to about 3%. In a further embodiment, the surfactant has a concentration of approximately 1.5% by weight.

ph Buffer

In some embodiments, buffers of the present invention include one or more pH buffers. Such pH buffers include without limitation Tris. In other embodiments the pH buffer can be one of many known by those skilled in the art. Generally the pH buffer used in the present invention includes an agent that has a pKa within one pH unit of the operating pH.

In some embodiments, the pH buffer is present in buffers of the invention at a concentration from about 10 mM to about 100 mM. In preferred embodiments, the pH buffer has a concentration of about 20 mM to about 50 mM and more preferably, a concentration of approximately 30 mM. In further embodiments, the pH buffer has a concentration of about 5-150, 10-140, 15-130, 20-120, 25-110, 30-100, 35-90, 40-80, 45-70, and 50-60 mM.

Reducing Agents

In some embodiments, buffers of the present invention include one or more reducing agents. Such reducing agents can include without limitation Dithiothreitol (DTT) and mercaptoethanol.

In further embodiments, the reducing agents have a concentration from about 1 mM to about 100 mM. In preferred embodiments, the reducing agent has a concentration of about 4 mM to about 7 mM and even more preferably, a concentration of approximately 5 mM. In still further embodiments, the reducing agents have a concentration of about 0.5-10, 1-9.5, 1.5-9, 2-8.5, 2.5-8, 3-7.5, 3.5-7, 4-6.5 mM. In yet further embodiments, the reducing agents have a concentration of about 1-150, 10-140, 15-130, 20-120, 25-110, 30-100, 35-90, 40-80, 45-70, and 50-60 mM.

EDTA

In further embodiments, buffers of the invention include EDTA at a concentration of from about 1 mM to about 100 mM. More preferably the EDTA has a concentration of about 10 mM to about 50 mM and even more preferably, a concentration of approximately 20 mM. In further embodiments, the EDTA is present at a concentration of about 1-150, 10-140, 15-130, 20-120, 25-110, 30-100, 35-90, 40-80, 45-70, and 50-60 mM. In still further embodiments, the EDTA has a concentration of about 5, 10, 15, 20, 25, 30, 35, 40, 45, 50, 55, 60 mM.

Additional Buffer Components

The buffers of the invention may further include any additional components known in the art, particularly components known in the art to be of use in reactions involving nucleic acids. Additional components may include without limitation: adjuvants, diluents, binders, stabilizers, salts (including NaCl and MgCl2), lipophilic solvents, preservatives, or the like. Buffer components may also include pharmaceutical excipients and additives, proteins, peptides, amino acids, lipids, and carbohydrates (e.g., sugars, including monosaccharides, di-, tri-, tetra-, and oligosaccharides; derivatized sugars such as alditols, aldonic acids, esterified sugars and the like; and polysaccharides or sugar polymers), which can be present singly or in combination, comprising alone or in combination 1-99.99% by weight or volume. Exemplary protein excipients include serum albumin such as human serum albumin (HSA), recombinant human albumin (rHA), gelatin, casein, and the like. Representative amino acid/antibody components, which can also function in a buffering capacity, include alanine, glycine, arginine, betaine, histidine, glutamic acid, aspartic acid, cysteine, lysine, leucine, isoleucine, valine, methionine, phenylalanine, aspartame, and the like. Carbohydrate excipients are also intended within the scope of this invention, examples of which include but are not limited to monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol) and myoinositol.

In many embodiments, the DxCollect buffer is used, which is 4.5 M guanidine hydrochloride, 120 mM sodium citrate, 80 mM citric acid, 20 mM EDTA and 0.1% (v/v) Triton X-100. The starting pH is 4.1 and about 5.0 after mixing with blood. The target buffer The target buffer to blood ratio is 2 parts buffer to 1 part blood, but it has a wide use range including up to at 5 parts buffer to 1 part blood. At 2:1 buffer to blood, the stabilized blood GuHCl concentration is 3.0M. As discussed herein, the chemical ligation assays described herein can be done in the stabilization buffer. When other assays are used, such as those that rely on enzymes (polymerase, ligase, etc., which generally denature in high salt concentrations), the stabilized sample can either be diluted down to acceptable GuHCl concentrations (usually at least 10 fold dilutions) or the target analyte (e.g. nucleic acid) is isolated (RNA or DNA) using standard kits including PaxGene, Agencourt (bead based) or Norgen kits.

Such buffers in general include a denaturant comprising a chaotropic cation, including in a non-limiting embodiment, guanidinium hydrochloride. In specific embodiments of the invention, a sample is collected directly into a buffer of the invention, and then subsequent hybridization and ligation of ligation probes is conducted in that buffer without need of purification of the nucleic acids from the sample. In certain embodiments, the sample collected into the buffer is first diluted and then subsequently methods described herein of hybridizing and ligating two or more ligation probes are conducted within that diluted sample without need of purification of the target nucleic acids in the sample.

As discussed above, ligation probes of the invention are hybridized to a target nucleic acids and then ligated without the use of a ligase enzyme. Following ligation, the new product generated (the "ligation product") can optionally be amplified by an enzymatic or chemical reaction. In the preferred embodiment, the chemical ligation reaction joins two probes that have PCR primer sites on them, e.g. universal PCR primers. Additionally, in one embodiment of the invention, one or both ligation probes contain a stuffer sequence, or variable spacer sequence, which is designed to have differing lengths for each probe set (i.e. each target sequence) thereby resulting in a ligation product having a target-specific length. Following ligation a defined length oligonucleotide can now be exponentially amplified by PCR. In accordance with one aspect of the invention, the probes can possess detectable labels (e.g. fluorescent labels, electrochemical labels, magnetic beads, nanoparticles, biotin, etc.) to aid in the identification, purification, quantification or detection of the ligated oligonucleotide product. The probes may also optionally include in their structure: anchoring oligonucleotide sequences designed for subsequent capture on a solid support (microarrays, microbeads, nanoparticles), molecule handles that promote the concentration or manipulation of the ligated product (magnetic particles, oligonucleotide coding sequences), and promoter sequences to facilitate subsequent secondary amplification of the ligated product via an enzyme like a DNA or RNA polymerase.

The ligation reactions of the invention proceed rapidly, are specific for the target(s) of interest, and can produce multiple copies of the ligated product for each target(s), resulting in an amplification (sometimes referred to herein as "product turnover") of the detectable signal. The ligation reactions of the invention do not require the presence of exogeneously added ligases, nor additional enzymes, although some secondary reactions may rely on the use of enzymes such as polymerases, as described below. Ligation chemistries can be chosen from many of the previously described chemical moieties. Preferred chemistries are ones that can be easily incorporated into routine manufacture techniques, are stable during storage, and demonstrate a large preference for target specific ligation when incorporated into a properly designed ligation probe set. Additionally, for embodiments which involve subsequent amplification by an enzyme, ligation chemistries and probe designs (including unnatural nucleotide analogs) that result in a ligation product that can be efficiently processed by an enzyme are preferred. Amplification of the target may also include turnover of the ligation product, either by destabilization, e.g. in which the ligation product has a lower or comparable affinity for the template or target nucleic acid than do the separate ligation probes, or by standard thermocycling in the presence of excess probes. Thus, upon ligation of the hybridized probes, the ligation product is released from the target, freeing the target to serve as a template for a new ligation reaction.

In further aspects of the invention and as is discussed in further detail below, specificity of the assays of the invention are optionally improved through the use of target capture probes. Target capture probes of the invention include a domain complementary to a domain on the target nucleic acid and a capture moiety. The target capture probes do not participate in the ligation reaction with the ligation probes, but are instead designed to hybridize to the target nucleic acid upstream or downstream from the ligation probes. Hybridization of the target capture probe to the target nucleic acid produces a target complex that includes the target nucleic acid, the target capture probe, and any ligation products formed on the target nucleic acid. The target complex can then be bound to a surface or substrate (such as a bead), and any unbound reactants can be separated from the target complexes bound to the surface or substrate. Thus, since any subsequent amplification and/or detection steps are performed on the subset of the original sample of target nucleic acids that were successfully hybridized with ligation probes, the specificity of the subsequent assays is improved.

EXAMPLES

The following section describes experiments performed using the devices or kits of the present invention.

Example 1: Consistency of Fluid Sample Uptake 10 collector devices that each contained a 4 mm×4 mm×9 mm open cell, medical grade polyvinyl alcohol sponge in the collector tip were tested for the consistency of their fluid absorption. The sponge was pressure fit into the collector cavity. 200 microliters of water was pipeted onto a hydrophobic parafilm surface and allowed to bead up. The film/water was weighed prior to testing. Each collector tip was brought into contact with the water drop and held there for 10 seconds allowing the water to absorb into the sponge. The films were reweighed after removal for the collector and the weight of water absorbed was determined. The weight was converted to microliters by assuming a water density of 1 gram per ml (Table 1). The average water absorption of the sponges was 107.2 ul±1.6 microliters.

TABLE 1

Consistency of fluid absorption by collectors

| Collector # | Microliters absorbed |
|---|---|
| 1 | 106.5 |
| 2 | 104.3 |
| 3 | 108.9 |
| 4 | 109.4 |
| 5 | 107.6 |
| 6 | 105.4 |

TABLE 1-continued

Consistency of fluid absorption by collectors

| Collector # | Microliters absorbed |
|---|---|
| 7 | 107.4 |
| 8 | 108.6 |
| 9 | 108.1 |
| 10 | 106.0 |
| Average | 107.2 |
| SD | 1.64 |

Example 2: RNA Stabilization at Ambient Temperature Followed by RNA Isolation 5 collector devices were assembled. 200 ul of DxCollect™ RNA stabilization buffer was loaded into the retainer cups and the tops were heat sealed with piercable polymer coated foil (product code 4ti-0530-4titude LTD). The retainer cups were placed into the collection tubes. A volunteer pricked their finger using a Surgilance SL250 safety lancet (SLB250). The first drop of blood was wiped away with a gauze pad and then 100 microliters of blood was collected by placing the tip of the collector with a 4 mm×4 mm×9 mm polyvinyl alcohol sponge against the blood drop. After the blood collection sponge was full as indicated by the red color of the sponge, the collector was inserted into the transport tube and screwed down until it clicked into place. During the screwing process, the tip of the collector pierced the polymer coated foil, allowing the DxCollect buffer to mix with the blood samples. This collection process was repeated 4 more times on the same volunteer.

One sample was immediately placed in the freezer at −20° C., and the other samples were stored at room temperature for 3, 6, 9 and 12 days before freezing. Once all of the room temperature time points were complete, the samples were thawed and the samples were accessed by piercing the resealable septa with a 200 ul pipet tip. 150 μL of stabilized blood was removed from the collected and added into a nuclease free 1.7 mL microfuge tube to which 50 μL of DxCollect RNA Precipitation Solution (DxTerity; Rancho Dominguez, Calif.) was added. Total RNA was extracted from the whole blood collected in DxCollect buffer using the Norgen Total RNA Purification Kit (Norgen Biotek Corp, Cat. No. 37500). Briefly, the RNA was mixed by vortexing for 15 seconds followed by centrifugation at 13,000 RPM in a microcentrifuge for 15 minutes at 4° C. The supernatant was then discarded and the RNA pellet resuspended in Norgen Lysis Buffer, and the purification was completed with the Norgen Total RNA Purification Kit according to manufacturer's instructions. After RNA isolation, all extracted RNA samples were analyzed for RNA concentration and RNA Integrity Number (RIN) scores using the Agilent 2100 Bioanalyzer RNA Nano kit according to manufacturer's directions (7). The Agilent Bioanalyzer RNA assay leverages microfluidics technology, enabling the quality analysis of RNA using only 1ul of sample. The assay is run on the Agilent 2100 Bioanalyzer instrument and utilises the Agilent 2100 Expert Software to analyze and display results. An RNA Integrity Number (RIN score) is generated for each sample on a scale of 1-10 (1=lowest; 10=highest) as an indication of RNA quality. The 18s/28s ratio and an estimation of concentration is also produced.

The RIN scores for the samples are shown in table 2.

TABLE 2

RNA stability overtime

| Sample | Days stored at room temperature | RNA Integrity Number (RIN) | Nanograms of Isolated RNA |
|---|---|---|---|
| 1 | 0 | 7.5 | 65 |
| 2 | 3 | 7.4 | 255 |
| 3 | 6 | 7.1 | 325 |
| 4 | 9 | 6.6 | 340 |
| 5 | 12 | 6.5 | 355 |

Example 3: Isolation of DNA and RNA from Samples Shipped by US Mail 10 collector devices were assembled. 200 ul of DxCollect™ RNA stabilization buffer was loaded into the retainer cups and the tops were heat sealed with pierceable polymer coated foil (product code 4ti-0530-4titude LTD). The retainer cups were placed into the collection tubes. 5 volunteers were each given 2 collection devices along with directions for use, a small US priority mail flat rate box with prepaid postage, and a small Ziploc bag containing 3"×3" universal sorbent pad (Uline S-7247). The volunteers took the items home and self-collected 2 blood samples using the following steps: 1. Wash hands thoroughly with soap and warm water 2.) Clean puncture site with an alcohol swab 3.) Place tip of the safety lancet (Surgilance SLB250) onto the target fingertip and press the trigger. 4.) Touch the collection stick to the drop of blood to absorb the blood. Continue to massage the finger to maintain flow until the sponge is full 5.) Once the collection sponge is full, insert the collection stick into the transport tube. 6.) Twist the applicator while pushing down until the collection stick seats firmly and clicks into the transport tube.

After collecting the blood samples, the closed collection devices were inserted the absorbent containing Ziploc bag and sealed. The bags were placed into the priority mail boxes and dropped in a US mailbox. The samples were received 1 to 5 days after mailing. The samples were frozen at −20° C. upon receipt and stored until the last device was received. The tubes were thawed at room temperature and both RNA and DNA was isolated from the blood samples.

The RNA was isolated by pipeting 150 ul of blood from the sealed collection devices via accessing through the pierceable septa. 150 µL of stabilized blood was added into a nuclease free 1.7 mL microfuge tube to which 50 µL of DxCollect RNA Precipitation Solution (DxTerity; Rancho Dominguez, Calif.) was added. Total RNA was extracted from the whole blood collected in DxCollect buffer using the Norgen Total RNA Purification Kit (Norgen Biotek Corp, Cat. No. 37500). Briefly, the RNA was mixed by vortexing for 15 seconds followed by centrifugation at 13,000 RPM in a microcentrifuge for 15 minutes at 4° C. The supernatant was then discarded and the RNA pellet resuspended in Norgen Lysis Buffer, and the purification was completed with the Norgen Total RNA Purification Kit according to manufacturer's instructions. After RNA isolation, all extracted RNA samples were analyzed for RNA concentration and RNA Integrity Number (RIN) scores using the Agilent 2100 Bioanalyzer RNA Nano kit according to manufacturer's directions (7). The Agilent Bioanalyzer RNA assay leverages microfluidics technology, enabling the quality analysis of RNA using only 1ul of sample. The assay is run on the Agilent 2100 Bioanalyzer instrument and utilises the Agilent 2100 Expert Software to analyze and display results. An RNA Integrity Number (RIN score) is generated for each sample on a scale of 1-10 (1=lowest; 10=highest) as an indication of RNA quality. The 18s/28s ratio and an estimation of concentration is also produced.

The DNA was isolated from the samples using the GeneCatcher™ gDNA 0.3-1 ml Blood Kit (Invitrogen). The genomic DNA (gDNA) was isolated according to the manufacturers recommendation except that a blood input of 150 microliters was used (instead of 300 microliters) with 30 microliters of GeneCatcher Magnetic Beads (instead of 60 microliter) and the addition of lysis buffer was omitted since the DxCollect stabilized blood is already lysed. In brief, the magnetic beads are used to capture the gDNA, and the gDNA coated beads are then isolated using a magnetic plate. Once the beads are isolated, the blood is disposed of. The isolated beads are washed, and then the DNA is eluted off of the beads. The DNA was only isolated from 4 of the blood samples.

The yields of the DNA and RNA are shown in Table 3.

TABLE 3

RNA and DNA isolation from shipped samples

| Sample | RNA RIN Score | Shipping Time (days) | RNA Recovered (ng) | DNA Recovered (ng) |
|---|---|---|---|---|
| 1 | 7.1 | 3 | 140 | 408 |
| 2 | 7 | 1 | 300 | 376 |
| 3 | 7.6 | 1 | 160 | 412 |
| 4 | 7 | 1 | 260 | 174 |
| 5 | 6.3 | 5 | 50 | NA |

Example 4: Direct Testing of Fingerstick Collected Blood Sample 3 collector device was assembled. 200 ul of DxCollect™ RNA stabilization buffer was loaded into the retainer cups and the tops were heat sealed with piercable polymer coated foil (product code 4ti-0530-4titude LTD). The retainer cups were placed into the collection tubes. Three volunteers (Donors 1-3) pricked their finger using a Surgilance SL250 safety lancet (SLB250). The first drop of blood was wiped away with a gauze pan and then 100 microliters of blood was collected by placing the tip of the collector with a 4 mm×4 mm×9 mm polyvinyl alcohol sponge against the blood drop. After the blood collection sponge was full as indicated by the red color of the sponge, the collector was inserted into the transport tube and screwed down until it clicked into place. During the screwing process, the tip of the collector pierced the polymer coated foil, allowing the DxCollect buffer to mix with the blood samples.

A 50 ul sample of stabilized blood was removed from each device and tested using a 10-gene assay (Table 4). The sequences for the probes used in the assay are shown in tables 5-8. Unless otherwise stated, all reagents were provided by DxTerity Diagnostics (Rancho Dominguez, Calif.) (Table 8). To begin, 50 µL of DxCollect stabilized blood was mixed in a 32-well plate (Axygen Scientific/Corning Inc., Union City, Calif.) with 15 µL of DirectReact buffer (CLPA Reaction Buffer), 15 µL of DirectMix A containing S-Probes (Table 5), 15 µL of DirectMix B containing L- and TC- Probes (Table 6) and 5 μL of DirectMix C (a protein digestion solution). DirectMix A contains S-probes and attenuation S-Probes (SA)-probes at the concentrations listed in Table 5. Diluent is 1 mM DTT in 1×TE Buffer. Probes are heat activated for 2-min at 95° C. after formulation. Direct Mix B Contains L-probes and TC-probes at the concentrations listed in Table 6. Diluent is 1×TE Buffer.

The plates were sealed with 8-well strip caps, (Agilent Technologies, Santa Clara, Calif.) and incubated in a Veriti® thermocycler (Life Technologies, Carlsbad, Calif.) for 5 minutes at 55° C. followed by 10 minutes at 80° C. and then 2 hours and 45 minutes at 55° C. Next, 5 μL, of DirectBeads (2.7 micron diameter streptavidin coated paramagnetic beads) were added to each well and mixed by pipetting. The samples were then incubated for an additional 15 minutes at 55° C. to allow ligation complex binding to the beads. The plate was removed from the thermal cycler and placed on a 96-well Side Skirted Magnetic Particle Concentrator (Invitrogen, Carlsbad, Calif.) for 2 minutes to capture the beads to the side of the well. The liquid reaction mixture was aspirated using a multichannel pipette (Rainin, Columbus Ohio). The beads were washed 3 times with 180 μL, DirectWash buffer (Wash solution for bead washing steps) and the wash buffer was removed. DirectTaq (containing Taq DNA polymerase, PCR buffer and dNTPs) and DirectPrime universal primer mix (Table 4), were then added to the washed beads, and the mixture was amplified by PCR (2 min at 95° C., followed by 30 cycles of: 10 s at 95° C.; 20 s at 57° C. and 20 s at 72° C.). For detection by CE, a 2 μL aliquot of the final amplified CLPA reaction was mixed with 17.5 μL of Hi-Di™ Formamide (Life Technologies, Carlsbad, Calif.) and 0.5 μL GeneScan™ 600 Liz® V2 dye Size Standard (Life Technologies) and injected into a 24-capillary array with POP-6™ polymer running on a ABI 3500xL Dx Genetic Analyzer with the Fragment Analysis Module (Life Technologies, Carlsbad, Calif.) according the manufacturers guidelines. The standard injection time was 15 seconds (at 18 kV) but was decreased to avoid saturating signals for a few samples based on manufacture recommendations.

Data Analysis

The CE electropherogram data files were processed with GeneMarker® Software, version 2.4.0 (SoftGenetics, State College, Pa.) in order to generate the peak height Relative Fluorescence Unit (RFU) values. The peak data tables were saved as .txt files and analyzed using JMP® v11.0 (SAS Institute, Cary, N.C.). The natural log (ln) was taken of the peaks heights and gene normalized values were generated by dividing the RFU values obtained from the instrument by the geometric mean of the RFU values of the MRPS5 and MRP18A genes from the same sample. The raw and normalized data are listed in table 9.

TABLE 4

Radiation Responsive and Normalization Genes Used in the Multiplex Probe Set.

| Gene Name | Gene symbol | Ref Seq ID | Ligated Product length (bp) |
|---|---|---|---|
| Mitochondrial ribosomal protein S5 | MRPS5 | NM_031902 | 115 |
| v-myc avian myelocytomatosis viral oncogene homolog | MYC | NM_002467 | 120 |
| Cyclin-dependent kinase inhibitor 1A | CDKN1A | NM_000389 | 125 |
| Cerebellar degeneration-related protein 2 | CDR2 | NM_001802 | 135 |
| BCL2-associated X protein | BAX | NM_138761 | 143 |
| Ferredoxin reductase | FDXR | NM_024417 | 148 |
| BCL2 binding component 3 | BBC3 | NM_001127240 | 155 |
| Glyceraldehyde-3-phosphate dehydrogenase | GAPDH | NM_002046 | 161 |
| Mitochondrial ribosomal protein S18A | MRPS18A | NM_018135 | 165 |
| Proliferating cell nuclear antigen | PCNA | NM_002592 | 180 |

TABLE 5

Formulation of S-Probes and Sequences in DirectMix A

| Gene | Conc (pM) | S-Probe (contains 3' phosphorothioate modification) |
|---|---|---|
| BAX | 333.4 | 5'-GGGTTCCCTAAGGGTTGGACGCGTTCTAAACGGACTGTTACCAGAGTCTGTGTCCACGGCGGCAATCATCCTC-3' (SEQ ID NO: 1) |
| BBC3 | 1333.4 | 5'-GGGTTCCCTAAGGGTTGGACGCGTTCTAAATGTACAGAAAATTCATTCCGGTATCTACAGCAGCGCATA-3' (SEQ ID NO: 2) |
| CDKN1A | 2666.8 | 5'-GGGTTCCCTAAGGGTTGGACGCGTCATGCCCTGTCCATAGCCTCTACTGCCACCATC-3' (SEQ ID NO: 3) |
| CDR2 | 666.7 | 5'-GGGTTCCCTAAGGGTTGGACGCGGCAACTAAAGATCTCCTTAAACAACGCTTTGTATTCTGGAGG-3' (SEQ ID NO: 4) |

TABLE 5-continued

Formulation of S-Probes and Sequences in DirectMix A

| Gene | Conc (pM) | S-Probe (contains 3' phosphorothioate modification) |
|---|---|---|
| FDXR | 2666.8 | 5'-GGGTTCCCTAAGGGTTGGACGCGACTCAGTGGAAACAGGCCATTAGACAGATGACCCTCCACAGTCCAGCAGTAGAGAGATGGG-3' (SEQ ID NO: 5) |
| GAPDH | 20 | 5'-GGGTTCCCTAAGGGTTGGACGCGTGGCGAGAGTGTCTCGTATCTCGCTCCTGGAAGATGGTGATGGGATT-3' (SEQ ID NO: 6) |
| MRPS18A | 2666.8 | 5'-GGGTTCCCTAAGGGTTGGACGCGTTCTAAACGGACTGTTACCAGGATGAACTGGCTAAGCAGCAGAACATCGTCA-3' (SEQ ID NO: 7) |
| MRPS5 | 1333.4 | 5'-GGGTTCCCTAAGGGTTGGACGGTGCAGTCTTCACATCTTCCCAGTCCAGTTTGACG-3' (SEQ ID NO: 8) |
| MYC | 333.4 | 5'-GGGTTCCCTAAGGGTTGGACGCGTGTTCGGTTGTTGCTGATCTGTCTCAGGACTCTGACAC-3' (SEQ ID NO: 9) |
| PCNA | 666.7 | 5'-GGGTTCCCTAAGGGTTGGACGCGTTCTAAACGGACTGTTACCACTTCACCGCAATTTTATACTCTACAACAAGGGGTACATCTGCAGACA-3' (SEQ ID NO: 10) |
| Gene | Conc. (pM) | SA-Probe (contains 3' Phosphorothioate modification) |
| GAPDH | 1313.4 | 5'CGTGGCGAGAGTGTCTCGTATCTCGCTCCTGGAAGATGGTGATGGGATT-3' (SEQ ID NO: 11) |

TABLE 6

Formulation of L-Probes and TC-Probes
and their respective sequences in DirectMix B

| Gene | Conc. (pM) | L-Probe (contains 5' dabsyl modification) |
|---|---|---|
| BAX | 333.4 | 5'-TGCAGCTCCATGTTACTGTCCAGTTCGTCCCCACAGGATGAGCCTGCTCTAGATTGGATCTTGCTGGCAC-3' (SEQ ID NO: 12) |
| BBC3 | 1333.4 | 5'-TACAGTATCTTACAGGCTGGGCCATCCCTCCCCACAGGATGAGCCTTGGAATGTCGGAAATGCTCTAGATTGGATCTTGCTGGCAC-3' (SEQ ID NO: 13) |
| CDKN1A | 2666.8 | 5'-TTAAAATGTCTGACTCCTTGTTCCGCTGCTAATCTGGCGAGAGGCTCTAGATTGGATCTTGCTGGCAC-3' (SEQ ID NO: 14) |
| CDR2 | 666.7 | 5'-TGTTGTAGGGGAACTCACGGGCTCTGGGTTGTTCTAAACGGACTGGCTCTAGATTGGATCTTGCTGGCAC-3' (SEQ ID NO: 15) |
| FDXR | 2666.8 | 5'-TAAGGGGTTAGATCGGCCCACACCTCCACCTTGGCGAGAGCTCTAGATTGGATCTTGCTGGCAC-3' (SEQ ID NO: 16) |
| GAPDH | 1333.4 | 5'-TCCATTGATGACAAGCTTCCCGTTCTCAGCTGGACTCAGTGGAAACAGGCCATTAGACAGAACAGGGCTCTAGATTGGATCTTGCTGGCAC-3' (SEQ ID NO: 17) |
| MRPS18A | 2666.8 | 5'-TAGTTATACTTGTGCTTCAGGTTCCAACGGCAGATGGACAGGATGAGCCTTGGAATGTCGGAAATGCTCTAGATTGGATCTTGCTGGCAC-3' (SEQ ID NO: 18) |

TABLE 6-continued

Formulation of L-Probes and TC-Probes
and their respective sequences in DirectMix B

| Gene | Conc. (pM) | L-Probe (contains 5' dabsyl modification) |
|---|---|---|
| MRPS5 | 1333.4 | 5'-TCTGGAACCTCATCTTCTGGCTCTGGATCCTTCCGCTCTAGATTGGATCTTGCTGGCAC-3' (SEQ ID NO: 19) |
| MYC | 333.4 | 5'-TGTCCAACTTGACCCTCTTGGCAGCAGGATAGTCGCTCTAGATTGGATCTTGCTGGCAC-3' (SEQ ID NO: 20) |
| PCNA | 666.7 | 5'-TACTGAGTGTCACCGTTGAAGAGAGTGGAGTGGCACAGGATGAGCCTTGGAATGTCGGAAATAGGGCTCTAGATTGGATCTTGCTGGCAC-3' (SEQ ID NO: 21) |

| Gene | Conc. (pM) | TC-Probe (biotinylated) |
|---|---|---|
| MRPS5 | 2666.8 | 5'-GGGACGCAACCACAATGGGCAGAGGGC-3' (SEQ ID NO: 22) |
| MRPS5 | 2666.8 | 5'-GCGGCTCTCTTCAAATTAGACCACACAGAGCGC-3' (SEQ ID NO: 23) |
| MYC | 2666.8 | 5'-GAGTGGAGGGAGGCGCTGCGTAGTTGTGCT-3' (SEQ ID NO: 24) |
| MYC | 2666.8 | 5'-ATTCTCCTCGGTGTCCGAGGACCTGGGGCTG-3' (SEQ ID NO: 25) |
| CDKN1A | 2666.8 | 5'-GCAATGAACTGAGGAGGGATGAGGTGGATGAGGA-3' (SEQ ID NO: 26) |
| CDKN1A | 2666.8 | 5'-GGAAAGACAACTACTCCCAGCCCCATATGAGCCCA-3' (SEQ ID NO: 27) |
| CDR2 | 2666.8 | 5'-GGCCAGTTCCCAGCCGCTGGCAACAGGCTCAGAC-3' (SEQ ID NO: 28) |
| CDR2 | 2666.8 | 5'-TGTTCTCTGTTCATCTATTTCCTGCTTAGTTTTC-3' (SEQ ID NO: 29) |
| BAX | 2666.8 | 5'-GCTTGAGACACTCGCTCAGCTTCTTGGTGGAC-3' (SEQ ID NO: 30) |
| BAX | 2666.8 | 5'-GAAAACATGTCAGCTGCCACTCGGAAAAAGACCTCTC-3' (SEQ ID NO: 31) |
| FDXR | 2666.8 | 5'-GGTTACCTCAGTTGCTGAAAGCTAAAACCTTGCGCGAAAAA-3' (SEQ ID NO: 32) |
| FDXR | 2666.8 | 5'-TTTCTTGGTTGCAGCTGTTTTATTTCCAGCATGTTCCCAA-3' (SEQ ID NO: 33) |
| BBC3 | 2666.8 | 5'-CAGACTCCTCCCTCTTCCGAGATTTCCCACCCTC-3' (SEQ ID NO: 34) |
| BBC3 | 2666.8 | 5'-GGAAACATACAAAAATCATGTACAAAAAAAATTAACC-3' (SEQ ID NO: 35) |
| GAPDH | 2666.8 | 5'-CGGTGCCATGGAATTTGCCATGGGTGGAATCATA-3' (SEQ ID NO: 36) |
| GAPDH | 2666.8 | 5'-GTACTCAGCGCCAGCATCGCCCCACTTGATTTTGG-3' (SEQ ID NO: 37) |
| MRPS18A | 2666.8 | 5'-GGCCAGAGGGGTTAGGAGGATTTGGACTCTCC-3' (SEQ ID NO: 38) |
| MRPS18A | 2666.8 | 5'-CTGTGATCTTTCGGGGCAGCATGCCTCCATG-3' (SEQ ID NO: 39) |
| PCNA | 2666.8 | 5'-TAAAGAAGTTCAGGTACCTCAGTGCAAAAGTTAG-3' (SEQ ID NO: 40) |
| PCNA | 2666.8 | 5'-ATCCTCGATCTTGGGAGCCAAGTAGTATTTTAAGTGTCCC-3' (SEQ ID NO: 41) |

TABLE 7

Formulation of Universal Primers and sequences in DirectPrime

| Description | Conc. (nM) | PCR Primers |
|---|---|---|
| Forward | 600 | 5'-[FAM]GGGTTCCCTAAGGGTTG-3' (SEQ ID NO: 42) |
| Reverse | 600 | 5'-GTGCCAGCAAGATCCAATCT-3' (SEQ ID NO: 43) |

TABLE 8

All reagents that are required to perform CLPA are available from DxTerity Diagnostics with the exception of DirectMix A and DirectMix B which are formulated by the end user. Directions for the formulation of DirectMix A and DirectMix B are provided by DxTerity.

| Reagents | Description | Catalog # |
|---|---|---|
| DxCollect Blood Collection Tubes (BCT) | Blood Collection Tubes. Containing 2 mL of DxCollect | 400-001 |
| DirectMix A | Contains S-probes and SA-probe at the concentrations listed in Table 1. Diluent is 1 mM DTT in 1X TE Buffer. Probes are heat activated for 2-min at 95° C. after formulation. | |
| DirectMix B | Contains L-probes and TC-probes at the concentrations listed in Table 1. Diluent is 1X TE Buffer. | |
| L-Probes (5' Ligation) | L-Probes (5' Ligation) - 50 nmole synthesis scale | 100-001 |
| S-Probes (3' Ligation) | S-Probes (3' Ligation) - 50 nmole synthesis scale | 100-002 |
| 5' TC-Probes | 5' TC-Probes - 50 nmole synthesis scale | 100-003 |
| 3' TC-Probes | 3' TC-Probes - 50 nmole synthesis scale | 100-004 |
| DirectMix C | Protein digestion solution. | 200-003 |
| DirectReact | CLPA reaction buffer. | 200-005 |
| DirectPrime | 2X PCR Primer Mix. | 200-004 |
| DirectTaq | 2X PCR Master Mix. | 200-002 |
| DirectBeads | 2.7 micron diameter streptavidin coated paramagnetic beads. | 200-006 |
| DirectWash | Wash solution for bead washing steps. | 200-001 |

TABLE 9

Direct Testing of Stabilized Blood Samples

| Sample ID | FAM 105 PRDX | FAM 110 PCR ctrl | FAM 115 MRPS5 | FAM 119 MYC | FAM 125 CDKN1A | FAM 135 CDR2 | FAM 140 BAX | FAM 149 FDXR-1 | FAM 155 BBC3 | FAM 161 GAPDH | FAM 165 MRPS18 | FAM 180 PCNA |
|---|---|---|---|---|---|---|---|---|---|---|---|---|
| Raw RFU Data | | | | | | | | | | | | |
| D1 | 4699 | 3443 | 21368 | 16624 | 6252 | 9444 | 7124 | 1896 | 4191 | 4824 | 7480 | 8204 |
| D2 | 6942 | 4190 | 17993 | 16743 | 2893 | 8637 | 7393 | 1231 | 3384 | 4396 | 6244 | 7527 |
| D3 | 4902 | 3795 | 23469 | 21446 | 2643 | 9566 | 8103 | 2049 | 2892 | 4150 | 6087 | 6256 |
| Normalized Data | | | | | | | | | | | | |
| D1 | 0.905 | 0.871 | 1.067 | 1.040 | 0.935 | 0.979 | 0.949 | 0.807 | 0.892 | 0.907 | 0.954 | 0.964 |
| D2 | 0.961 | 0.907 | 1.065 | 1.057 | 0.866 | 0.985 | 0.968 | 0.773 | 0.883 | 0.912 | 0.950 | 0.970 |
| D3 | 0.912 | 0.885 | 1.080 | 1.071 | 0.846 | 0.984 | 0.966 | 0.819 | 0.856 | 0.894 | 0.936 | 0.938 |

Advantages

The present invention finds particular use in the detection of target analytes, particularly nucleic acids, using chemical ligation buffers and systems described in US Publications 2008/0124810, 2010/0267585, 2011/0306512 and 2013/0005594, all of which are expressly incorporated by reference in their entirety, and in particular with reference to ligation moieties and buffer systems. That is, once the blood is collected and conveyed to the testing facility, the blood is processed and assayed for the presence of target analytes. A significant advantage of the systems and assays of the present invention is that small amounts of blood can be used (thus facilitating home collection via a finger stick versus needle draw), and that the blood sample is stable in the buffers in the collection device for a time sufficient to mail or otherwise convey the sample to the testing center. In addition, in the case of the chemical ligation assays described in the US Publications above, the testing can be done without further processing of the sample, e.g. the assays can be run in the lysis buffers that preclude the use of enzymatic assays.

REFERENCES CITED

All references cited herein are incorporated herein by reference in their entirety and for all purposes to the same extent as if each individual publication or patent or patent application was specifically and individually indicated to be incorporated by reference in its entirety for all purposes.

What is claimed is:

1. A device for collecting and stabilizing a biological sample, the device comprising:
   (a) a housing comprising an open end portion, a closed end portion, and an interior space;
   (b) a retainer insertable into the interior space of the housing, the retainer comprising a vessel for receiving a solution and a penetrable seal for enclosing the solution within the vessel; and
   (c) a collector removably engagable with the open end portion of the housing and capable of sealingly closing the open end portion of the housing, the collector comprising a stem portion insertable into the housing, wherein the stem portion comprising:
   a first segment;
   a second segment formed with a cavity for accommodating an absorbent member for collecting the biological sample; and
   a partition disposed between the first segment and the second segment for preventing the absorbent member from being pushed into the first segment when the collector is engaging or engaged with the open end portion of the housing, wherein the partition is made of a porous material or formed with at least one hole or slot to allow the first segment in fluidic communication with the second segment,
   wherein when the collector is engaged with the open end portion of the housing, the absorbent member is received in the housing and the second segment of the stem portion of the collector breaks the penetrable seal of the retainer that has been inserted into the interior space of the housing and propels the solution to flow through the absorbent member, thereby releasing the biological sample from the absorbent member and facilitating mixing of the biological sample with the solution.

2. The device of claim 1, wherein the collector further comprises:
   a body portion serving as a handle when taking the biological sample and as a seal when engaging or engaged with the open end portion of the housing wherein the stem portion is fixedly coupled with the body portion or monolithically formed with the body portion, wherein
   the first segment is proximal to the body portion the second segment is distal to the body portion.

3. The device of claim 1, wherein the collector further comprises a plasma membrane for generating plasma from the biological sample, wherein the plasma membrane is disposed within the second segment of the stem portion.

4. The device of claim 1, wherein:
   the first segment is formed with one or more open slots to allow the released biological sample and the propelled solution flow through.

5. The device of claim 1, wherein:
   the first segment proximal to the body portion is formed with a reservoir for facilitating mixing of the biological sample with the solution and accommodating the mixture of the biological sample and the solution.

6. The device of claim 2, wherein the collector further comprises:
   a penetrable septum for preventing the mixture of the biological sample and the solution from flowing out through the body portion.

7. The device of claim 6, wherein the penetrable septum is disposed within the body portion and adjacent to the stem portion.

8. The device of claim 1, wherein the collector further comprises:
   a first elastomeric seal disposed on an exterior surface of the second segment of the stem portion, wherein the first elastomeric seal provides sealing between the exterior surface of the second segment of the stem portion and an interior surface of the retainer when the collector is engaging or engaged with the open end portion of the housing.

9. The device of claim 1, wherein the second segment of the stem portion includes a tooth protruded from an edge of the second segment of the stem portion to facilitate breaking the penetrable seal of the retainer when the collector is engaging or engaged with the open end portion of the housing.

10. The device of claim 1, wherein the second segment of the stem portion includes a rib formed circumferentially on an exterior surface of the second segment of the stem portion, the rib performing one or more of the following: (i) acting as a plunger to assist propelling the solution to flow through the absorbent member when the collector is engaging or engaged with the open end portion of the housing, and (ii) assisting in sealing between the second segment of the stem portion and the retainer.

11. The device of claim 2, wherein the body portion comprises one or more pins formed on a side wall of the body portion and proximal to the stem portion for screwing the collector to the housing.

12. The device of claim 2, wherein the body portion comprises two pins formed on a side wall of the body portion and proximal to the stem portion for screwing the collector to the housing, wherein the two pins are opposite to each other.

13. The device of claim 2, wherein:
the body portion comprises at least one detention on a side wall of the body portion; and
the housing comprises at least one slot formed at the open end portion,
wherein the at least one detention is received by the at least one slot when the collector is engaged with the housing, thereby preventing unintentional removal of the collector from the housing after the collector is engaged with the housing.

14. The device of claim 13, wherein:
the at least one detention comprises two clips formed on the side wall of the body portion and opposite to each other; and
the at least one slot comprises two slot corresponding to the two clips.

15. The device of claim 1, wherein the vessel has an open top and a closed bottom, and a central portion of the closed bottom is recessed inwardly toward the open top such that the central portion of the closed bottom compresses the absorbent member when the collector is engaging or engaged with the open end portion of the housing, thereby squeezing the biological sample out of the absorbent member.

16. The device of claim 1, wherein the vessel has an open top, a closed bottom, and a column protruded from a central portion of the closed bottom toward the open top such that the column of the closed bottom compresses the absorbent member when the collector is engaging or engaged with the open end portion of the housing, thereby squeezing the biological sample out of the absorbent member.

17. The device of claim 1, wherein the retainer further comprises a solution retention disposed between the solution received in the vessel and the penetrable seal.

18. The device of claim 1, wherein the vessel of the retainer is tapered with an open top wider than a closed bottom.

19. The device of claim 1, wherein the vessel of the retainer comprises a reservoir adjacent to the open top for facilitating mixing of the biological sample with the solution and accommodating the mixture of the biological sample and the solution.

20. The device of claim 1, wherein:
the housing comprises a first seat formed on an interior surface of the housing for supporting the retainer once the retainer is inserted into the interior space of the housing, and
the vessel comprises a first flange formed on an exterior surface of the vessel of the retainer to abut the first shoulder.

21. The device of claim 1, wherein the open end portion of the housing are threaded with internal threads to facilitate engagement with the collector and/or insertion of the retainer.

22. The device of claim 1, wherein the closed end portion of the housing is formed with (i) a groove extended radially inwardly from an exterior surface of the closed end portion of the housing, (ii) a shoulder or flange extended radially outwardly from the exterior surface of the closed end portion of the housing, (iii) a recess at a bottom of the closed end portion of the housing, or (iv) combination thereof for retaining the housing in a rack when processed using a liquid handling robot.

23. The device of claim 1, wherein the housing comprises at least one slot and the collector comprises at least one detention corresponding to the at least one slot of the housing for interlocking the collector with the housing.

24. The device of claim 1, further comprising one or more of the following: (i) a 2D Data Matrix Bar Code printed on or attached to a bottom of the housing or an exterior surface of the housing, (ii) a readable product identification printed on or attached to the bottom of the housing or the exterior surface of the housing, and (iii) a radio-frequency identification (RFID) tag printed on or attached to the bottom of the housing or the exterior surface of the housing.

25. A kit for health care, comprising:
(a) a collector comprising:
a first segment;
a second segment formed with a cavity for accommodating an absorbent member for collecting a biological sample; and
a partition disposed between the first segment and the second segment for preventing the absorbent member from being pushed into the first segment when the collector is engaging or engaged with the open end portion of the housing, wherein the partition is made of a porous material or formed with at least one hole or slot to allow the first segment in fluidic communication with the second segment;
(b) a housing comprising an open end portion, a closed end portion, and an interior space; and
(c) a retainer insertable into the interior space of the housing, the retainer comprising a vessel for receiving a solution and a penetrable seal for enclosing the solution within the vessel,
wherein, the collector is removably engagable with the open end portion of the housing and capable of sealingly closing the open end portion of the housing, and
wherein, when the collector is engaged with the open end portion of the housing, the absorbent member is received in the housing and the second segment of the stem portion of the collector breaks the penetrable seal of the retainer that has been inserted into the interior space of the housing and propels the solution to flow through the absorbent member, thereby releasing the biological sample from the absorbent member and facilitating mixing of the biological sample with the solution.

26. A method for collecting and stabilizing a biological sample, the method comprising:

(a) providing a collector, a housing, and a retainer insertable into the housing, wherein the collector comprises:
   a first segment;
   a second segment formed with a cavity to accommodate an absorbent member for collecting the biological sample; and
   a partition disposed between the first segment and the second segment for preventing the absorbent member from being pushed into the first segment when the collector is engaging or engaged with an open end portion of the housing, wherein the partition is made of a porous material or formed with at least one hole or slot to allow the first segment in fluidic communication with the second segment;

(b) collecting the biological sample by the absorbent member; and (c) sealingly engaging the collector with the housing,
wherein, the sealingly engaging of the collector with the housing breaks a penetrable seal of the retainer that has been inserted into an interior space of the housing and propels a solution retained in the retainer to flow through the absorbent member, thereby releasing the biological sample from the absorbent member and facilitating mixing of the biological sample with the solution.

27. A device for collecting and stabilizing a biological sample, the device comprising:
   (a) a housing comprising an open end portion, a closed end portion, and an interior space;
   (b) a retainer insertable into the interior space of the housing, the retainer comprising:
      a vessel containing a stabilizing buffer, wherein the vessel comprises an open top and a closed bottom, and
      a penetrable seal sealing the open top of the vessel, thereby enclosing the stabilizing buffer within the vessel; and
   (c) a collector removably engageable with the open end portion of the housing and sized to sealingly close the open end portion of the housing, the collector comprising an absorbent member for collecting the biological sample,
   wherein said stabilizing buffer stabilizes nucleic acids in said biological sample from degradation and comprises one or more of a denaturant, a reducing agent, a surfactant, a pH buffer, and a chelator; and
   wherein when the collector is engaged with the open end portion of the housing, the absorbent member is received in the housing, wherein the collector breaks the penetrable seal of the retainer that has been inserted into the interior space of the housing and the closed bottom of the retainer remains closed such that said stabilizer buffer is propelled to flow through the absorbent member, thereby releasing the biological sample from the absorbent member and facilitating mixing of the biological sample with the stabilizer buffer.

28. A device according to claim 27 wherein said stabilizing buffer comprises a denaturant comprising a chaotropic agent.

29. A device according to claim 28 wherein said chaotropic agent is selected from the group consisting of guanidinium hydrochloride and guanidinium isothiocyantate.

30. A device according to claim 29 wherein said chaotropic agent is at a concentration such that the cells in said biological sample are lysed.

* * * * *

SEQUENCE LISTING

<160> NUMBER OF SEQ ID NOS: 45

<210> SEQ ID NO 1
<211> LENGTH: 73
<212> TYPE: DNA
<213> ORGANISM: Artificial Sequence
<220> FEATURE:
<223> OTHER INFORMATION: BAX S-Probe

<400> SEQUENCE: 1
gggttcccta agggttggac gcgttctaaa cggactgtta ccagagtctg tgtccacggc    60
ggcaatcatc ctc                                                       73

<210> SEQ ID NO 2
<211> LENGTH: 69
<212> TYPE: DNA
<213> ORGANISM: Artificial Sequence
<220> FEATURE:
<223> OTHER INFORMATION: BBC3 S-Probe

<400> SEQUENCE: 2
gggttcccta agggttggac gcgttctaaa tgtacagaaa attcattccg gtatctacag    60
cagcgcata                                                            69

<210> SEQ ID NO 3
<211> LENGTH: 57
<212> TYPE: DNA
<213> ORGANISM: Artificial Sequence
<220> FEATURE:
<223> OTHER INFORMATION: CDKN1A S-Probe

<400> SEQUENCE: 3
gggttcccta agggttggac gcgtcatgcc ctgtccatag cctctactgc caccatc       57

<210> SEQ ID NO 4
<211> LENGTH: 65
<212> TYPE: DNA
<213> ORGANISM: Artificial Sequence
<220> FEATURE:
<223> OTHER INFORMATION: CDR2 S-Probe

<400> SEQUENCE: 4
gggttcccta agggttggac gcggcaacta aagatctcct taaacaacgc tttgtattct    60
ggagg                                                                65

<210> SEQ ID NO 5
<211> LENGTH: 84
<212> TYPE: DNA
<213> ORGANISM: Artificial Sequence
<220> FEATURE:
<223> OTHER INFORMATION: FDXR S-Probe

<400> SEQUENCE: 5
gggttcccta agggttggac gcgactcagt ggaaacaggc cattagacag atgaccctcc    60
acagtccagc agtagagaga tggg                                           84

<210> SEQ ID NO 6
<211> LENGTH: 70
<212> TYPE: DNA
<213> ORGANISM: Artificial Sequence
<220> FEATURE:
<223> OTHER INFORMATION: GAPDH S-Probe

<400> SEQUENCE: 6

```
gggttccctc agggttggac gcgtggcgag agtgtctcgt atctcgctcc tggaagatgg    60
tgatgggatt                                                           70
```

<210> SEQ ID NO 7
<211> LENGTH: 75
<212> TYPE: DNA
<213> ORGANISM: Artificial Sequence
<220> FEATURE:
<223> OTHER INFORMATION: MRPS18A S-Probe

<400> SEQUENCE: 7

```
gggttccctc agggttggac gcgttctaaa cggactgtta ccaggatgaa ctggctaagc    60
agcagaacat cgtca                                                     75
```

<210> SEQ ID NO 8
<211> LENGTH: 56
<212> TYPE: DNA
<213> ORGANISM: Artificial Sequence
<220> FEATURE:
<223> OTHER INFORMATION: MRPS5 S-Probe

<400> SEQUENCE: 8

```
gggttccctc agggttggac ggtgcagtct tcacatcttc ccagtccagt ttgacg        56
```

<210> SEQ ID NO 9
<211> LENGTH: 61
<212> TYPE: DNA
<213> ORGANISM: Artificial Sequence
<220> FEATURE:
<223> OTHER INFORMATION: MYC S-Probe

<400> SEQUENCE: 9

```
gggttccctc agggttggac gcgtgttcgg ttgttgctga tctgtctcag gactctgaca    60
c                                                                    61
```

<210> SEQ ID NO 10
<211> LENGTH: 90
<212> TYPE: DNA
<213> ORGANISM: Artificial Sequence
<220> FEATURE:
<223> OTHER INFORMATION: PCNA S-Probe

<400> SEQUENCE: 10

```
gggttccctc agggttggac gcgttctaaa cggactgtta ccacttcacc gcaatttat     60 actctacaac aaggggtaca tctgcagaca                                     90
```

<210> SEQ ID NO 11
<211> LENGTH: 49
<212> TYPE: DNA
<213> ORGANISM: Artificial Sequence
<220> FEATURE:
<223> OTHER INFORMATION: GAPDH SA-Probe

<400> SEQUENCE: 11

```
cgtggcgaga gtgtctcgta tctcgctcct ggaagatggt gatgggatt                49
```

<210> SEQ ID NO 12
<211> LENGTH: 70
<212> TYPE: DNA
<213> ORGANISM: Artificial Sequence
<220> FEATURE:
<223> OTHER INFORMATION: BAX L-Probe

```
<400> SEQUENCE: 12
tgcagctcca tgttactgtc cagttcgtcc ccacaggatg agcctgctct agattggatc    60
ttgctggcac                                                          70

<210> SEQ ID NO 13
<211> LENGTH: 86
<212> TYPE: DNA
<213> ORGANISM: Artificial Sequence
<220> FEATURE:
<223> OTHER INFORMATION: BBC3 L-Probe

<400> SEQUENCE: 13
tacagtatct tacaggctgg gccatccctc cccacaggat gagccttgga atgtcggaaa    60
tgctctagat tggatcttgc tggcac                                        86

<210> SEQ ID NO 14
<211> LENGTH: 68
<212> TYPE: DNA
<213> ORGANISM: Artificial Sequence
<220> FEATURE:
<223> OTHER INFORMATION: CDKN1A L-Probe

<400> SEQUENCE: 14
ttaaaatgtc tgactccttg ttccgctgct aatctggcga gaggctctag attggatctt    60
gctggcac                                                            68

<210> SEQ ID NO 15
<211> LENGTH: 70
<212> TYPE: DNA
<213> ORGANISM: Artificial Sequence
<220> FEATURE:
<223> OTHER INFORMATION: CDR2 L-Probe

<400> SEQUENCE: 15
tgttgtaggg gaactcacgg gctctgggtt gttctaaacg gactggctct agattggatc    60
ttgctggcac                                                          70

<210> SEQ ID NO 16
<211> LENGTH: 64
<212> TYPE: DNA
<213> ORGANISM: Artificial Sequence
<220> FEATURE:
<223> OTHER INFORMATION: FDXR L-Probe

<400> SEQUENCE: 16
taaggggtta gatcggccca cacctccacc ttggcgagag ctctagattg gatcttgctg    60
gcac                                                                64

<210> SEQ ID NO 17
<211> LENGTH: 91
<212> TYPE: DNA
<213> ORGANISM: Artificial Sequence
<220> FEATURE:
<223> OTHER INFORMATION: GAPDH L-Probe

<400> SEQUENCE: 17
tccattgatg acaagcttcc cgttctcagc tggactcagt ggaaacaggc cattagacag    60
aacagggctc tagattggat cttgctggca c                                  91

<210> SEQ ID NO 18
<211> LENGTH: 90
```

```
<212> TYPE: DNA
<213> ORGANISM: Artificial Sequence
<220> FEATURE:
<223> OTHER INFORMATION: MRPS18A L-Probe

<400> SEQUENCE: 18
tagttatact tgtgcttcag gttccaacgg cagatggaca ggatgagcct tggaatgtcg    60
gaaatgctct agattggatc ttgctggcac                                    90

<210> SEQ ID NO 19
<211> LENGTH: 59
<212> TYPE: DNA
<213> ORGANISM: Artificial Sequence
<220> FEATURE:
<223> OTHER INFORMATION: MRPS5 L-Probe

<400> SEQUENCE: 19
tctggaacct catcttctgg ctctggatcc ttccgctcta gattggatct tgctggcac    59

<210> SEQ ID NO 20
<211> LENGTH: 59
<212> TYPE: DNA
<213> ORGANISM: Artificial Sequence
<220> FEATURE:
<223> OTHER INFORMATION: MYC L-Probe

<400> SEQUENCE: 20
tgtccaactt gaccctcttg gcagcaggat agtcgctcta gattggatct tgctggcac    59

<210> SEQ ID NO 21
<211> LENGTH: 90
<212> TYPE: DNA
<213> ORGANISM: Artificial Sequence
<220> FEATURE:
<223> OTHER INFORMATION: PCNA L-Probe

<400> SEQUENCE: 21
tactgagtgt caccgttgaa gagagtggag tggcacagga tgagccttgg aatgtcggaa    60
atagggctct agattggatc ttgctggcac                                    90

<210> SEQ ID NO 22
<211> LENGTH: 27
<212> TYPE: DNA
<213> ORGANISM: Artificial Sequence
<220> FEATURE:
<223> OTHER INFORMATION: MRPS5 TC-Probe

<400> SEQUENCE: 22
gggacgcaac cacaatgggc agagggc                                       27

<210> SEQ ID NO 23
<211> LENGTH: 33
<212> TYPE: DNA
<213> ORGANISM: Artificial Sequence
<220> FEATURE:
<223> OTHER INFORMATION: MRPS5 TC-Probe

<400> SEQUENCE: 23
gcggctctct tcaaattaga ccacacagag cgc                                33

<210> SEQ ID NO 24
<211> LENGTH: 30
<212> TYPE: DNA
<213> ORGANISM: Artificial Sequence
<220> FEATURE:
```

```
<223> OTHER INFORMATION: MYC TC-Probe

<400> SEQUENCE: 24
gagtggaggg aggcgctgcg tagttgtgct                                    30

<210> SEQ ID NO 25
<211> LENGTH: 31
<212> TYPE: DNA
<213> ORGANISM: Artificial Sequence
<220> FEATURE:
<223> OTHER INFORMATION: MYC TC-Probe

<400> SEQUENCE: 25
attctcctcg gtgtccgagg acctggggct g                                  31

<210> SEQ ID NO 26
<211> LENGTH: 34
<212> TYPE: DNA
<213> ORGANISM: Artificial Sequence
<220> FEATURE:
<223> OTHER INFORMATION: CDKN1A TC-Probe

<400> SEQUENCE: 26
gcaatgaact gaggagggat gaggtggatg agga                               34

<210> SEQ ID NO 27
<211> LENGTH: 35
<212> TYPE: DNA
<213> ORGANISM: Artificial Sequence
<220> FEATURE:
<223> OTHER INFORMATION: CDKN1A TC-Probe

<400> SEQUENCE: 27
ggaaagacaa ctactcccag ccccatatga gccca                              35

<210> SEQ ID NO 28
<211> LENGTH: 34
<212> TYPE: DNA
<213> ORGANISM: Artificial Sequence
<220> FEATURE:
<223> OTHER INFORMATION: CDR2 TC-Probe

<400> SEQUENCE: 28
ggccagttcc cagccgctgg caacaggctc agac                               34

<210> SEQ ID NO 29
<211> LENGTH: 68
<212> TYPE: DNA
<213> ORGANISM: Artificial Sequence
<220> FEATURE:
<223> OTHER INFORMATION: CDR2 TC-Probe

<400> SEQUENCE: 29
tgttctctgt tcatctattt cctgcttagt tttctgttct ctgttcatct atttcctgct   60
tagttttc                                                            68

<210> SEQ ID NO 30
<211> LENGTH: 32
<212> TYPE: DNA
<213> ORGANISM: Artificial Sequence
<220> FEATURE:
<223> OTHER INFORMATION: BAX TC-Probe

<400> SEQUENCE: 30
gcttgagaca ctcgctcagc ttcttggtgg ac                                 32
```

<210> SEQ ID NO 31
<211> LENGTH: 37
<212> TYPE: DNA
<213> ORGANISM: Artificial Sequence
<220> FEATURE:
<223> OTHER INFORMATION: BAX TC-Probe

<400> SEQUENCE: 31
gaaaacatgt cagctgccac tcggaaaaag acctctc    37

<210> SEQ ID NO 32
<211> LENGTH: 41
<212> TYPE: DNA
<213> ORGANISM: Artificial Sequence
<220> FEATURE:
<223> OTHER INFORMATION: FDXR TC-Probe

<400> SEQUENCE: 32
ggttacctca gttgctgaaa gctaaaacct tgcgcgaaaa a    41

<210> SEQ ID NO 33
<211> LENGTH: 40
<212> TYPE: DNA
<213> ORGANISM: Artificial Sequence
<220> FEATURE:
<223> OTHER INFORMATION: FDXR TC-Probe

<400> SEQUENCE: 33
tttcttggtt gcagctgttt tatttccagc atgttcccaa    40

<210> SEQ ID NO 34
<211> LENGTH: 34
<212> TYPE: DNA
<213> ORGANISM: Artificial Sequence
<220> FEATURE:
<223> OTHER INFORMATION: BBC3 TC-Probe

<400> SEQUENCE: 34
cagactcctc cctcttccga gatttcccac cctc    34

<210> SEQ ID NO 35
<211> LENGTH: 37
<212> TYPE: DNA
<213> ORGANISM: Artificial Sequence
<220> FEATURE:
<223> OTHER INFORMATION: BBC3 TC-Probe

<400> SEQUENCE: 35
ggaaacatac aaaaatcatg tacaaaaaaa attaacc    37

<210> SEQ ID NO 36
<211> LENGTH: 34
<212> TYPE: DNA
<213> ORGANISM: Artificial Sequence
<220> FEATURE:
<223> OTHER INFORMATION: GAPDH TC-Probe

<400> SEQUENCE: 36
cggtgccatg gaatttgcca tgggtggaat cata    34

<210> SEQ ID NO 37
<211> LENGTH: 35
<212> TYPE: DNA
<213> ORGANISM: Artificial Sequence
<220> FEATURE:

<223> OTHER INFORMATION: GAPDH TC-Probe

<400> SEQUENCE: 37
gtactcagcg ccagcatcgc cccacttgat tttgg         35

<210> SEQ ID NO 38
<211> LENGTH: 32
<212> TYPE: DNA
<213> ORGANISM: Artificial Sequence
<220> FEATURE:
<223> OTHER INFORMATION: MRPS18A TC-Probe

<400> SEQUENCE: 38
ggccagaggg gttaggagga tttggactct cc         32

<210> SEQ ID NO 39
<211> LENGTH: 31
<212> TYPE: DNA
<213> ORGANISM: Artificial Sequence
<220> FEATURE:
<223> OTHER INFORMATION: MRPS18A TC-Probe

<400> SEQUENCE: 39
ctgtgatctt tcggggcagc atgcctccat g         31

<210> SEQ ID NO 40
<211> LENGTH: 34
<212> TYPE: DNA
<213> ORGANISM: Artificial Sequence
<220> FEATURE:
<223> OTHER INFORMATION: PCNA TC-Probe

<400> SEQUENCE: 40
taaagaagtt caggtacctc agtgcaaaag ttag         34

<210> SEQ ID NO 41
<211> LENGTH: 40
<212> TYPE: DNA
<213> ORGANISM: Artificial Sequence
<220> FEATURE:
<223> OTHER INFORMATION: PCNA TC-Probe

<400> SEQUENCE: 41
atcctcgatc ttgggagcca agtagtattt taagtgtccc         40

<210> SEQ ID NO 42
<211> LENGTH: 17
<212> TYPE: DNA
<213> ORGANISM: Artificial Sequence
<220> FEATURE:
<223> OTHER INFORMATION: PCR Primer

<400> SEQUENCE: 42
gggttcccta agggttg         17

<210> SEQ ID NO 43
<211> LENGTH: 20
<212> TYPE: DNA
<213> ORGANISM: Artificial Sequence
<220> FEATURE:
<223> OTHER INFORMATION: PCR Primer

<400> SEQUENCE: 43
gtgccagcaa gatccaatct         20

```
<210> SEQ ID NO 44
<211> LENGTH: 63
<212> TYPE: DNA
<213> ORGANISM: Artificial Sequence
<220> FEATURE:
<223> OTHER INFORMATION: S-Probe: universal primer, stuffer sequence,
      target binding sequence

<400> SEQUENCE: 44
gggttcccta agggttggat cgagtctaca gatccccaac tttcatagtc tgaaactttc      60
tcc                                                                   63

<210> SEQ ID NO 45
<211> LENGTH: 41
<212> TYPE: DNA
<213> ORGANISM: Artificial Sequence
<220> FEATURE:
<223> OTHER INFORMATION: L-Probe: target binding, universal primer

<400> SEQUENCE: 45
tagcagacac atccaggctc tagattggat cttgctggca c                         41
```